(12) United States Patent
Ouyang et al.

(10) Patent No.: US 11,684,248 B2
(45) Date of Patent: Jun. 27, 2023

(54) ENDOSCOPY/STEREO COLPOSCOPY MEDICAL INSTRUMENT

(71) Applicant: MICRONVISION CORP., Bellevue, WA (US)

(72) Inventors: Xiaolong Ouyang, Bellevue, WA (US); James Ouyang, Bellevue, WA (US); Diana Ouyang, Bellevue, WA (US); Shih-Ping Wang, Los Altos, CA (US)

(73) Assignee: MicronVision Corp., Bellevue, WA (US)

( * ) Notice: Subject to any disclaimer, the term of this patent is extended or adjusted under 35 U.S.C. 154(b) by 0 days.

(21) Appl. No.: 17/835,624

(22) Filed: Jun. 8, 2022

(65) Prior Publication Data

US 2022/0296090 A1    Sep. 22, 2022

Related U.S. Application Data

(63) Continuation-in-part of application No. 17/745,526, filed on May 16, 2022, which is a continuation-in-part
(Continued)

(51) Int. Cl.
*A61B 1/00* (2006.01)
*A61B 1/05* (2006.01)
(Continued)

(52) U.S. Cl.
CPC ............ *A61B 1/05* (2013.01); *A61B 1/00009* (2013.01); *A61B 1/00052* (2013.01);
(Continued)

(58) Field of Classification Search
CPC ... A61B 1/05; A61B 1/00009; A61B 1/00052; A61B 1/00103; A61B 1/00105; A61B 1/0055; A61B 1/0661
See application file for complete search history.

(56) References Cited

U.S. PATENT DOCUMENTS

| 4,854,302 A | 8/1989 | Allred, III |
| 4,979,497 A | 12/1990 | Matsura |

(Continued)

FOREIGN PATENT DOCUMENTS

| CN | 102858275 | 1/2013 |
| EP | 1690512 | 8/2006 |

(Continued)

OTHER PUBLICATIONS

International Search Report and Written Opinion of PCT/US2016/18670, dated Jul. 12, 2016.
(Continued)

*Primary Examiner* — Anh Tuan T Nguyen
*Assistant Examiner* — Rynae E Boler
(74) *Attorney, Agent, or Firm* — Wissing Miller LLP

(57) ABSTRACT

A medical endoscopy/stereo colposcopy instrument is configured to selectively take stereo colposcopy images of a patient's uterus and endoscopy images of the patient's bladder or uterus. Any of the images can be white light images or images for a selected narrow wavelength band or fluorescence images. The images can be displayed individually or as spatially registered composite images to highlight selected features of the imaged anatomy. A cup-shaped device can be positioned at the patient's cervix and provided with a light source and a fluorescence camera module to monitor changes in fluorescence in response to a photoactivated substance.

24 Claims, 36 Drawing Sheets

Related U.S. Application Data of application No. 17/473,587, filed on Sep. 13, 2021, now Pat. No. 11,330,973, which is a continuation-in-part of application No. 17/362,043, filed on Jun. 29, 2021, now Pat. No. 11,350,816, which is a continuation-in-part of application No. PCT/US2019/036060, filed on Jun. 7, 2019, which is a continuation-in-part of application No. 16/363,209, filed on Mar. 25, 2019, which is a continuation-in-part of application No. PCT/US2017/053171, filed on Sep. 25, 2017.

(60) Provisional application No. 63/347,659, filed on Jun. 1, 2022, provisional application No. 63/346,842, filed on May 28, 2022, provisional application No. 63/346,377, filed on May 27, 2022, provisional application No. 63/218,362, filed on Jul. 4, 2021, provisional application No. 63/213,499, filed on Jun. 22, 2021, provisional application No. 63/210,034, filed on Jun. 13, 2021.

(51) Int. Cl.
   *A61B 1/005*   (2006.01)
   *A61B 1/06*    (2006.01)

(52) U.S. Cl.
   CPC ........ *A61B 1/0055* (2013.01); *A61B 1/00103* (2013.01); *A61B 1/00105* (2013.01); *A61B 1/0661* (2013.01)

(56) References Cited

U.S. PATENT DOCUMENTS

| | | |
|---|---|---|
| 5,010,876 A | 4/1991 | Henley |
| 5,188,093 A | 2/1993 | Lafferty |
| 5,281,214 A | 1/1994 | Wilkins |
| 5,323,767 A | 6/1994 | Lafferty |
| 5,329,936 A | 7/1994 | Lafferty |
| 5,486,155 A | 1/1996 | Muller |
| 5,549,547 A | 8/1996 | Cohen |
| 5,569,163 A | 10/1996 | Francis |
| 5,666,561 A | 9/1997 | Stephenson |
| 5,667,472 A | 9/1997 | Finn |
| 5,667,476 A | 9/1997 | Frassica et al. |
| 5,785,644 A | 7/1998 | Grabover |
| 5,860,953 A | 1/1999 | Snoke |
| 5,873,814 A | 2/1999 | Adair |
| 5,928,137 A | 7/1999 | Green |
| 5,935,141 A | 8/1999 | Weldon |
| 5,957,947 A | 9/1999 | Wattiez |
| 6,007,531 A | 12/1999 | Snoke |
| 6,007,546 A | 12/1999 | Snow |
| 6,017,322 A | 1/2000 | Snoke |
| 6,033,378 A | 3/2000 | Lundquist |
| 6,059,719 A | 5/2000 | Yamamato et al. |
| 6,095,970 A | 8/2000 | Hidaka |
| 6,174,307 B1 | 1/2001 | Daniel |
| 6,210,416 B1 | 4/2001 | Chu |
| 6,211,904 B1 | 4/2001 | Adair |
| 6,221,007 B1 | 4/2001 | Green |
| 6,221,070 B1 | 4/2001 | Tu et al. |
| 6,261,226 B1 | 7/2001 | McKenna |
| 6,280,386 B1 | 8/2001 | Alfano |
| 6,331,174 B1 | 12/2001 | Reinhard |
| 6,387,043 B1 | 5/2002 | Yoon |
| 6,398,743 B1 | 6/2002 | Halseth |
| 6,507,699 B2 | 1/2003 | Lemoine |
| 6,518,823 B1 | 2/2003 | Kawai |
| 6,793,882 B1 | 9/2004 | Verschuur |
| 6,917,380 B1 | 7/2005 | Tay |
| 7,256,446 B2 | 8/2007 | Hu |
| 7,428,378 B1 | 9/2008 | Warpakowski |
| 7,507,205 B2 | 3/2009 | Borovsky |
| 7,591,799 B2 | 9/2009 | Selkee |
| 7,606,609 B2 | 10/2009 | Muranushi |
| 7,780,650 B2 | 8/2010 | Frassica |
| 7,798,995 B2 | 9/2010 | Yue |
| 7,931,616 B2 | 4/2011 | Selkee |
| 7,946,981 B1 | 5/2011 | Cubb |
| 8,057,464 B2 | 9/2011 | Chen |
| 8,052,609 B2 | 11/2011 | Harhen |
| 8,187,171 B2 | 5/2012 | Irion |
| 8,197,398 B2 | 6/2012 | Scholly |
| 8,235,975 B2 | 8/2012 | Chen |
| 8,361,775 B2 | 4/2013 | Flower |
| 8,460,182 B2 | 6/2013 | Ouyang |
| 8,523,808 B2 | 9/2013 | Selkee |
| 8,696,552 B2 | 4/2014 | Whitman |
| 8,803,960 B2 | 8/2014 | Sonnenschein |
| 8,834,357 B2 | 9/2014 | Oskin |
| 8,845,522 B2 | 9/2014 | McIntyre |
| 8,952,312 B2 | 2/2015 | Blanqart |
| 8,998,844 B2 | 4/2015 | Reed |
| 9,649,014 B2 | 5/2017 | Ouyang |
| 9,736,342 B2 | 8/2017 | Mueckl |
| 9,895,048 B2 | 2/2018 | Ouyang |
| 10,278,563 B2 | 5/2019 | Ouyang |
| 10,292,571 B2 | 5/2019 | Ouyang |
| 10,595,710 B2 | 3/2020 | Gill |
| 11,330,973 B2 | 5/2022 | Ouyang |
| 2001/0007051 A1 | 7/2001 | Nakashima |
| 2001/0049509 A1 | 12/2001 | Sekine |
| 2003/0016284 A1 | 1/2003 | Squilla |
| 2003/0023142 A1 | 1/2003 | Grabover |
| 2003/0078476 A1 | 4/2003 | Hill |
| 2003/0078502 A1 | 4/2003 | Miyaki |
| 2003/0151680 A1 | 8/2003 | McDermott |
| 2003/0199735 A1 | 10/2003 | Dickopp |
| 2004/0054254 A1 | 3/2004 | Miyake |
| 2004/0054259 A1 | 3/2004 | Hasegawa |
| 2004/0138558 A1 | 7/2004 | Dunki-Jacobs |
| 2004/0162572 A1 | 8/2004 | Sauer |
| 2005/0010178 A1 | 1/2005 | Katz |
| 2005/0264687 A1 | 1/2005 | Murayama |
| 2005/0049459 A1 | 3/2005 | Hern |
| 2005/0085695 A1 | 4/2005 | Sherner |
| 2005/0154262 A1 | 7/2005 | Banik |
| 2005/0159646 A1 | 7/2005 | Nordstrom |
| 2005/0177027 A1 | 8/2005 | Hirata |
| 2005/0277874 A1 | 12/2005 | Selkee |
| 2005/0277875 A1 | 12/2005 | Selkee |
| 2006/0052710 A1 | 3/2006 | Miura |
| 2006/0063976 A1 | 3/2006 | Aizenfeld |
| 2006/0114986 A1 | 6/2006 | Knapp |
| 2006/0152601 A1 | 7/2006 | Parekh |
| 2006/0167340 A1 | 7/2006 | Peas |
| 2006/0171693 A1 | 8/2006 | Todd |
| 2006/0173245 A1 | 8/2006 | Todd |
| 2006/0184227 A1 | 8/2006 | Rust |
| 2006/0259124 A1 | 11/2006 | Matsuoka |
| 2006/0287576 A1 | 12/2006 | Tsuji |
| 2007/0060789 A1 | 3/2007 | Uchimura |
| 2007/0081920 A1 | 4/2007 | Murphy |
| 2007/0117437 A1 | 5/2007 | Boehnlein |
| 2007/0129604 A1 | 6/2007 | Hatcher |
| 2007/0162095 A1 | 7/2007 | Kimmel |
| 2007/0167678 A1 | 7/2007 | Moskowitz |
| 2007/0167868 A1 | 7/2007 | Sauer |
| 2007/0173693 A1 | 7/2007 | Refael |
| 2007/0188604 A1 | 8/2007 | Miyamoto |
| 2007/0197875 A1 | 8/2007 | Osaka |
| 2007/0210162 A1 | 9/2007 | Keen |
| 2007/0225556 A1 | 9/2007 | Ortiz |
| 2007/0238927 A1 | 10/2007 | Ueno |
| 2008/0004642 A1 | 1/2008 | Birk |
| 2008/0071144 A1 | 3/2008 | Kimmel |
| 2008/0097550 A1 | 4/2008 | Dicks |
| 2008/0108869 A1 | 5/2008 | Sanders |
| 2008/0195125 A1 | 8/2008 | Orbay |
| 2008/0195128 A1 | 8/2008 | Orbay |
| 2008/0225410 A1 | 9/2008 | Ning |
| 2008/0234547 A1 | 9/2008 | Irion et al. |

(56) References Cited

U.S. PATENT DOCUMENTS

| | | |
|---|---|---|
| 2008/0255416 A1 | 10/2008 | Gilboa |
| 2008/0262306 A1 | 10/2008 | Kawai |
| 2008/0300456 A1 | 12/2008 | Irion |
| 2009/0027489 A1 | 1/2009 | Takemura |
| 2009/0065565 A1 | 3/2009 | Lemoine |
| 2009/0076321 A1 | 3/2009 | Suyama |
| 2009/0076328 A1 | 3/2009 | Root |
| 2009/0080214 A1 | 3/2009 | Watanabe |
| 2009/0105538 A1 | 4/2009 | Van Dam |
| 2009/0118580 A1 | 5/2009 | Sun |
| 2009/0118641 A1 | 5/2009 | Van Dam |
| 2009/0149713 A1 | 7/2009 | Niida |
| 2009/0225159 A1 | 9/2009 | Schneider |
| 2009/0227897 A1 | 9/2009 | Wendt |
| 2009/0286412 A1 | 11/2009 | Ikeda |
| 2009/0287663 A1 | 11/2009 | Takeuchi |
| 2010/0069834 A1 | 3/2010 | Schultz |
| 2010/0094216 A1 | 4/2010 | Yue |
| 2010/0095969 A1 | 4/2010 | Schwartz |
| 2010/0101569 A1 | 4/2010 | Kim |
| 2010/0121142 A1 | 5/2010 | Ouyang |
| 2010/0157039 A1 | 6/2010 | Sugai |
| 2010/0160914 A1 | 6/2010 | Bastian |
| 2010/0168827 A1 | 7/2010 | Schultz |
| 2010/0191051 A1 | 7/2010 | Miyake |
| 2010/0191053 A1 | 7/2010 | Garcia |
| 2010/0234736 A1 | 9/2010 | Corl |
| 2010/0026201 A1 | 10/2010 | Frangioni |
| 2011/0009694 A1* | 1/2011 | Schultz ............... A61B 1/0008 600/109 |
| 2011/0034769 A1 | 2/2011 | Adair |
| 2011/0037876 A1 | 2/2011 | Talbert |
| 2011/0554446 | 3/2011 | Schultz |
| 2011/0092775 A1 | 4/2011 | Deshmukh |
| 2011/0105839 A1 | 5/2011 | Hoffman |
| 2011/0112622 A1 | 5/2011 | Phan |
| 2011/0130627 A1 | 6/2011 | McGrail |
| 2011/0211115 A1 | 9/2011 | Tsai |
| 2011/0213206 A1 | 9/2011 | Boutillette |
| 2011/0245602 A1 | 10/2011 | Brannon |
| 2011/0264191 A1 | 10/2011 | Rothstein |
| 2011/0288482 A1 | 11/2011 | Farrell |
| 2012/0004508 A1* | 1/2012 | McDowall ........... A61B 1/3132 600/178 |
| 2012/0016191 A1 | 1/2012 | Ito |
| 2012/0040305 A1 | 2/2012 | Karazivan |
| 2012/0041533 A1 | 2/2012 | Bertolino |
| 2012/0053515 A1 | 3/2012 | Crank |
| 2012/0100729 A1 | 4/2012 | Edidin |
| 2012/0165916 A1 | 6/2012 | Jordan |
| 2012/0178991 A1 | 7/2012 | Clark |
| 2012/0226103 A1 | 9/2012 | Gunday |
| 2012/0236138 A1 | 9/2012 | Liu |
| 2012/0245242 A1 | 9/2012 | Peiffer |
| 2012/0245418 A1 | 9/2012 | Boulais |
| 2012/0253116 A1 | 10/2012 | Sniffin |
| 2012/0259203 A1 | 10/2012 | Devereux |
| 2012/0286020 A1 | 11/2012 | Smith |
| 2012/0289858 A1 | 11/2012 | Ouyang |
| 2013/0035553 A1 | 2/2013 | Kongstorum |
| 2013/0046142 A1 | 2/2013 | Remijan |
| 2013/0057667 A1 | 5/2013 | McGrath |
| 2013/0150672 A1 | 6/2013 | Fujitani |
| 2013/0172676 A1 | 7/2013 | Levy |
| 2013/0225921 A1 | 8/2013 | Liu |
| 2013/0253402 A1 | 9/2013 | Badawi |
| 2013/0289559 A1 | 10/2013 | Reid |
| 2013/0324973 A1 | 12/2013 | Reed |
| 2013/0345514 A1 | 12/2013 | Manion |
| 2014/0022649 A1 | 1/2014 | Echhardt |
| 2014/0107416 A1 | 4/2014 | Bimkrant |
| 2014/0111634 A1 | 4/2014 | Mueckl |
| 2014/0154399 A1 | 6/2014 | Weikart |
| 2014/0180007 A1 | 6/2014 | Edidin |
| 2014/0188211 A1 | 7/2014 | Roeder |
| 2014/0213848 A1 | 7/2014 | Moskowitz |
| 2014/0228635 A1 | 8/2014 | Tuliakov |
| 2014/0275763 A1 | 9/2014 | King |
| 2014/0296866 A1 | 10/2014 | Salman |
| 2014/0323991 A1 | 10/2014 | Tang |
| 2015/0005575 A1 | 1/2015 | Kobayashi |
| 2015/0011830 A1 | 1/2015 | Hunter |
| 2015/0018622 A1 | 1/2015 | Tesar |
| 2015/0018710 A1 | 1/2015 | Furlong |
| 2015/0150441 A1 | 6/2015 | Ouyang |
| 2015/0164313 A1 | 6/2015 | Oyuang |
| 2015/0196197 A1 | 7/2015 | Kienzle |
| 2015/0238251 A1 | 8/2015 | Shikhman |
| 2015/0297311 A1 | 10/2015 | Tesar |
| 2016/0073853 A1 | 3/2016 | Venkatesan et al. |
| 2016/0077008 A1 | 3/2016 | Takasu |
| 2016/0174819 A1 | 6/2016 | Ouyang |
| 2016/0334694 A1 | 11/2016 | Liu |
| 2016/0367119 A1 | 12/2016 | Ouyang |
| 2017/0086651 A1 | 3/2017 | Sato |
| 2017/0181853 A1 | 6/2017 | Rothstein |
| 2017/0188793 A1 | 7/2017 | Ouyang |
| 2017/0188795 A1 | 7/2017 | Ouyang |
| 2017/0215699 A1 | 8/2017 | Ouyang |
| 2017/0295347 A1 | 10/2017 | Schneider |
| 2017/0310858 A1 | 10/2017 | Mueckl |
| 2018/0132700 A1* | 5/2018 | Ouyang ............ A61B 1/00016 |
| 2018/0184892 A1 | 7/2018 | Truckai |
| 2018/0235441 A1 | 8/2018 | Huang |
| 2018/0256009 A1 | 9/2018 | Ouyang |
| 2019/0029497 A1 | 1/2019 | Mirza |
| 2019/0142262 A1 | 5/2019 | Inglis |
| 2019/0216325 A1 | 7/2019 | Ouyang |
| 2019/0223691 A1 | 7/2019 | Takatsuji |
| 2019/0246873 A1 | 8/2019 | Lu |
| 2019/0246884 A1 | 8/2019 | Lu et al. |
| 2019/0282073 A1 | 9/2019 | Truckai |
| 2019/0320879 A1 | 10/2019 | Langell |
| 2019/0374095 A1 | 12/2019 | Lord |
| 2020/0204776 A1 | 6/2020 | Themelis |
| 2020/0214739 A1 | 7/2020 | Shi |
| 2020/0275827 A1 | 9/2020 | Weise |
| 2021/0052383 A1 | 2/2021 | Rothstein |
| 2021/0228806 A1 | 7/2021 | Streeter |
| 2021/0401277 A1 | 12/2021 | Ouyang |

FOREIGN PATENT DOCUMENTS

| | | |
|---|---|---|
| EP | 2560589 | 4/2010 |
| EP | 3384879 | 4/2011 |
| EP | 2749258 | 7/2014 |
| EP | 3078354 | 10/2016 |
| JP | 2009148420 | 7/2009 |
| WO | 2011133792 | 10/2011 |
| WO | 2012060932 | 5/2012 |
| WO | 2014031192 | 2/2014 |
| WO | 2014065901 | 5/2015 |
| WO | 2016032729 | 3/2016 |
| WO | 2016040131 | 3/2016 |
| WO | 2016137838 | 9/2016 |
| WO | 2018136950 | 7/2018 |
| WO | 2019237003 | 12/2019 |

OTHER PUBLICATIONS

International Search Report and Written Opinion of PCT/US2018/014880, dated Jun. 6, 2018.
International Search Report and Written Opinion of PCT/US2018/065396, dated Feb. 24, 2017.
International Search Report and Written Opinion of PCT/US2021/050095 dated Dec. 17, 2021.
International Search Report and Written Opinion of PCT/US2019/036060 dated Aug. 27, 2019.
International Search Report and Written Opinion of PCT/US2017/053171 dated Dec. 5, 2017.
International Preliminary Report on Patentability of PCT/US2017/053171 completed on Jul. 1, 2019.

(56) References Cited

OTHER PUBLICATIONS

European Search Report of European Patent Application No. EP19816177 completed Feb. 2, 2022.
Qiongshui Wu et al., A multispectral imaging analysis system for early detection of cervical cancer, Proceedings vol. 5745, Medical Imaging 2005: Physics of Medical Imaging.
Pei Wang et al., Multispectral Image under Tissue Classification Algorithm in Screening of Cervical Cancer, J Health Eng. 2022; 2022: 9048123, Published online Jan. 7, 2022.
International Preliminary Report on Patentability for PCT/US2021/050095, dated Mar. 23, 2023.

* cited by examiner

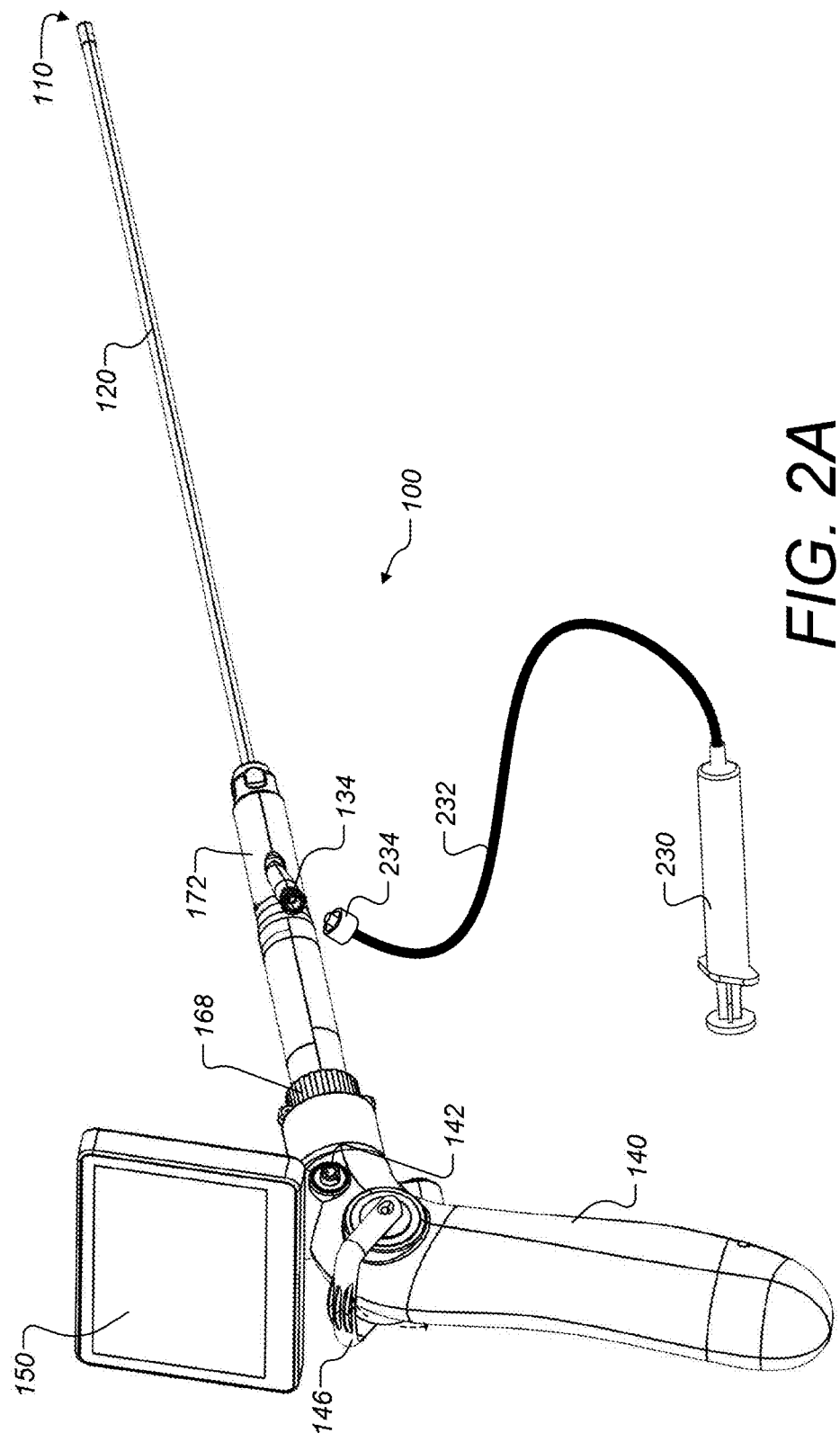

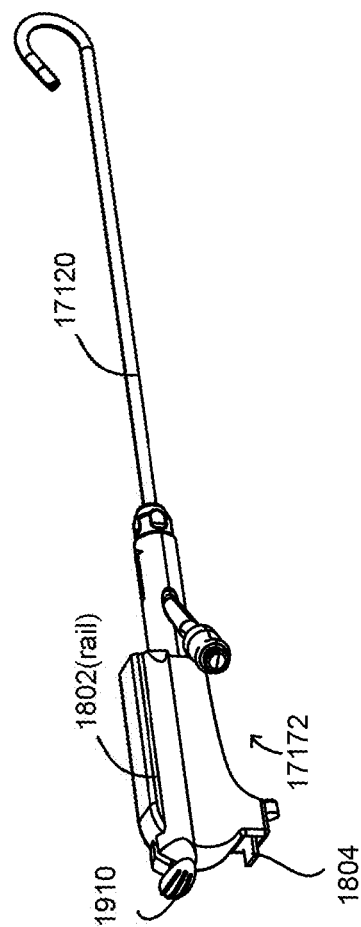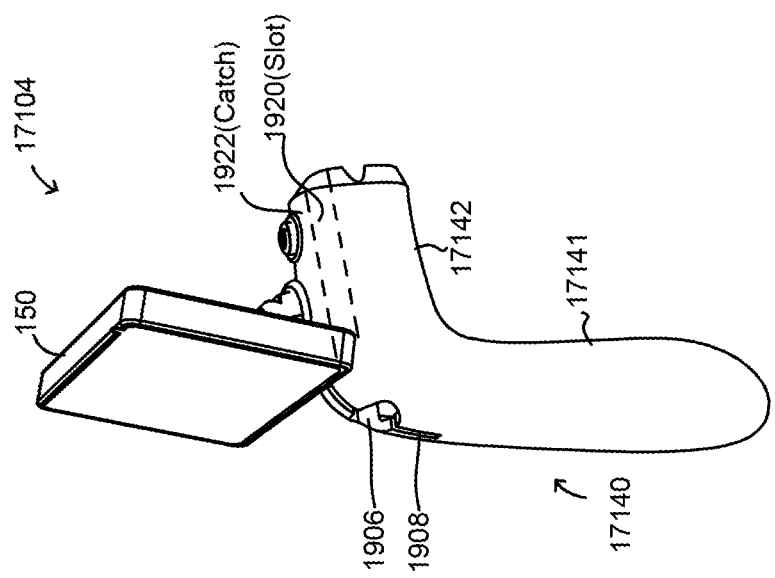
Fig. 18

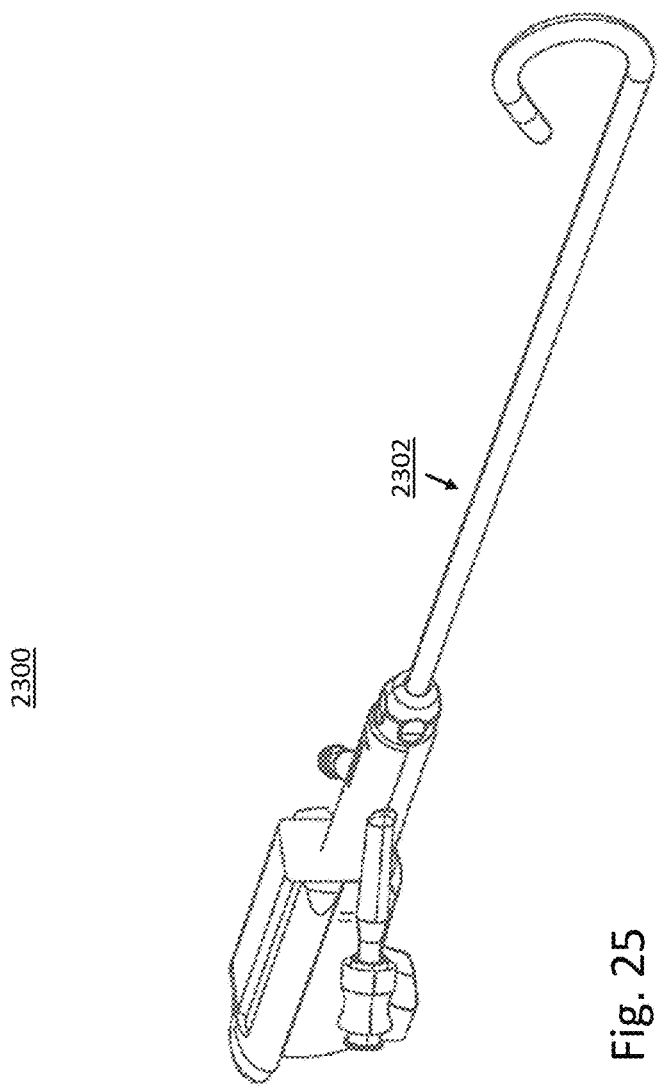
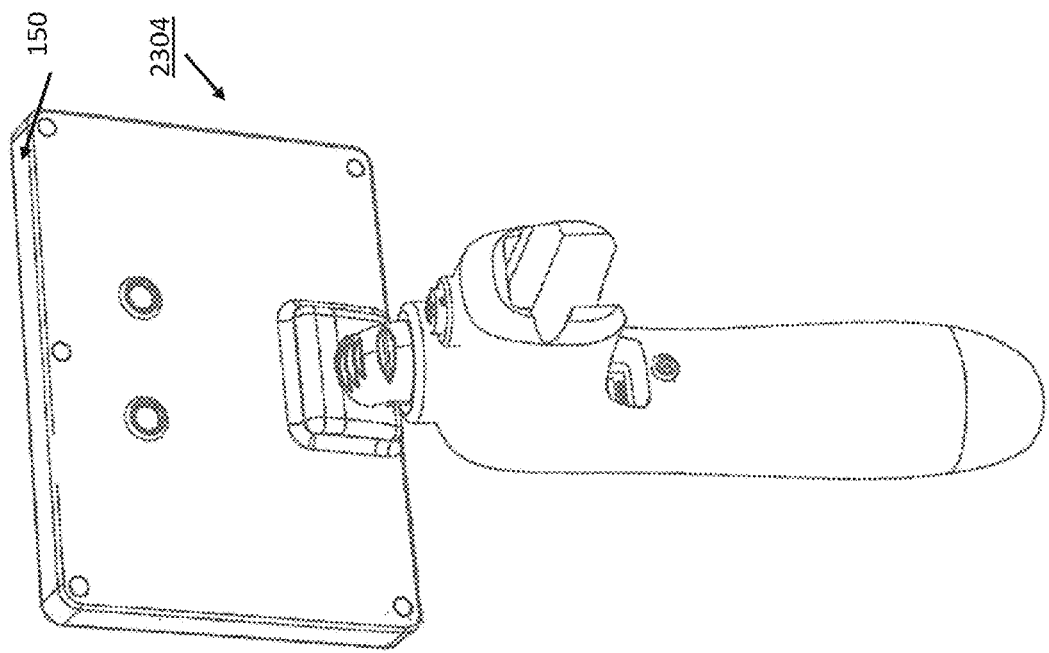
Fig. 25

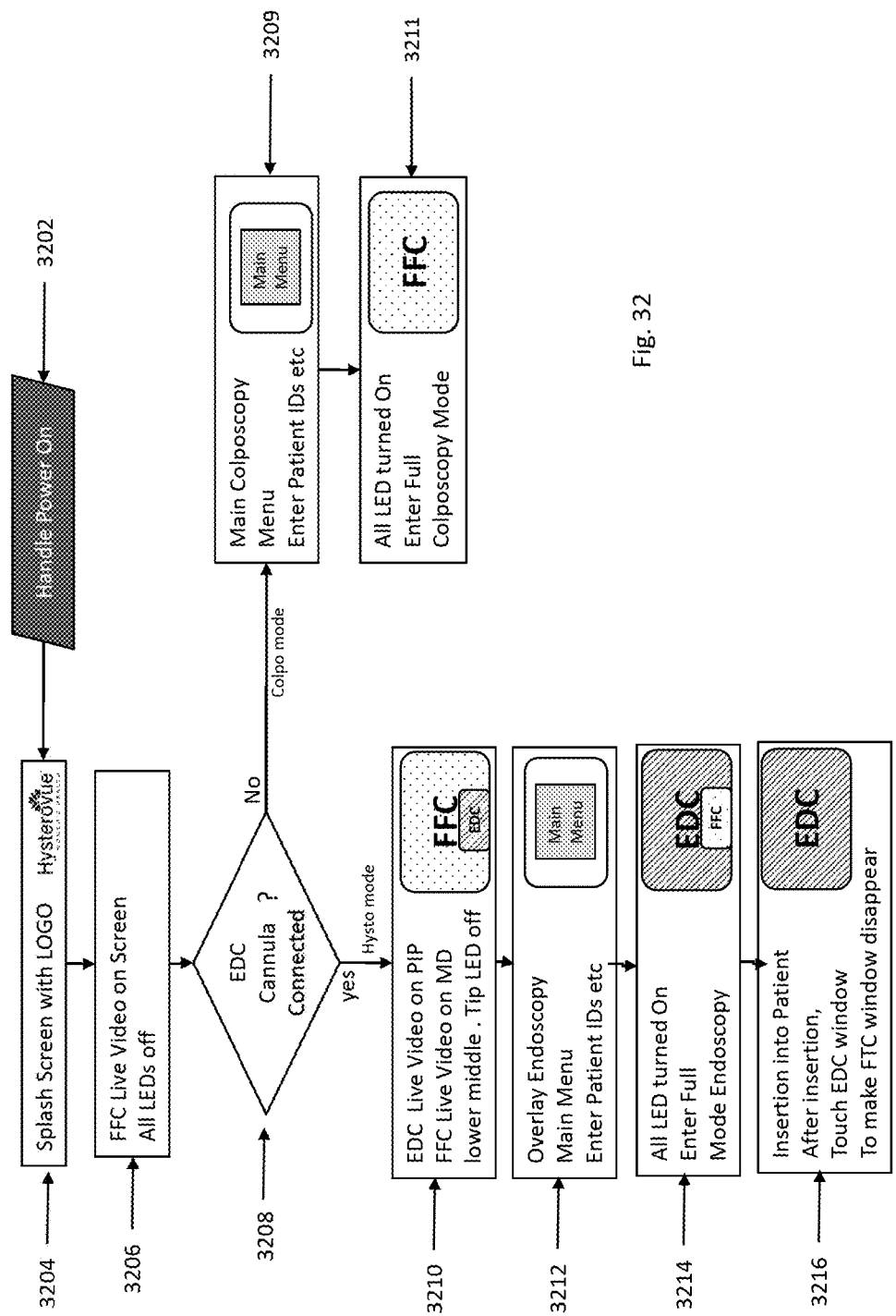

ENDOSCOPY/STEREO COLPOSCOPY MEDICAL INSTRUMENT

REFERENCE TO RELATED APPLICATIONS

This application is a continuation-in-part of U.S. patent application Ser. No. 17/745,526 filed May 16, 2022, which is a continuation-in-part of U.S. patent application Ser. No. 17/473,587 filed Sep. 13, 2021 and now U.S. Pat. No. 11,330,973, which is a continuation-in-part of each of: U.S. patent application Ser. No. 17/362,043 filed Jun. 29, 2021, now U.S. Pat. No. 11,350,816, issued Jun. 7, 2022; International Patent Appl. No. PCT/US19/36060 filed Jun. 7, 2019; U.S. patent application Ser. No. 16/363,209 filed Mar. 25, 2019 and published as US Pat. Appl. Publ. No. US2019/0216325, and International Patent Appl. No. PCT/US17/53171 filed Sep. 25, 2017.

This application claims the benefit of and incorporates by reference U.S. Provisional Patent Applications Ser. No. 63/346,377 filed May 27, 2022, 63/346,842 filed May 28, 2022, and 63/347,659 filed Jun. 1, 2022.

This application incorporates by reference the entirety of the foregoing patent applications and claims the benefit of the filing date of each of the above-identified patent applications, as well as of the applications that they incorporated by reference, directly or indirectly, and the benefit of which they claim, including U.S. provisional applications, U.S. non-provisional applications, and international applications.

Said U.S. patent application Ser. No. 17/473,587 claims the benefit of and incorporates by reference each of the following provisional applications:
U.S. Prov. Ser. No. 63/218,362 filed Jul. 4, 2021
U.S. Prov. Ser. No. 63/213,499 filed Jun. 22, 2021
U.S. Prov. Ser. No. 63/210,034 filed Jun. 13, 2021
U.S. Prov. Ser. No. 63/197,639 filed Jun. 7, 2021
U.S. Prov. Ser. No. 63/197,611 filed Jun. 7, 2021
U.S. Prov. Ser. No. 63/183,151 filed May 3, 2021;
U.S. Prov. Ser. No. 63/153,252 filed Feb. 24, 2021;
U.S. Prov. Ser. No. 63/149,338 filed Feb. 14, 2021;
U.S. Prov. Ser. No. 63/138,751 filed Jan. 18, 2021;
U.S. Prov. Ser. No. 63/129,703 filed Dec. 23, 2020;
U.S. Prov. Ser. No. 63/124,803 filed Dec. 13, 2020;
U.S. Prov. Ser. No. 63/121,924 filed Dec. 6, 2020;
U.S. Prov. Ser. No. 63/121,246 filed Dec. 4, 2020;
U.S. Prov. Ser. No. 63/107,344 filed Oct. 29, 2020;
U.S. Prov. Ser. No. 63/087,935 filed Oct. 6, 2020;
U.S. Prov. Ser. No. 63/083,932 filed Sep. 27, 2020;
U.S. Prov. Ser. No. 63/077,675 filed Sep. 13, 2020; and
U.S. Prov. Ser. No. 63/077,635 filed Sep. 13, 2020.

This patent application is also related to and incorporates by reference each of the following international, non-provisional and provisional applications:
International Patent Application No. PCT/US17/53171 filed Sep. 25, 2017;
U.S. Pat. No. 8,702,594 Issued Apr. 22, 2014;
U.S. patent application Ser. No. 16/363,209 filed Mar. 25, 2019;
International Patent Application No. PCT/US19/36060 filed Jun. 7, 2019;
U.S. patent application Ser. No. 16/972,989 filed Dec. 7, 2020;
U.S. Prov. Ser. No. 62/816,366 filed Mar. 11, 2019;
U.S. Prov. Ser. No. 62/671,445 filed May 15, 2018;
U.S. Prov. Ser. No. 62/654,295 filed Apr. 6, 2018;
U.S. Prov. Ser. No. 62/647,817 filed Mar. 25, 2018;
U.S. Prov. Ser. No. 62/558,818 filed Sep. 14, 2017;
U.S. Prov. Ser. No. 62/550,581 filed Aug. 26, 2017;
U.S. Prov. Ser. No. 62/550,560 filed Aug. 25, 2017;
U.S. Prov. Ser. No. 62/550,188 filed Aug. 25, 2017;
U.S. Prov. Ser. No. 62/502,670 filed May 6, 2017;
U.S. Prov. Ser. No. 62/485,641 filed Apr. 14, 2017;
U.S. Prov. Ser. No. 62/485,454 filed Apr. 14, 2017;
U.S. Prov. Ser. No. 62/429,368 filed Dec. 2, 2016;
U.S. Prov. Ser. No. 62/428,018 filed Nov. 30, 2016;
U.S. Prov. Ser. No. 62/424,381 filed Nov. 18, 2016;
U.S. Prov. Ser. No. 62/423,213 filed Nov. 17, 2016;
U.S. Prov. Ser. No. 62/405,915 filed Oct. 8, 2016;
U.S. Prov. Ser. No. 62/399,712 filed Sep. 26, 2016;
U.S. Prov. Ser. No. 62/399,436 filed Sep. 25, 2016;
U.S. Prov. Ser. No. 62/399,429 filed Sep. 25, 2016;
U.S. Prov. Ser. No. 62/287,901 filed Jan. 28, 2016;
U.S. Prov. Ser. No. 62/279,784 filed Jan. 17, 2016;
U.S. Prov. Ser. No. 62/275,241 filed Jan. 6, 2016;
U.S. Prov. Ser. No. 62/275,222 filed Jan. 5, 2016;
U.S. Prov. Ser. No. 62/259,991 filed Nov. 25, 2015;
U.S. Prov. Ser. No. 62/254,718 filed Nov. 13, 2015;
U.S. Prov. Ser. No. 62/139,754 filed Mar. 29, 2015;
U.S. Prov. Ser. No. 62/120,316 filed Feb. 24, 2015; and
U.S. Prov. Ser. No. 62/119,521 filed Feb. 23, 2015.

All the above-referenced non-provisional, provisional, and international patent applications are collectively referenced herein as "the commonly assigned incorporated applications."

FIELD

This patent specification generally relates mainly to endoscopy and colposcopy instruments and methods. More particularly, some embodiments relate to portable such instruments that include a re-usable portion that has both endoscopy and colposcopy functionalities and a releasably attached disposable or single-use portion with endoscopy functionality.

BACKGROUND

Endoscopes have long been used to view and treat internal tissue. In the case of both rigid and flexible conventional endoscopes, the optical system and related components are relatively expensive and are intended to be re-used many times. Therefore, stringent decontamination and disinfection procedures need to be carried out after each use. In recent years, disposable endoscopes have been developed and improved, typically comprising a single-use portion that includes a cannula with a camera at the distal that releasably attached to a reusable portion that includes image processing electronics and a display. Disposable or single-use endoscopy significantly lessens the risk of cross-contamination and hospital acquired diseases. Such endoscopes find applications in medical procedures such as imaging and treating the male and female urinary system and the female reproductive system and other internal organs. Examples of disposable endoscopes are discussed in U.S. Pat. Nos. 10,292,571, 10,874,287, 11,013,396, and 11,071,442

Colposcopy is an entirely separate technical and medical field concerned with visually examining the cervix, vagina, and vulva to identify dues suggestive of cervical cancer. A colposcope usually uses magnification. Early detection of cervical cancer is important for successful treatment and increasing survival. Papanicolaou test (Pap smear) is a popular and effective screening test for cervical cancer, but it is subjective and skilled-labor intensive. Digital cameras can obtain multi-spectral images of the cervix highlighting suspicious areas, and high-resolution optical technologies can further interrogate suspicious areas, providing in vivo diagnosis with good sensitivity and specificity. In addition, targeted contrast agents can highlight changes in biomarkers of cervical neoplasia. Multispectral imaging using a liquid crystal tunable filter (LCTF) for fast wavelength selection can be included. See Quiong Wu, Hengyu Ke, Hong Zheng, Xijian Gao, Diancheng Wang, A multispectral imaging analysis system for early detection of cervical cancer, Proceedings Volume 5745, Medical Imaging 2005; Physics of Medical Imaging; (2005) doi.org/10.1117/12.592576.

The subject matter described or claimed in this patent specification is not limited to embodiments that solve any specific disadvantages or that operate only in environments such as those described above. Rather, the above background is only provided to illustrate one exemplary technology area where some embodiments described herein may be practiced.

SUMMARY

As described in the initially presented claims but subject to amendments thereof in the course of prosecuting this patent application:

According to some embodiments, a medical endoscopy/stereo colposcopy instrument comprises: a reusable portion that includes a handle configured to be grasped by a user's hand and a display mounted to the reusable portion; a forward-facing colposcopy imaging and lighting system mounted to said reusable portion and comprising a first colposcopy camera FFC1 and first light source S1 and a second colposcopy camera FFC2 and second light source S2, configured to take stereo colposcopy images of a patient's cervix for display at said display; a single-use portion comprising a cannula configured for insertion in the patient and having an endoscopy imaging and lighting system comprising an endoscopy camera and endoscopy light source at a distal end of the cannula; interlocking mounts at a proximal end of the single-use portion and at the reusable portion, configured to releasably couple the reusable and single-use portions to each other to thereby form an assembled endoscope configured to take endoscopy images with said endoscopic imaging and lighting system for display at said display; and a processor configured to process image data from said colposcopy imaging and lighting system and said endoscopy imaging and lighting system into colposcopy images and endoscopy images and to cause said display to show one or both the colposcopy and endoscopy images.

According to some embodiments, the instrument can further include one or more of the following features: (a) the cameras FFC1 and FFC2 and the light sources S1 and S2 can be mounted at a distal-facing side of the display; (b) said light source S1 can be configured to selectively emit light in a first selected narrow wavelength band narrower that white light; (c). said narrow wavelength band can be configured to cause emission of fluorescent light from a location in the patient; (d) said camera FFC1 can be configured to image light associated with said narrow wavelength band; (e). said camera FFC1 can be configured to image fluorescence; (f) said camera FFC2 can be configured to image white light; (g) said camera FFC1 can be configured to image light associated with said narrow wavelength band and has lower spatial resolution but higher sensitivity than said camera FFC2. said camera FFC1 can include a first electrically controlled color filter configured to selectively switch between light in a selected color and white light; (j) said camera FFC1 can be configured to image light associated with said narrow wavelength band, said camera FFC2 can be configured to image white light, and said display can be configured to superimpose spatially registered images taken with the cameras FFC1 and FFC2; (k). both cameras FFC1 and FFC2 can image white light and can be spaced from each other for a stereo view of the patient's cervix; (l) both cameras FFC1 and FFC2 can be configured to image light in a selected narrow wavelength band that is narrower than white light and can be spaced from each other for a stereo view; (m) both cameras FFC1 and FFC2 can be configured to image fluorescence and are spaced from each other for a stereo view; (n) the endoscopy camera at the distal end of the said single-use portion can comprise: a camera CamW that is configured to view a target in the patient and is responsive primarily to a wavelength range of white light; a second electrically controlled color filter configured to selectively operate in a mode A to pass light primarily in a wavelength range of white light or in a mode B to light primarily in (i) a second selected narrow wavelength band that is narrower than white light or (ii) fluorescence light; a forward-looking camera CamFA/B configured to view said target from a different angle and through said second color electrically controlled color filter; and wherein said processor is operatively coupled with said display and configured to: selectively switch said second color filter between mode A and mode B, and receive image data from said cameras CamW and Cam FA/B and: form a white light stereo image of the target when said filter is operating in mode A; form a selected narrow wavelength band image or a fluorescence light image from camera CamFA/B when said filter is operating in mode B; and form and display at said display a composite image as an overlay of the white light stereo image and the selected narrow wavelength band image or fluorescent light image from said cameras CamW and CamFA/B, (o) the single-use portion can extend along a longitudinal axis, the handle can extends along a handle axis transverse to the longitudinal axis, the interlocking mount of the reusable portion can have an upper portion that has an elongated, open slot extending along said longitudinal axis and the interlocking mount of the single use portion can comprise an elongated hub extending along the longitudinal axis and configured slide into and snap-lock to said slot to thereby form the assembled endoscope; (p) can the reusable portion include a manual bend controller mounted at a proximal end thereof and said single-use portion can include a bending mechanism that automatically engages said manual bend controller when the single-use portion is snapped into said slot and responds to manual operation of the bend controller to selectively bend the distal portion of the cannula; (q) said cannula can be configured to rotate relative to the reusable portion; and (r) said camera CamFA/B can have a lower spatial resolution than said camera CamW at least when said second color filter is operating in said mode B.

According to some embodiments, a medical endoscopy/stereo colposcopy instrument comprises: an L-shaped reusable portion comprising a downwardly extending handle and an axially extending housing; a single-use portion comprising a hub removably secured to a proximal end of the housing and a cannula extending distally from the hub; wherein: one of said housing and hub comprises a mounting formed as an axially extending slot and the other comprises a mounting in the form of an axially extending rail configured to slide into the slot in the proximal direction and thereby removably secure the hub and cannula to the handle portion; said proximal portion of the handle portion comprises an opening and said hub and cannula comprise a bending mechanism that is configured to bend a distal portion of the cannula and includes a proximally extending thumb lever that passes through said opening and protrudes proximally from the handle portion when the hub and handle portion are secured to each other and manual action on said thumb lever controls bending of said distal portion of the cannula; an endoscopy camera module at the distal portion of the cannula; a colposcopy camera module mounted to the housing and comprising colposcopy cameras FFC1 and FFC2 configured to view a target from different viewpoints; and a display operatively coupled with the endoscopy camera module and to the colposcopy camera module to receive image data therefrom and display images based on the received image data.

According to some embodiments, a medical device for imaging fluorescence from a patient's cervix comprises: a cup-shaped housing containing a light source configured to cause fluorescence from a selected portion of the cervix when the housing is at treatment position relative to the cervix; a camera CamF1 mounted to the housing and configured to image fluorescence from the cervix from a first viewpoint and provide first image data; and a display operatively coupled with the camera CamF and configured to display a first fluorescence image derived from said first image data.

The device described in the immediately preceding paragraph can further comprise a camera CamF2 also mounted to said housing and configured to image fluorescence from the cervix from a second viewpoint and provide second image data, wherein said display can be coupled with the camera CamF2 to display a second fluorescence image derived from the second image data.

According to some embodiments, a method of imaging a patient comprises: taking stereo colposcopy images of a patient's cervix with cameras FFC1 and FFC2 mounted to a reusable portion to which a display is mounted; taking endoscopy images of the patient's bladder or uterus with a single use portion that is removably coupled with the reusable portion to form an assembled endoscope and has at a distal end a camera CamW taking white light images and/or CamF taking images in a narrower wavelength band or fluorescence images; and displaying said colposcopy images and said endoscopy images at said display.

According to some embodiments, the taking of endoscopy images in said method can comprise taking images with both cameras CamW and CamF and the displaying can comprise displaying a spatially registered superposition of the images from cameras CamW and CamF.

According to some embodiment, a medical endoscopy/colposcopy instrument comprises: a reusable portion that includes a handle configured to be grasped by a user's hand and a display mounted to the reusable portion; a forward-facing colposcopy imaging and lighting system mounted to said reusable portion; a single-use portion comprising a cannula configured for insertion in the patient and having an endoscopy imaging and lighting system at a distal end of the cannula; interlocking mounts at a proximal end of the single-use portion and at the reusable portion, configured to releasably couple the reusable and single-use portions to each other to thereby form an assembled endoscope configured to take endoscopy images with said endoscopic imaging and lighting system; and a processor configured to process the image data from the colposcopy and/or endoscopy imaging and lighting system into display images and to cause said display to show said display images.

According to some embodiments, the instrument described in the immediately preceding paragraph can further comprise one or more of the following features: (a) the colposcopy imaging and lighting system can comprise a single colposcopy camera FFC1 and a colposcopy source S1 to provide a two-dimensional view; and (b) the colposcopy imaging and lighting system further comprises a second colposcopy camera FFC2 spaced from said camera FFC1 for a stereo view and a second colposcopy source S2.

BRIEF DESCRIPTION OF THE DRAWINGS

To further clarify the above and other advantages and features of the subject matter of this patent specification, specific examples of embodiments thereof are illustrated in the appended drawings. It should be appreciated that these drawings depict only illustrative embodiments and are therefore not to be considered limiting of the scope of this patent specification or the appended claims. The subject matter hereof will be described and explained with additional specificity and detail through the use of the accompanying drawings in which:

FIGS. 2A and 2B are perspective views of a portable and ergonomic endoscope with disposable cannula, according to some embodiments;

FIG. 10 is a perspective view in which a combined, spatially registered image displayed to a user on an endoscopy system, according to some embodiments.

FIG. 18 is an exploded perspective view of an endoscope, according to some embodiments.

FIG. 25 is a perspective view like that of FIG. 24 but from a different viewpoint, according to some embodiments.

FIG. 32 is a flow chart illustrating an example of sequences of steps in using an instrument with both endoscopy and colposcopy functionalities, according to some embodiments.

DETAILED DESCRIPTION

Figure 1A:
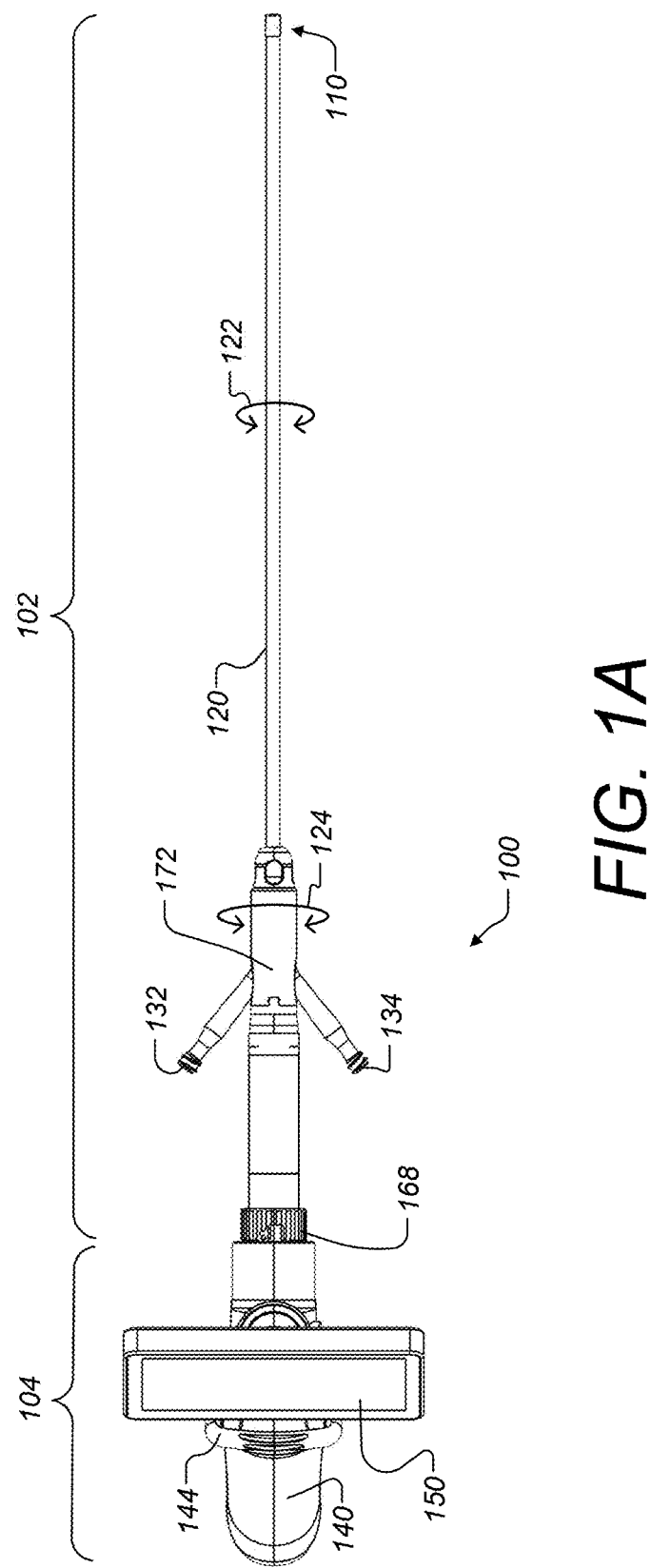
FIGS. 1A, 1B and 10 are side, top and rear views of a portable and ergonomic endoscope with disposable cannula, according to some embodiments.

A detailed description of examples of preferred embodiments is provided below. While several embodiments are described, the new subject matter described in this patent specification is not limited to any one embodiment or combination of embodiments described herein, but instead encompasses numerous alternatives, modifications, and equivalents. In addition, while numerous specific details are set forth in the following description to provide a thorough understanding, some embodiments can be practiced without some or all these details. Moreover, for the purpose of clarity, certain technical material that is known in the related art has not been described in detail to avoid unnecessarily obscuring the new subject matter described herein. It should be clear that individual features of one or several of the specific embodiments described herein can be used in combination with features of other described embodiments or with other features. Further, like reference numbers and designations in the various drawings indicate like elements.

This patent specification describes an endoscope with various imaging functionalities under the heading ENDOSCOPY EXAMPLES. Under the heading ENDOSCOPY/STEREO COLPOSCOPY AND OTHER EXAMPLES, the specification describes various functionality examples that include endoscopy, colposcopy, facial recognition and monitoring therapies such as photodynamic therapy of the cervix with a device held at the cervix for extended periods.

ENDOSCOPY EXAMPLES

According to some embodiments, a portable ergonomic endoscope system is described that includes an imaging system with at least two separate cameras and at least two separate light sources. The camera and light sources are configured to be used to simultaneously image a target object (e.g. tissue). By employing different illuminations, different filters and manipulating the spectral responses, different characteristics of the target object can be captured. According to some embodiments, a system processor can coordinate the cameras, the light sources and combine the resulting images to display to an operator an enhanced combined image of the object. According to some embodiments, the system can be configured to perform NBI (Narrow Band Imaging) imaging. According to some embodiments, the system can also be configured to perform Fluorescence Imaging.

As used herein, the term Color Filter Array (CFA) refers to a filter placed on top of a pixel to allow a certain bandwidth(s) to pass. Regular consumer cameras such as the cell phone camera uses RGB CFA. For other special applications, special CFAs can be designed.

As used herein, the term Narrow-band imaging (NBI) refers to a color imaging technique for endoscopic diagnostic medical tests, where light of specific blue and green wavelengths is used to enhance the detail of certain aspects of the surface of the mucosa. According to some embodiments, a special filter can be electronically activated by a switch in the endoscope leading to the use of ambient light preferably of wavelengths at or close to 415 nm (blue) and 540 nm (green). Because the peak light absorption of hemoglobin occurs at these wavelengths, blood vessels will appear very dark, allowing for their improved visibility and for the improved identification of other surface structures.

As used herein, the term Fluorescence Imaging (FI) refers to fluorescence imaging, sometimes using fluorescent dyes, to mark, highlight or enhance certain biological mechanisms and/or structures. Fluorescence itself, is a form of luminescence that results from matter emitting light of a certain wavelength after absorbing electromagnetic radiation. In a selected narrow wavelength band light endoscopy, for example, fluorescent dyes (Hexvix) are injected in the bladder. Then a selected narrow wavelength band light (around 405 nm) is used to illuminate the tissue with Hexvix which emits fluorescence of wavelength of about 610 nm. Note that with FI, the camera visualizes the fluorescence emitted from within the object, while with NBI the camera visualizes the reflections of various bandwidths of light by the object.

According to some embodiments, a novel dual camera and dual light source (DCDL) system is described for multi-spectral or multi-color imaging. Embodiments of surgical applications are disclosed with simultaneous white light, fluorescence and infrared images.

The described methodologies apply to general multi-spectral multi-band imaging. According to some embodiments, an endoscopy system is described that includes two separate camera/LED systems that are integrated into the same cannula or endoscope. A white light camera, referred to as CamW, is paired with white light LED, referred to as LightW. A fluorescence camera, referred to as CamF is paired with a selected narrow wavelength band light LEDs, referred to as LightC. In this configuration, CamF is used as IR Camera when either or both LightC, LightW are off.

According to some embodiments, CamW is optimized for white light endoscopy, where strong and optimal white LEDs are used to illuminate the object, such that high image resolution can be achieved. CamF is optimized for sensitivity, because typically a fluorescence light source is weak. To maximize sensitivity and signal to noise of the CMOS sensor pixels for high quality imaging, the following are implemented:

According to some embodiments, a special color filter array (CFA) on the pixel array is used (shown in FIG. 7), such that the CMOS sensor array is sensitive to red or IR spectrum (near 600 nm or higher). According to some embodiments, to further improve sensitivity, preferably relatively large pixels (for example 2.2 um×2.2 um) are used for the CMOS sensor of CamF. In such cases, CamF preferably has lower spatial resolution than CamW pixels (for example, 1.75 um×1.75 um or 1.0 um×1.0 um) but much higher sensitivity.

Figure 1B:
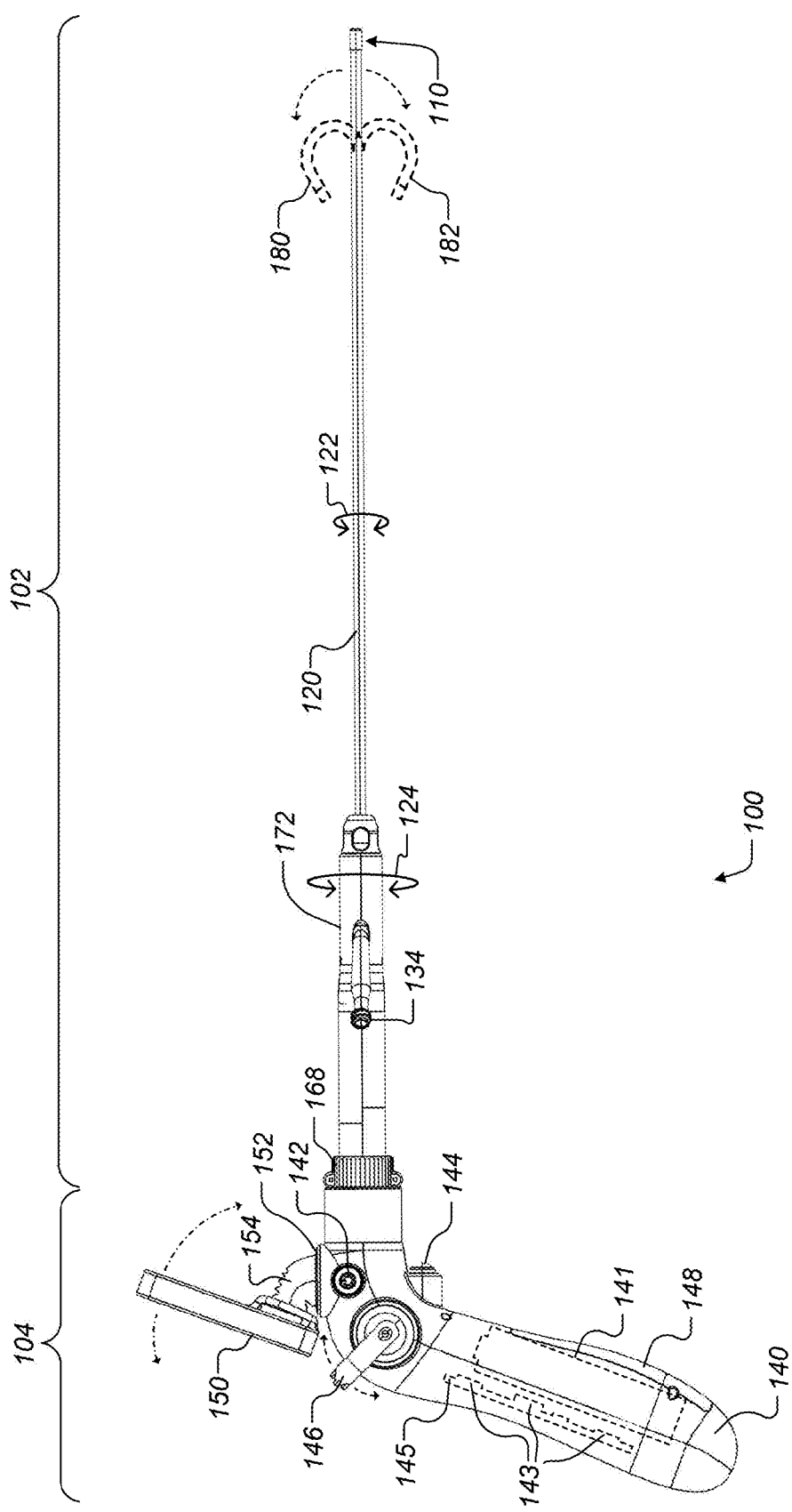
Figure 1C:
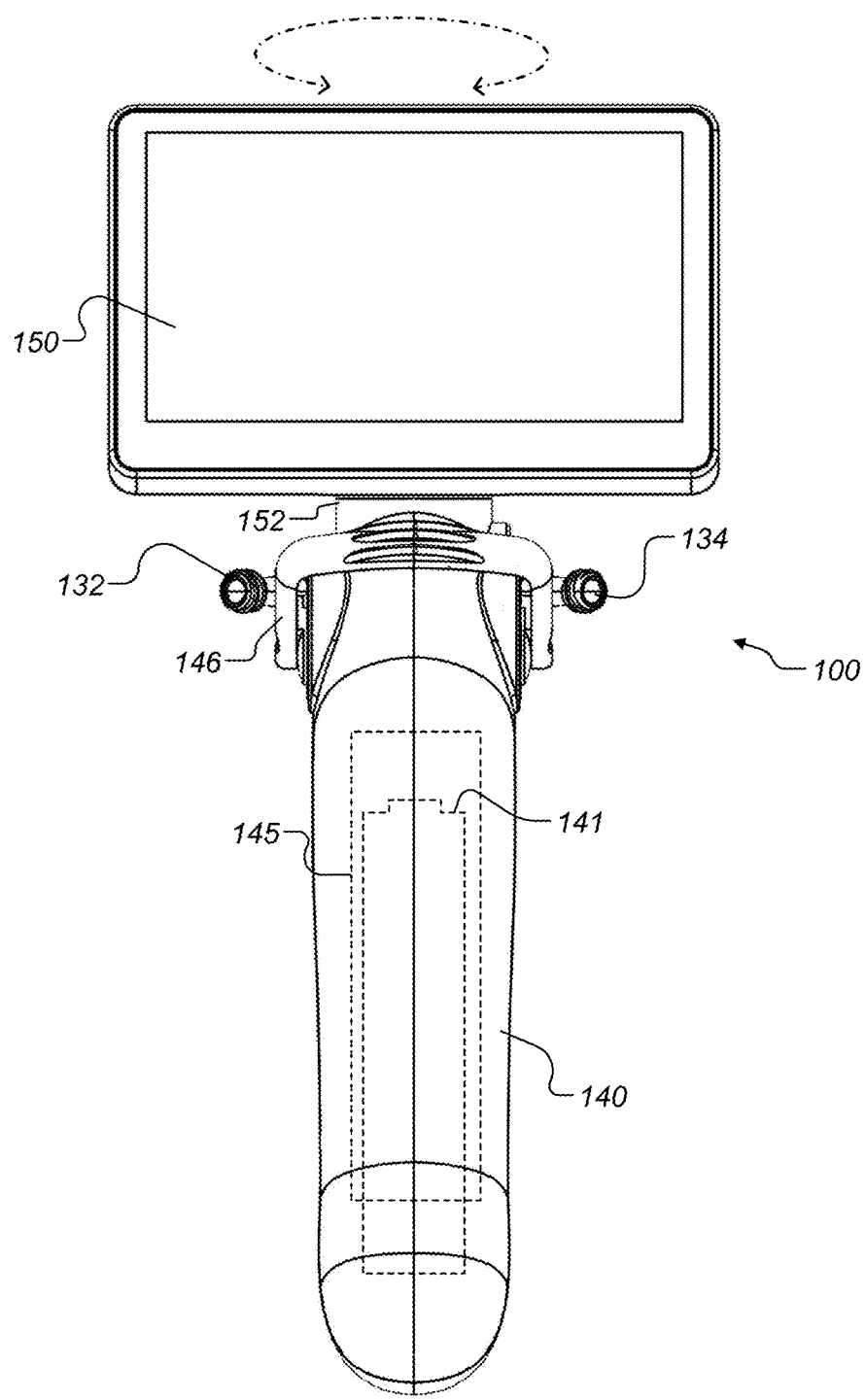

FIGS. 1A, 1B and 1C are side, top and rear views of a portable and ergonomic endoscope with disposable cannula, according to some embodiments. System 100 is adapted for easy and quick use with minimized patient discomfort and high placement accuracy. System 100 is made up of a disposable, or single-use portion 102 and a re-usable portion 104. The two portions 102 and 104 can be mated and un-mated with each other via connectors as will be shown and discussed infra in further detail. Cannula 120 has an imaging and illumination modules on its distal tip 110. An electrical cable (not shown) is positioned within the cannula and supplies control signals and power to the camera and LED illumination modules on distal tip 110 and also transmits video image data from the camera module to the hand piece 140 and display 150 for viewing by an operator. In the example shown, hand piece 140 includes two control buttons 142 and 144 which can be configured for power on/off and image capture, respectively. According to some embodiments, hand piece 140 is shaped as a pistol grip as shown and includes a rechargeable battery 141 that is accessible via battery door 148. According to some embodiments, battery 141 is an lithium-ion rechargeable battery such as type 18650 or 26650. Also housed within handle 140 are electronics modules 143 mounted on printed circuit board (PCB) 145. Electronics modules 143 and PCB 145 are configured to carry out various processes such as video processing and capture, wi-fi transmission of data to external devices, lighting control, user interface processing, and diagnostics. Electronic modules 143 also are configured to include at least one non-volatile memory module for storing captured video and images from the camera module. According to some embodiments, display 150 can both tilt and swivel to provide optimal viewing angle for the operator. Swivel joint 152 is configured to provide swiveling of display 150 as shown by the dash dot arrow in FIG. 10, and hinge joint 154 is configured to provide tilting of display 150 as shown by the dash dot arrows in FIG. 1B. According to some embodiments, the hinge joint is configured to allow for tilting of display in the distal direction of about 90 degrees, or nearly 90 degrees. Such tilting can be useful, for example, when give the operator an unobstructed or less obstructed view. Handle 140 also includes a thumb lever 146 that can be moved upwards or downwards as shown by the dashed arrows. Moving the thumb lever 146 upwards and downwards causes the distal tip 110 to bend upwards and downwards, respectively, as shown by dashed outlines 180 and 182, respectively. Further details of the operation of thumb lever 146 to control the steering of distal tip 110 and cannula 120 is provided in U.S. patent application Ser. No. 17/362,043 filed Jun. 29, 2021, incorporated by reference herein, which is referred to herein as "the '043 Application."

The cannula 120 is connected proximally to a fluid hub 172 including in this example two fluid ports 132 and 134. Proximal to the fluid hub is a collar 168. According to some embodiments, the collar 168 is configured to rotate so as to allow for a "plug and twist lock" style mating of portions 102 and 104, as will be shown and described in further detail infra. According to some embodiments, at least a portion of fluid hub 172, along with cannula 120 and distal tip 110, are manually rotatable relative to handle 140 along the main longitudinal axis of cannula 120, as shown by solid arrow 124. Thus, rotating the rotatable portion of hub 172 causes rotation of cannula 120 and distal tip 110 as shown by solid arrow 122. According to some embodiments, the combination of rotating cannula 120 and 110 and moving the thumb lever 146, the user can "steer" the direction of distal tip 110 as desired. According to some embodiments, the cannula 120 has a preferred working length of roughly 12 inches but shorter or longer lengths can be used depending on the medical application, and a preferred outer diameter of 5.5 to 6.5 inches but again a greater or a lesser diameter can her used depending on the medical application and developments in camera and illumination technology.

Figure 2B:
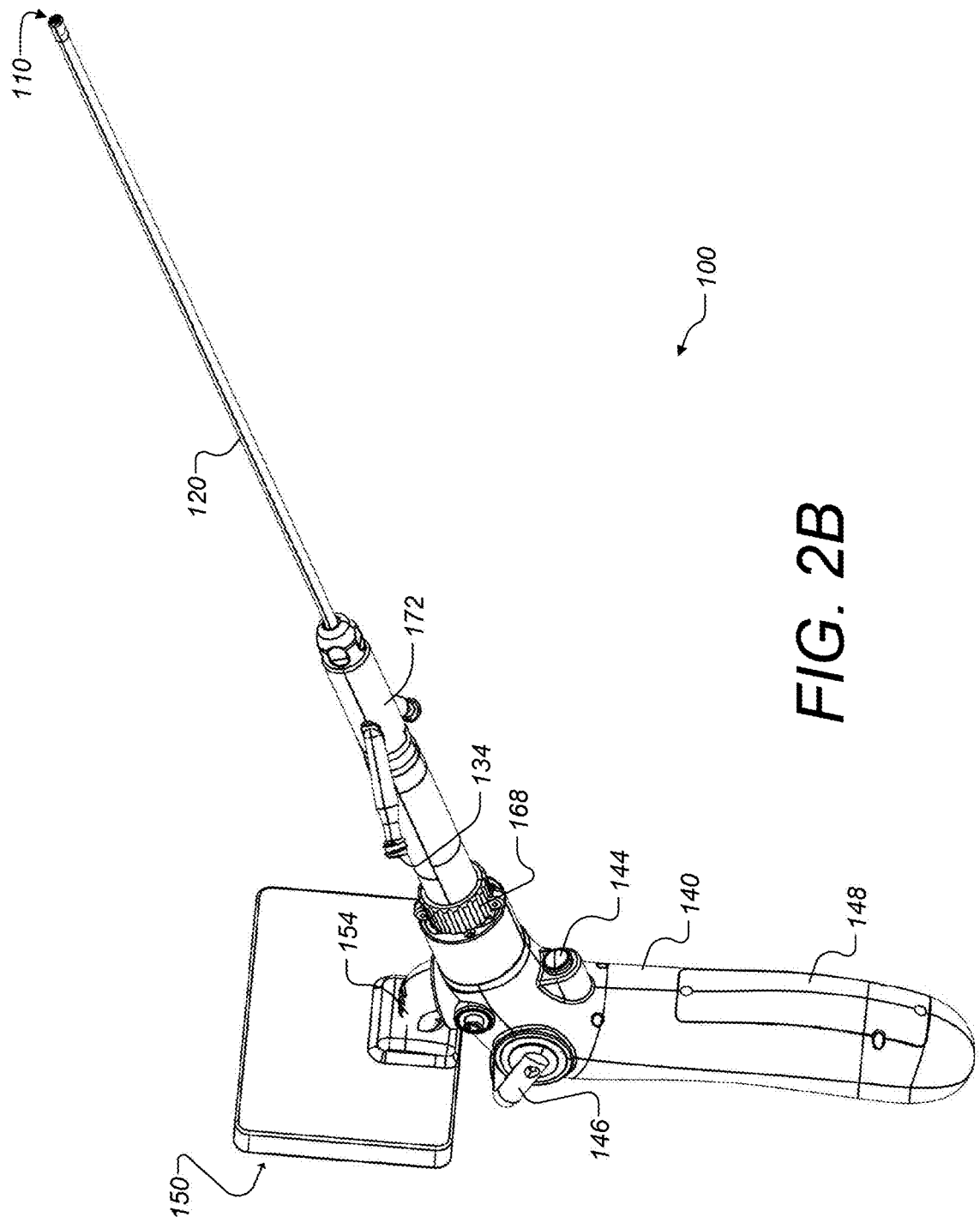

FIGS. 2A and 2B are perspective views of a portable and ergonomic endoscope with disposable cannula, according to some embodiments. FIG. 2A shows a syringe 230 used to supply fluid, such as saline, through a fluid lumen (not shown) within cannula 120 via tubing 232, connector 234 and fluid port 134. According to some embodiments the cannula 120 is semi-rigid. The cannula 120 is stiff enough so it does not collapse with longitudinal pushing and pulling forces expected in a medical procedure for which it is intended. On the other hand, cannula 120 is flexible enough such that it can bend while it passes through curved anatomy.

Figure 3A:
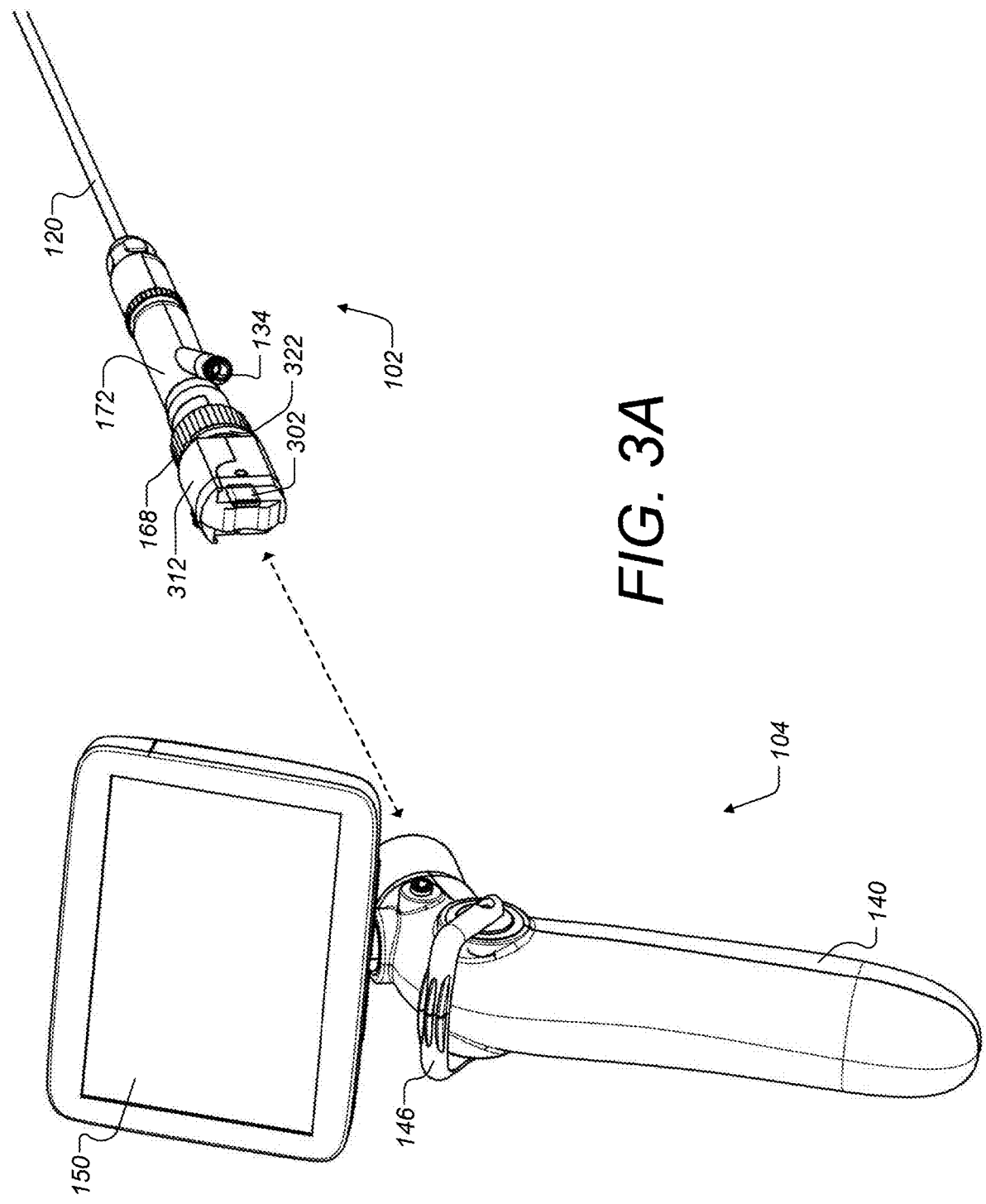
FIGS. 3A-3B are perspective views that illustrate the mating and un-mating of reusable and disposable portions of a portable and ergonomic endoscope, according to some embodiments.
Figure 3B:
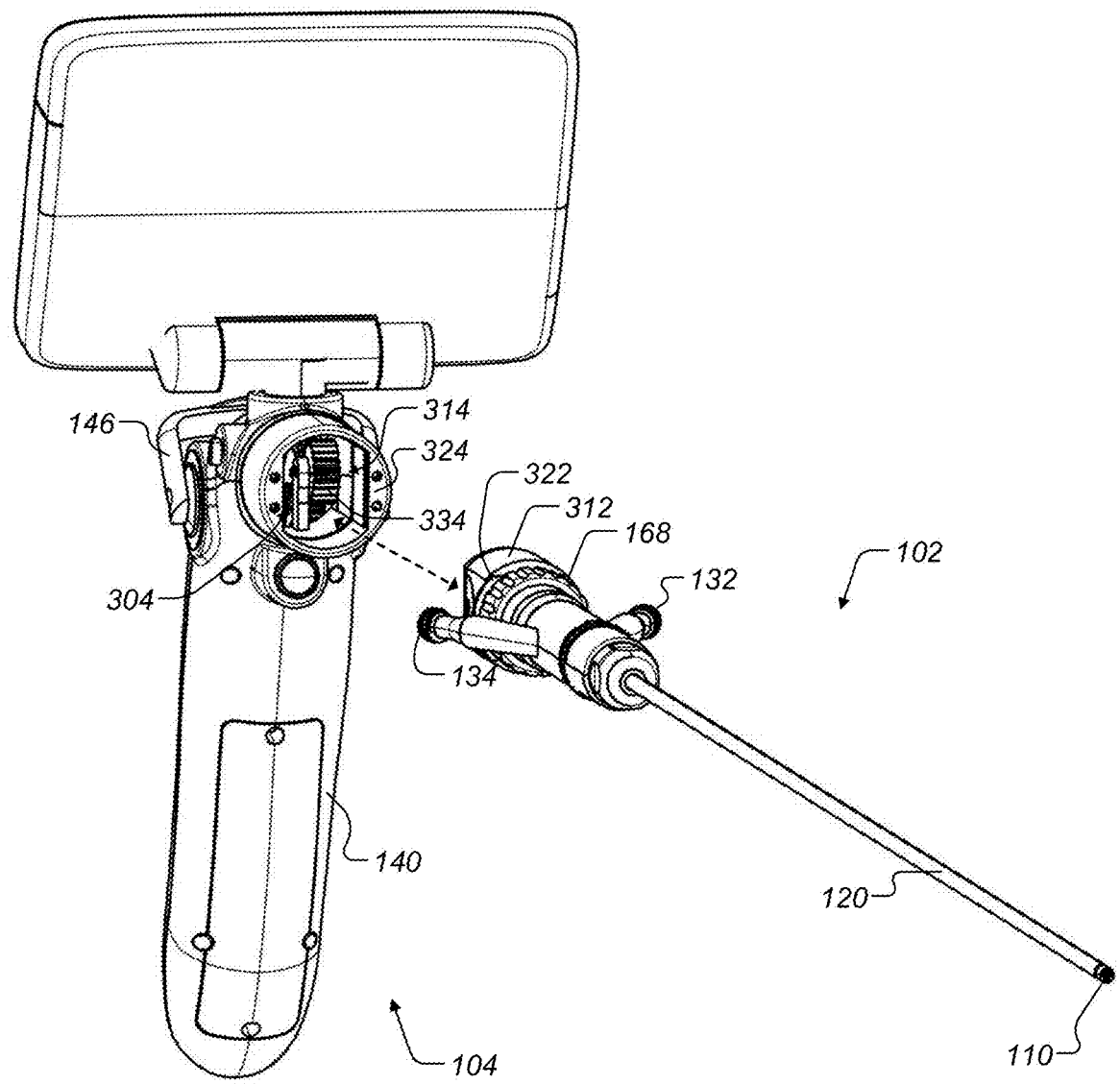

FIGS. 3A-3B are perspective views that illustrate the mating and un-mating of reusable and disposable portions of a portable and ergonomic endoscope, according to some embodiments. The portions 102 and 104 are connectable and separable via a mechanical and electrical connector. The electrical connection is made via a USB-C type plug 302 on single-use portion 102 (visible in FIG. 3A) and USB-C type receptacle 304 on multiple use portion 104 (FIG. 3B). The mechanical connection includes both a structural connection to fixedly attach portions 102 and 104 as well as a steering connection, through which steering input from the steering structure in the re-usable portion 104 can be relayed to the steering components in the single-use portion 102. The structural connection, in this example, includes a male rounded portion 312 on single-use portion 102 that is shaped to fit snugly into a female socket 314 on multiple-use portion 104. The structural connection also includes a twist lock type mechanism wherein a male portion 322 can be inserted past a female opening 324 and then locked by twisting the male portion 322 approximately one quarter turn (90 degrees). The twisting action can be applied manually via textured or knurled ring collar 168. In this way, the connection can be configured as a "plug and twist" type connection. The steering connection is provided by meshing the transmission gear 334 on the multiple-use portion 104 with the passive gear 332 on the single-use portion 102.

Figure 4A:
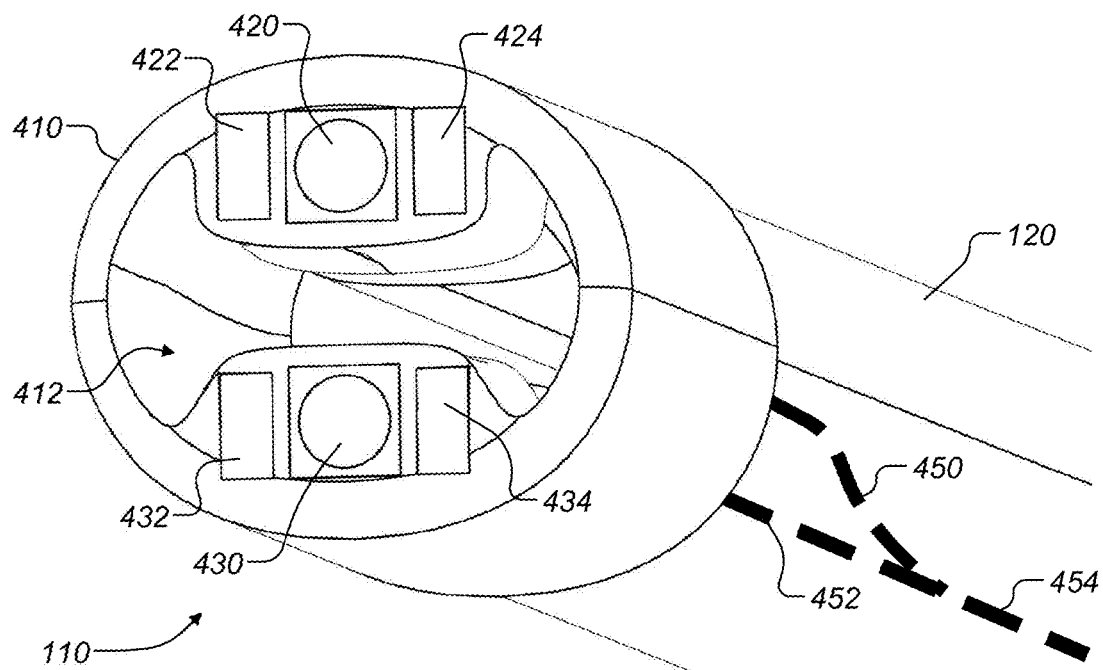
FIGS. 4A and 4B are a perspective and a schematic view of a distal tip including multiple camera and lighting modules used with a portable and ergonomic endoscope, according to some embodiments.
Figure 4B:
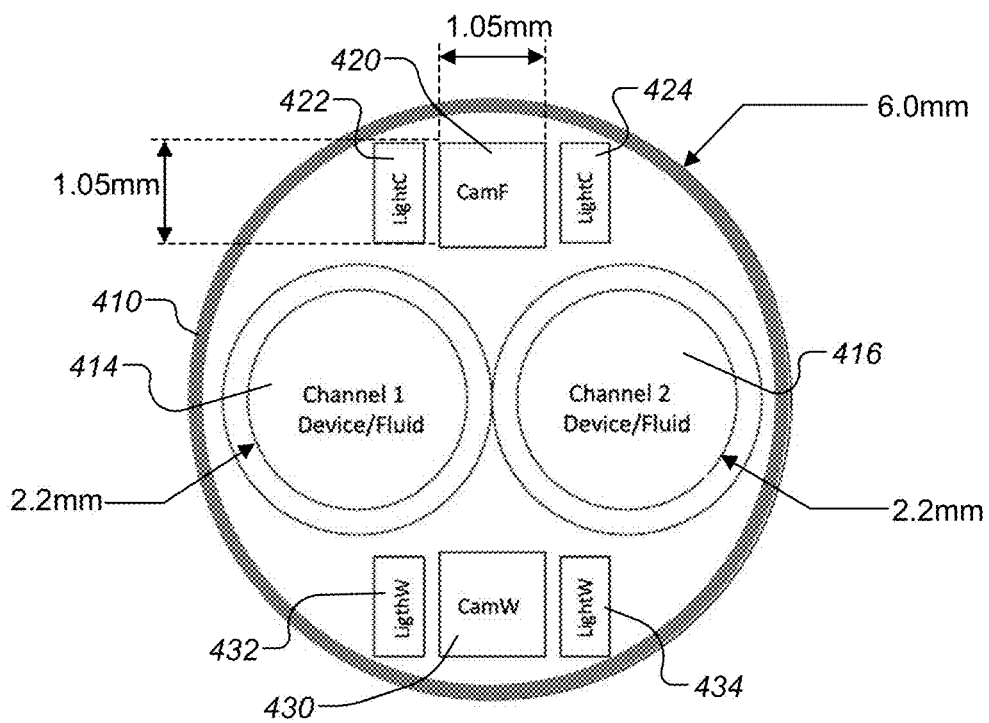

FIGS. 4A and 4B are a perspective and schematic view of a distal tip including multiple camera and lighting modules used with a portable and ergonomic endoscope, according to some embodiments. In FIG. 4A, the distal tip 110 is shown attached to the distal end of cannula 120. According to some embodiments, tip 110 includes a housing piece 410 that is molded separately from and bonded to the distal end of cannula 120. Housed within housing 410 are two camera modules: CamF module 420 and CamW module 430. Each of the CamF 420 and CamW 430 modules includes a lens and sensor. The sensors for each CamF 420 and CamW 430 include a color sensor, color filter array, and electronics and circuitry as will be described in further detail, infra. On either side of CamF module 420 are two selected narrow wavelength band LEDs 422 and 424 configured to emit excitation light suitable for fluorescence endoscopy. In some examples, LEDs 422 and 424 are configured to emit light at about 410 nm (violet-blue). On either side of CamW module 430 are two white LEDs 430 and 434 configured to emit white light suitable for visible white light endoscopy. Also shown in FIG. 4A is port 412 that is configured to provide fluid (flowing either into or out of the patient) and/or provide an opening through which a tool or other device can pass (e.g. a needle). Note that although FIG. 4A shows a total of four LEDs (two white and two selected narrow wavelength band), in general, other numbers of LEDs may be provided according to factors such as desired lighting quality, endoscope size, and LED characteristics such as size and brightness. In some embodiments three or fewer LEDs can be provided and in some embodiments 10 or more LEDs can be provided. Furthermore, the number of white and wavelength band LEDs does not have to be equal, but also will depend on various factors. The LED set can be 3, 4 or more. Other light sources can be substituted, such as optic fibers that deliver light generated elsewhere.

In FIG. 4B, the example shown includes two separate device/fluid channels 414 and 416. In this case, both have an inner diameter of 2.2 mm. According to some embodiments, channel 414 can be connected to fluid port 134 (shown in FIG. 1A) while channel 416 is connected to fluid port 132 (also shown in FIG. 1A). According to some embodiments, to boost sensitivity to fluorescence the CMOS sensor of CamF 420 is configured with larger pixels than CamW 430. For example, the CamF pixels can be 2.2 um×2.2 um arranged in a 400×400 matrix size, while the CamW pixels are 1.0 um×1.0 um or 1.75 um×1.75 um and arranged in higher spatial resolution matrix size. Because white LEDs tend to be relatively strong, the CamW 430 module can include a CMOS sensor with smaller pixels, such as 1.75 um×1.75 um or 1 um×1 um, so higher spatial resolutions can be achieved with up to 720×720 matrix size or larger.

Figure 7:
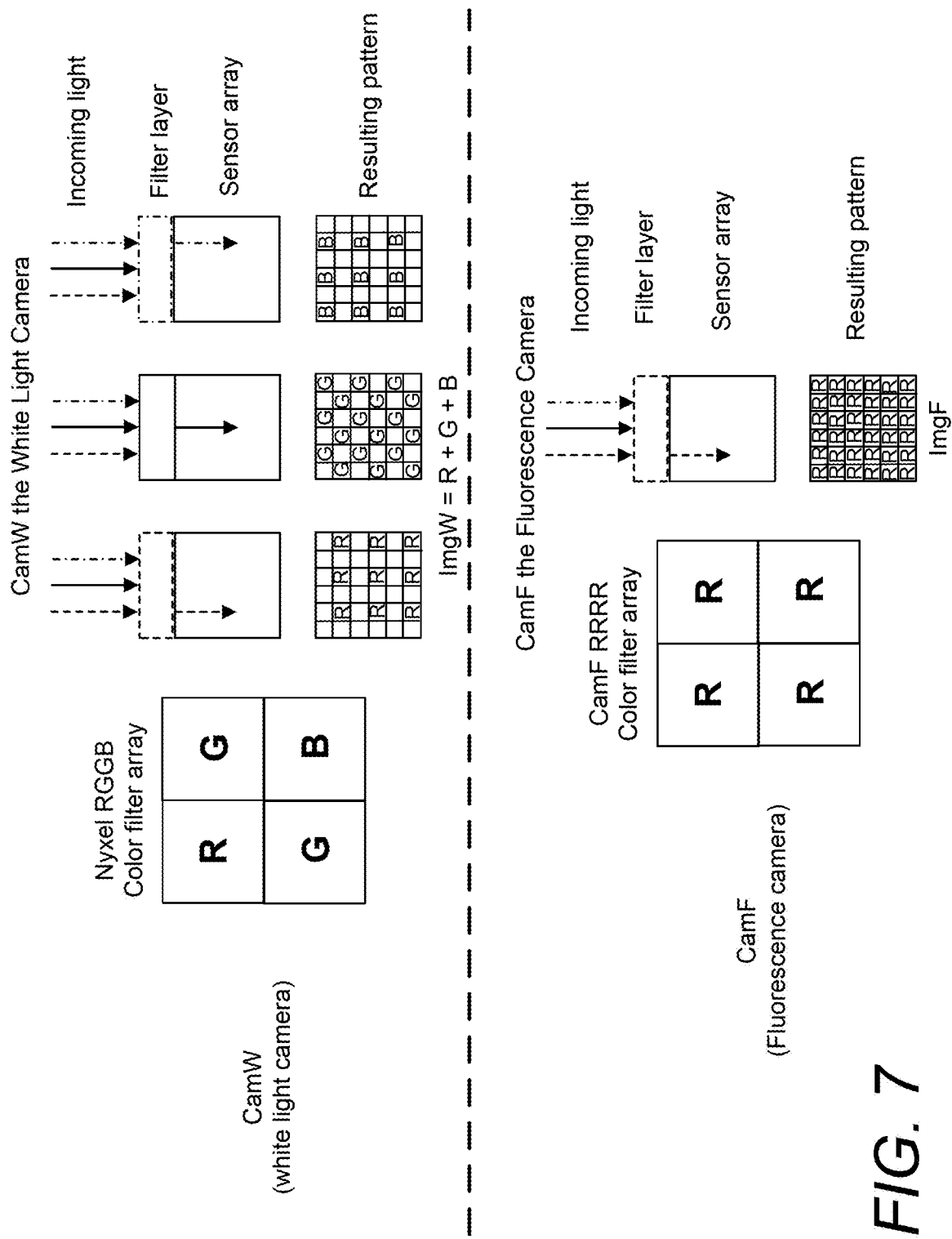
FIG. 7 is a diagram illustrating possible color filter array configurations for a dual camera dual light source system for multi-spectral imaging and surgical applications, according to some embodiments.

According to some embodiments, CamF 420 is used for a selected narrow wavelength band light endoscopy, with partial CFA. An example is shown in FIG. 7 where only R Filters are used so that blue light and green light are filtered out and the majority of light that reaches the sensor is red. According to some embodiments, an IR camera is used as CamF.

Figure 5:
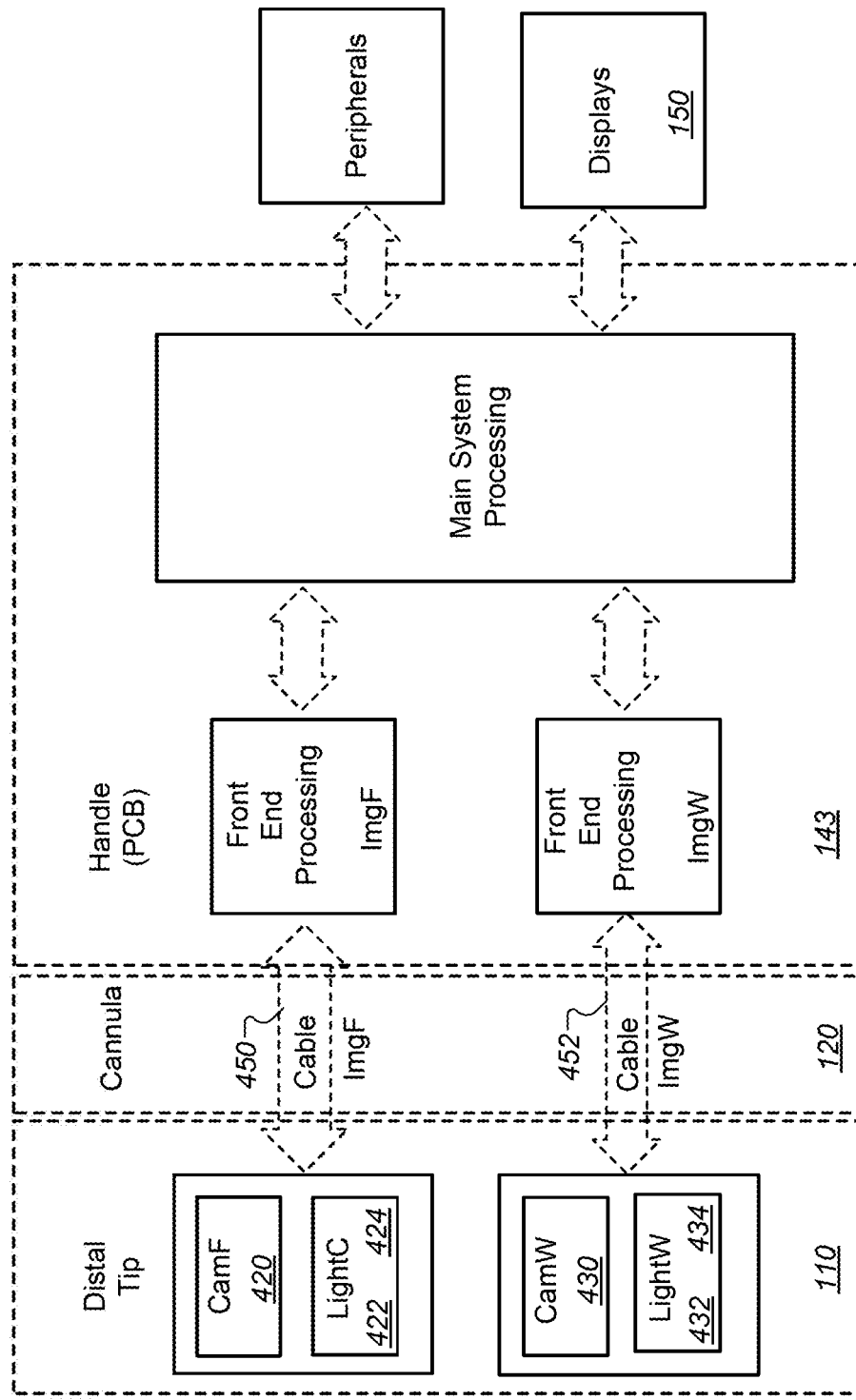
FIG. 5 is a schematic diagram of a dual camera dual light source system for multi-spectral imaging and surgical applications, according to some embodiments.

FIG. 5 is a schematic diagram of a dual camera dual light source system for multi-spectral imaging and surgical applications, according to some embodiments. As shown the distal tip 110 includes the camera and lighting modules, namely CamF, LightC, CamW and LightW. CamF camera 420 is configured for capturing images of a particular color or bandwidth, such as fluorescence with a narrow band centered around 610 nm. Filters for CamF 420 are designed to block incoming light at other wavelengths, for example by using a specially designed CFA array. CamF can be used for either NBI or FI depending on the particular application. LightC light source (422 and 424) for CamF 420, can be the excitation light in case of fluorescence imaging or simply blue or green light in the case of NBI. LEDs or special light sources can be used. According to some embodiments, CamW 430 is regular white light camera such as the camera of a cell phone. A typical RGB CFA can be used and in addition an IR filter can also be used. Typically an IR filter that filters out 50% of wavelength above 650 nm can be used. LightW (432 and 434), the light source for CamW, can be LED lights with various color tones close to white day light. The cannula 120 includes cables 450 and 452. ImgF refers to the image captured by CamF, and may be fluorescence or, in the case of NBI, reflections of green or blue lights. ImgW refers to the image captured by CamW, which maybe fluorescence or, in the case of NBI, reflections of green or blue lights.

Because the endoscope has two cameras that can operate at the same time and with different combination of lighting such as LightC, LightW (or another light band) the system takes advantage of having two "eyes" looking at the same target but seeing different aspects of the target at the same time and thus extracting more information from or about the object and targets. For example, when blue light is on, CamF would see mostly fluorescent emission by CamW sees at the same time reflection (that can be very strong) of LightC from the object and a little bit of fluorescence. As the two cameras are in sync and also spatially registered relative to each other, composite information of different kinds is delivered to the user to improve the clinical experience over the case of seeing only one of the two kinds of information about the object or target.

According to some embodiments, Nyxel technology can be used which has been developed by OmniVision. Nyxel pixels can be used for CamF 420 and have significantly improved pixel sensitivity with sensitivity to red and near infrared bandwidth. This is particularly useful for detecting fluorescence around 610 nm.

In electronics modules 143, front end processing and main system processing is performed. According to some embodiments, the images are combined for display on display 150.

Figure 6:
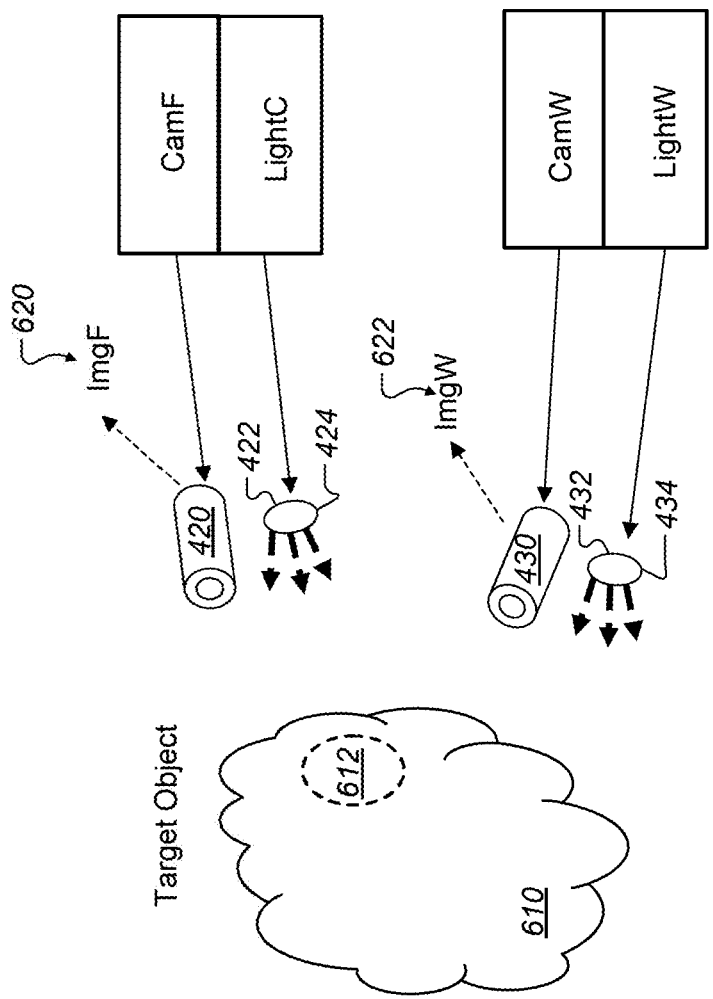
FIG. 6 is a conceptual diagram illustrating design aspects of a dual camera dual light source system for multi-spectral imaging and surgical applications, according to some embodiments.

FIG. 6 is a conceptual diagram illustrating design aspects of a dual camera dual light source system for multi-spectral imaging and surgical applications, according to some embodiments. In general, it is desirable to obtain multi-color or multi-spectral images of target objects such as human tissue. Typically, visible light images of the object plus images obtained by other color bands are used to better characterize the target tissue and shape. Two cameras (Cam F, CamW) are associated two light sources (LightC, LightW). CamF is an optical camera that is sensitive to certain color band, for example Red and IR. The output of CamF is ImgF. LightC is a light source (band C), other than white light. In Dual Band Imaging (DBI), LightC can be green or blue. In fluorescence imaging it can also be a light source that excites the object to fluorescence color. CamW is an optical camera that is sensitive to certain color band (B), for example the white light. The output of CamW is ImgW. LightW is a light source that emits certain color band B, for example the white light.

FIG. 7 is a diagram illustrating possible color filter array configurations for a dual camera dual light source system for multi-spectral imaging and surgical applications, according to some embodiments. According to some embodiments, CamF uses a Nyxel pixel (from Omnivision) and a "Red Only" filter array, the CamF RRRR filter. This arrangement allows for red and/or IR band to pass while filtering out the background blue and green light.

The CamF can achieve four times the resolution for red compared to that of Nyxel CFA or Old CFA, because one out of four pixels in Nyxel or Old CFA arrangements are used to capture red color. On the other hand, every pixel in CamF arrangement in FIG. 7 is used to capture red color.

Figure 8:
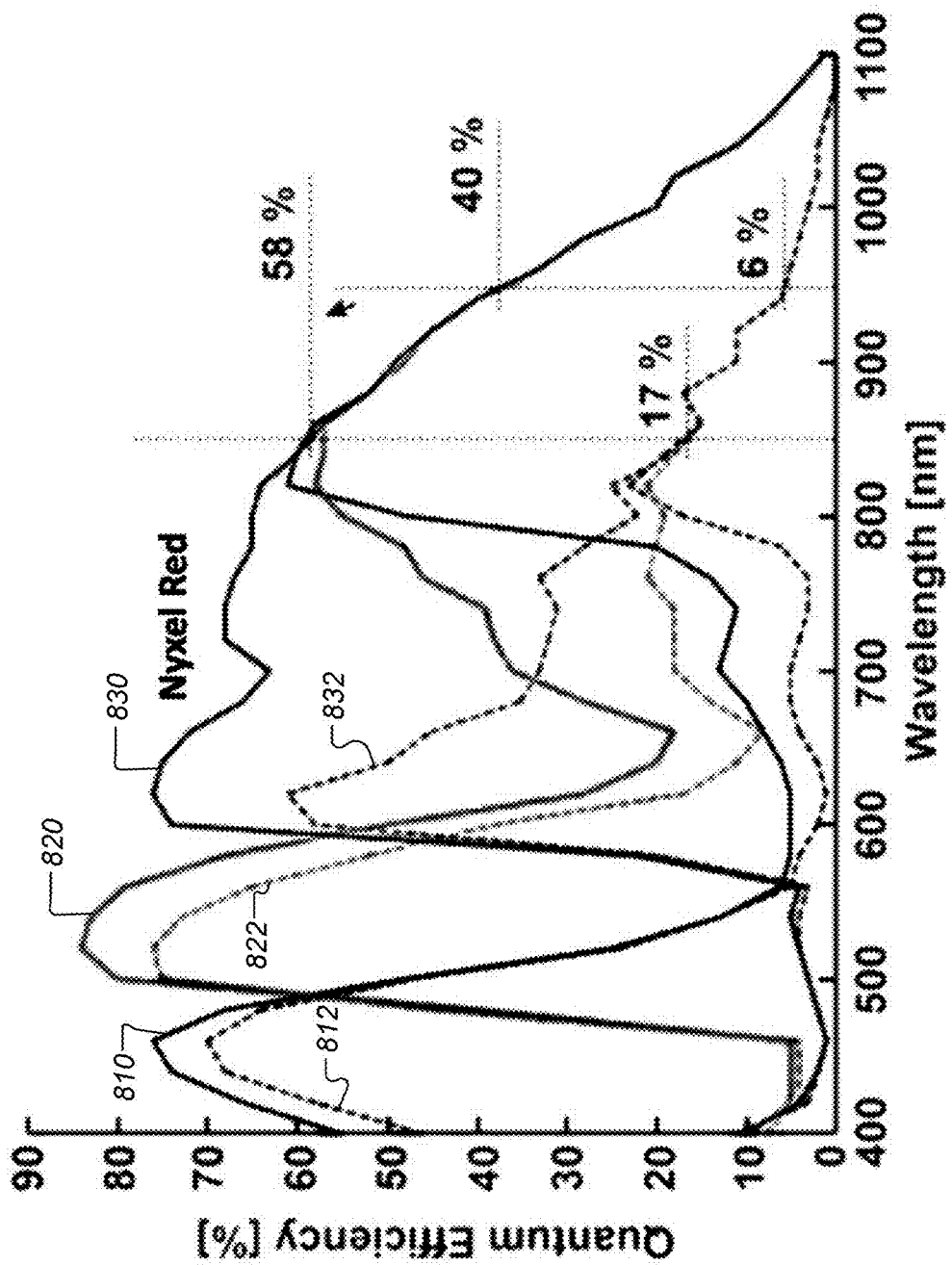
FIG. 8 is a plot showing quantum efficiency versus wavelength for Nyxel and conventional pixels.

FIG. 8 is a plot showing quantum efficiency versus wavelength for Nyxel and conventional pixels. In this figure, quantum efficiency is shown the new sensor developed by OminiVision, the Nyxel pixel. Curve 810 is a Nyxel blue pixel. Curve 812 is a conventional blue pixel. Curve 820 is a Nyxel green pixel. Curve 822 is a conventions green pixel. Curve 830 is a Nyxel red pixel. Curve 832 is conventional red pixel. It can be seen especially curves 830 and 832 that the Nyxel red pixel has a significantly higher sensitivity to the red or IR band than the regular conventional red pixel.

Figure 9:
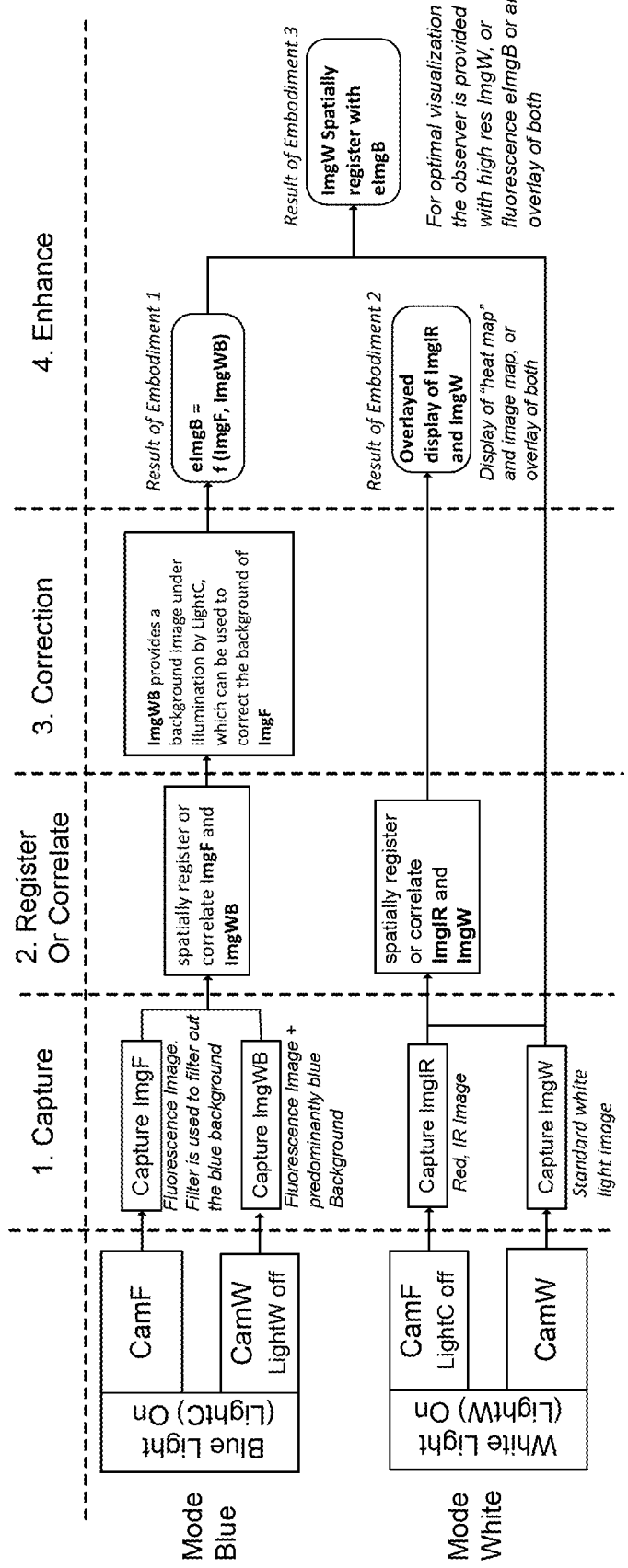
FIG. 9 is a diagram illustrating further aspects of combining multi-band image data from a dual camera dual light source system, according to some embodiments.

FIG. 9 is a diagram illustrating further aspects of combining multi-band image data from a dual camera dual light source system, according to some embodiments. With the availability of global shutter capability CamF, CamW can capture image frames under different combinations of LightC and LightW being turned "on" or "off." In "Surgical Embodiment 1" with the LightC (blue light) "on" but the LightW "off", the resulting captured images are ImgF from CamF and ImgWB from CamW. ImgF and ImgWB are spatially registered or correlated. This can be done due to the short time lag (or completely in sync when both cameras capture simultaneously) between images captured by the different cameras. ImgWB provides a background image under illumination by LightC, which can be used to correct the background of ImgF. The ImgF data combined with ImgWB when only LightC is on produces "eImgB."

In the case of Blue Light Endoscopy, ImgF has low signal to noise ratio (due to weak fluorescence signal), therefore CMOS sensor with high signal to noise pixels is used. On the other hand, ImgW has high signal to noise (due to strong white light), therefore CMOS sensor with smaller pixels can be used to boost spatial resolution.

In "Surgical Embodiment 2" CamF is used to capture ImgIR with the LightC "off." CamW captures the standard white light image with LightW "on." In this case ImgIR provides a "heat map" of the target; it is useful when energy devices such as laser or RF are used for tissue modification. ImgIR can alert users of hot or cold spots. The ImgIR and ImgW data can be spatially registered or correlated, again, due to the short time lag (or no time lag) between images captured by the different cameras. ImgIR and ImgW can also be combined or overlayed to provide a precise location of the hot and cold spots. That is, the hot and cold spots can be viewed in the context of an ordinary standard white light image to provide the viewer with locational context of the hot and cold spots.

In "Surgical Embodiment 3" ImgW is combined with eImgB. By combining embodiments 1 and 2, the high quality eImgB data is spatially registered with the white light image ImgW. The observer is provided with high res ImgW, or fluorescence eImgB or an overlay of both. According to some embodiments, surgeons can employ images available to better visualize their targets. The fluorescence Image eImgB, the white light image ImgW and IR Image ImgIR and seamlessly switch between different visualization modes.

According to a fourth "Embodiment 4" (not shown in FIG. 9) with accumulation of clinical cases, artificial intelligence algorithm (or machine learning) can be designed for automated diagnosis.

Figure 10:
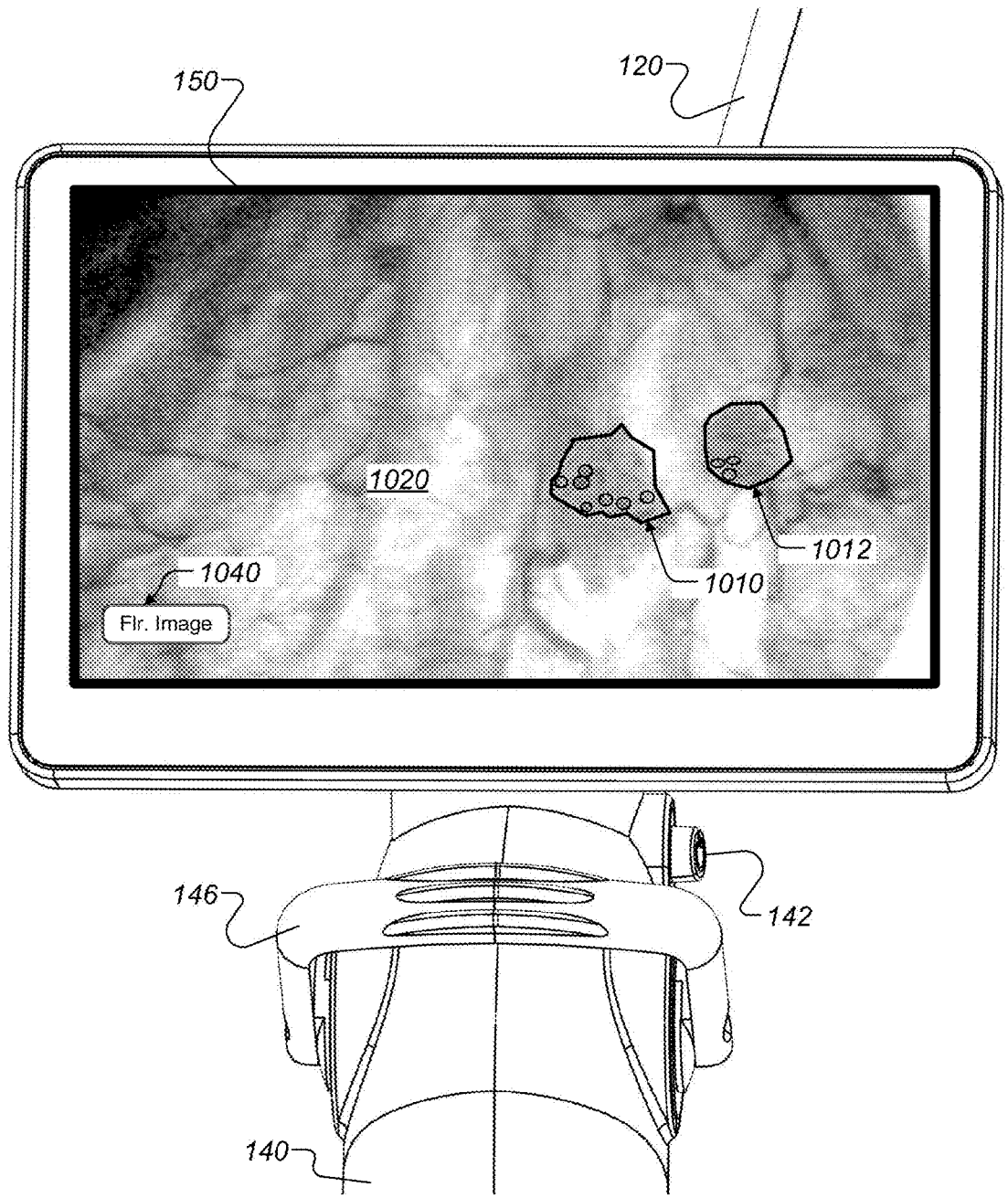

FIG. 10 is a perspective view in which a combined, spatially registered image is displayed to a user on an endoscopy system, according to some embodiments. In the displayed view, the ordinary white light image (ImgW) 1020 is displayed over most of the display screen 150. The example shown is "Embodiment 3" shown in FIG. 9, where the eImgB image is combined and spatially registered with the standard white color image (ImgW). In this case the regions 1010 and 1012 are obtained from the eImgB data and clearly show cancerous tumors. The operator can easily view the cancerous regions 1010 and 1012 in spatial registration with the ordinary color image of the surrounding tissue. This blending or combination provides a greatly enhanced view of the target tissue. According to some embodiments, the operator can easily switch between different modes (e.g. Embodiment 1, 2 or 3) by pressing a toggle button such as button 142, button 144 (shown in FIGS. 1B and 2B), or by a soft-button 1040 on touch-sensitive display 150.

Figure 11:
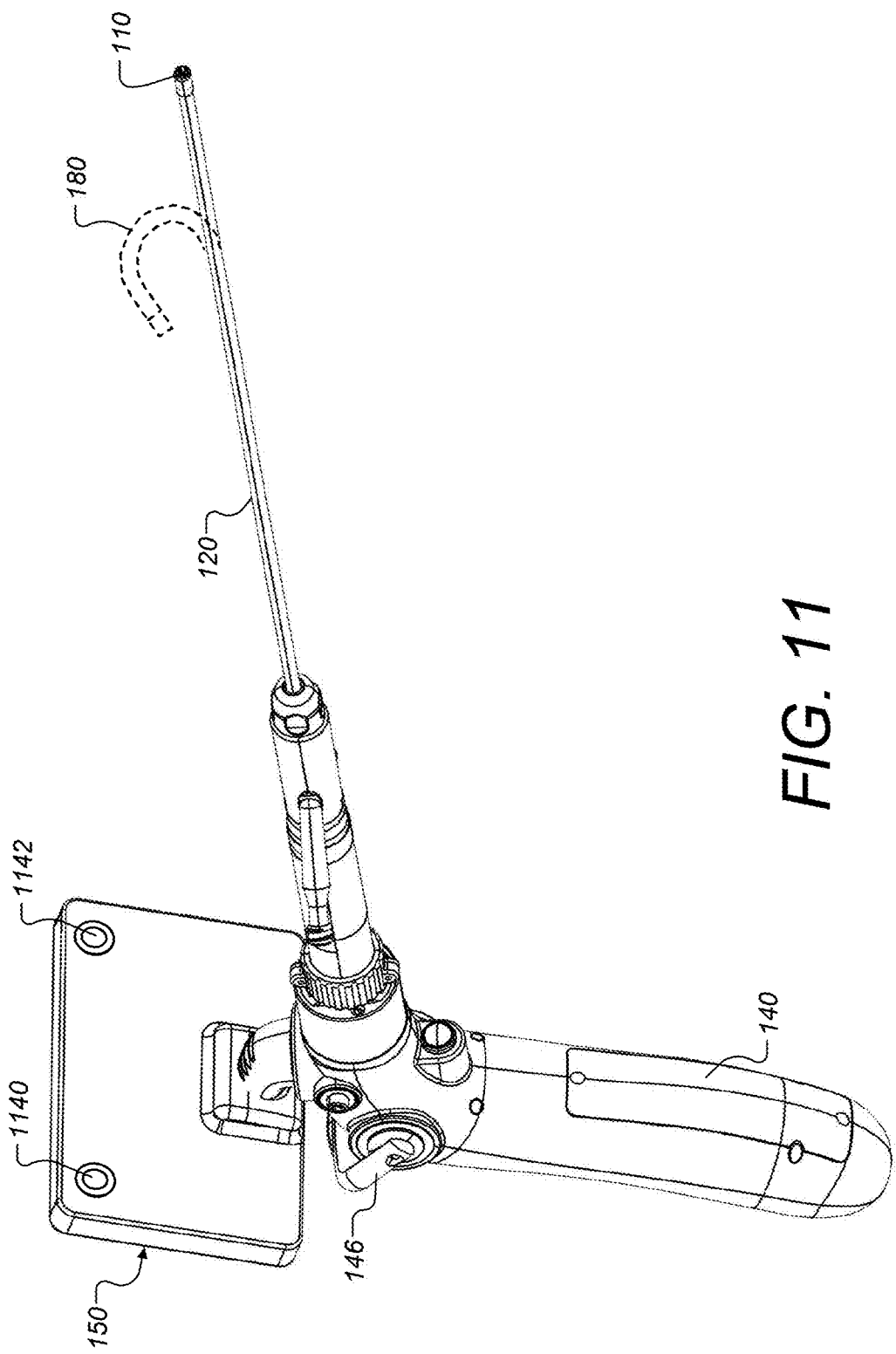
FIG. 11 is a perspective view of a endoscopy system having one or more forward facing cameras, according to some embodiments.

FIG. 11 is a perspective view of an endoscopy system having one or more forward facing cameras, according to some embodiments. The example shown has two forward (distally) facing cameras 1140 and 1142. The forward facing cameras allow the operator to see precisely where the distal tip is located, without having to move the screen out of the way. During a surgical procedure, especially immediately prior to or during initial insertion of the tip 110, the operator's view can be primary focused on the display screen 150. With forward facing cameras, 1140 and 1142, the precise location of the distal tip and its surroundings can be viewed on the display 150. Image enhancements such as artificially providing a depth of field may be beneficial in some procedures. The two cameras or other means (e.g. LIDAR imaging) may be used to simulate a depth of field centered on the distal tip to enhance usability.

Figure 12:
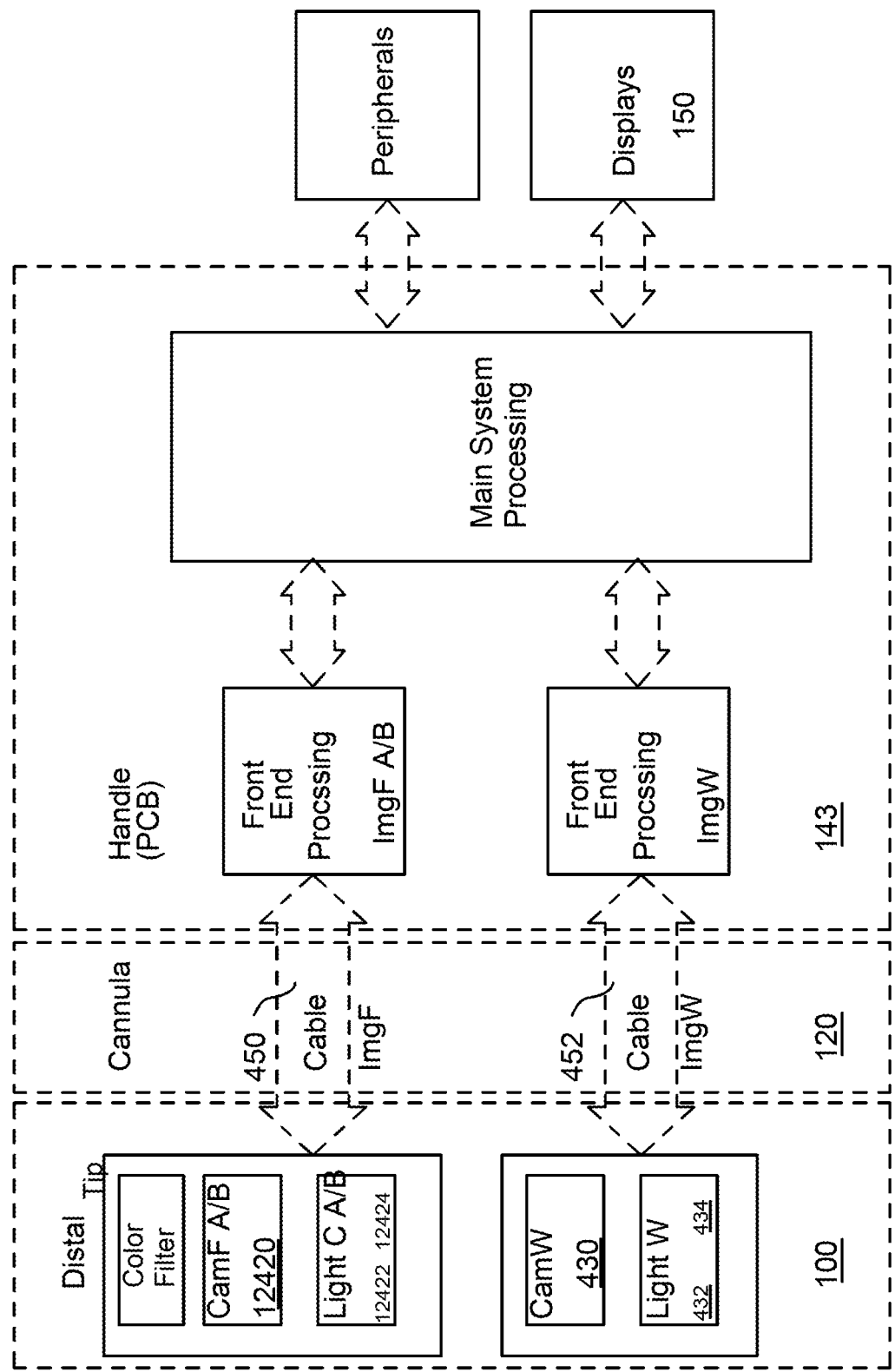
FIG. 12 is a schematic diagram illustrating an endoscope using a camera with an electrically controlled color filter to expose the camera to either white light or fluorescence and another camera doe white light, according to some embodiments.

FIG. 12 is like FIG. 5 in other respects but illustrates a multi-camera, multispectral endoscope in which two cameras are used to produce a white light stereo image in one mode of operation but a selected narrow wavelength band light image or a fluorescence image in another mode. The two images can be combined into a composite image like in FIG. 10. In FIG. 12, a forward-looking camera 430 (CamW) is at a distal portion of cannula 120 to view a target and is responsive primarily to a wavelength range of white light. An electrically controlled color filter 1202 also is at the distal portion of the cannula and is configured to selectively operate in a mode A to pass light primarily in a wavelength range of white light or in a mode B to pass light primarily in a selected narrow wavelength band or fluorescence light. Examples of such filters are discussed in https://en.wikipedia.org/wiki/Liquid crystal tunable filter and suitable wavelengths and color filters for use in endoscopes are discussed in U.S. application Ser. No. 16/363,209 published as U.S 2019/0216325 A1, both of which are hereby incorporated by reference. A forward-looking camera 12420 (CamFA/B) also at the distal portion of the cannula views said target from a different angle and through said color electrically controlled filter. Cameras 430 and 12420 view a target like the two cameras illustrated in FIG. 6. Processing system 143 configured to selectively switch said color filter between mode A and mode B, and to process image data received from cameras 430 and 12420 to form a white light stereo image of the target when said filter is operating in mode A, but to form a selected narrow wavelength band image or fluorescence light image from camera CamFA/B when said filter is operating in mode B. An image display 150 displays images and the processing system 143 and display 150 are configured to form and display a composite image as an overlay of the white light stereo image and the selected narrow wavelength band light image or fluorescence light image, like the image illustrates in FIG. 10 in which areas that differ is a selected parameter are highlighted. Processing system 143 can be configured to switch filter 1202 rapidly between modes 1 and 2, for example several times or hundreds of times or more per second, such that the stereo image and the selected narrow wavelength band image or fluorescence image for practical purposes are showing the target essentially in real time. As noted above, the selected narrow wavelength band image or fluorescence light image preferably has lower spatial resolution than the images from the white light cameras. Processing system 143 and display 150 can be configured to selectively display the composite image, or the stereo image, or the selected narrow wavelength band image or fluorescence image, or all three images at the same time. The composite image can be as in FIG. 10—an overlay of two spatially registered images of the same target but taken at different wavelengths of light.

Figure 13:
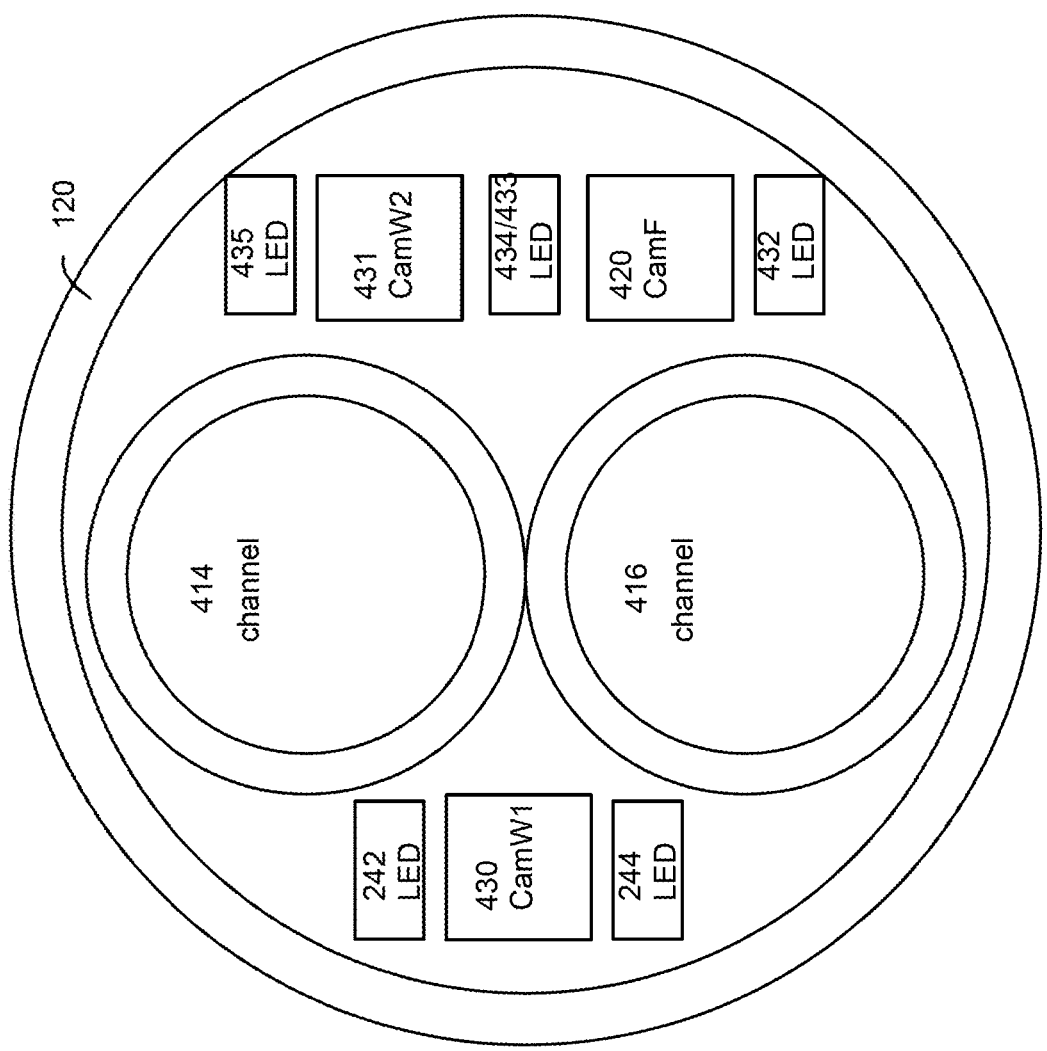
FIG. 13 is a plan view of a distal end of a cannula using a pair of white light camera and a camera for a selected narrow wavelength band or fluorescence light, and light sources and internal channels in the cannula, according to some embodiments.

FIG. 13 illustrates a multi-camera, multispectral endoscope in which a first forward-looking camera system provides a white light stereo image of a target, a second camera system provides a selected narrow wavelength band image or fluorescence light image of the target, and a processing system combines the two images into a composite image overlay for display. In FIG. 13, a first forward-looking camera system is located at a distal portion of cannula 120 and comprising two cameras—camera 430 (CamW1) and camera 431 (CamW2) both viewing the same target but from different angles, like the two cameras in FIG. 6. Camera 430 is responsive primarily to a CamW1 wavelength range and camera 431 is responsive primarily to a CamW2 wavelength range. The two wavelength ranges can be the same white light. A second camera system also is located at the distal portion of cannula 120 and comprises a camera 420 (Cam F) that also views said target but is responsive primarily to a CamF wavelength range that is different from at least one of the CamW1 and CamW2 wavelength ranges. The CamW1 and CmW2 wavelength ranges can be the same white light. The cam wavelength CamF can be a selected narrow wavelength band or fluorescence light. Processing system 143 (FIG. 6) is coupled with the first and second camera system and is configured to receive image data from said first and second camera systems and to process the received image data into a white light stereo image, a selected narrow wavelength band image or fluorescence light image, and a composite image overlaying said stereo image and the selected narrow wavelength band image or fluorescence light image. Processing system 143 also is configured to control LED light sources 242, 244, 432, 434, and 435 to turn them ON or OFF as required for the respective images. In this example, all three cameral in FIG. 13 can view the target concurrently. Processing system 143 and display 150 can be configured to selectively display the composite image, or the stereo image, or the selected narrow wavelength band image or fluorescence image, or all three images at the same time. The composite image can be as in FIG. 10—an overlay of two spatially registered images of the same target but taken at different wavelengths ranges of light. FIG. 13 illustrates two channels in cannula 120—414 and 416—but a single channel or more than two channels can be used.

Figure 14:
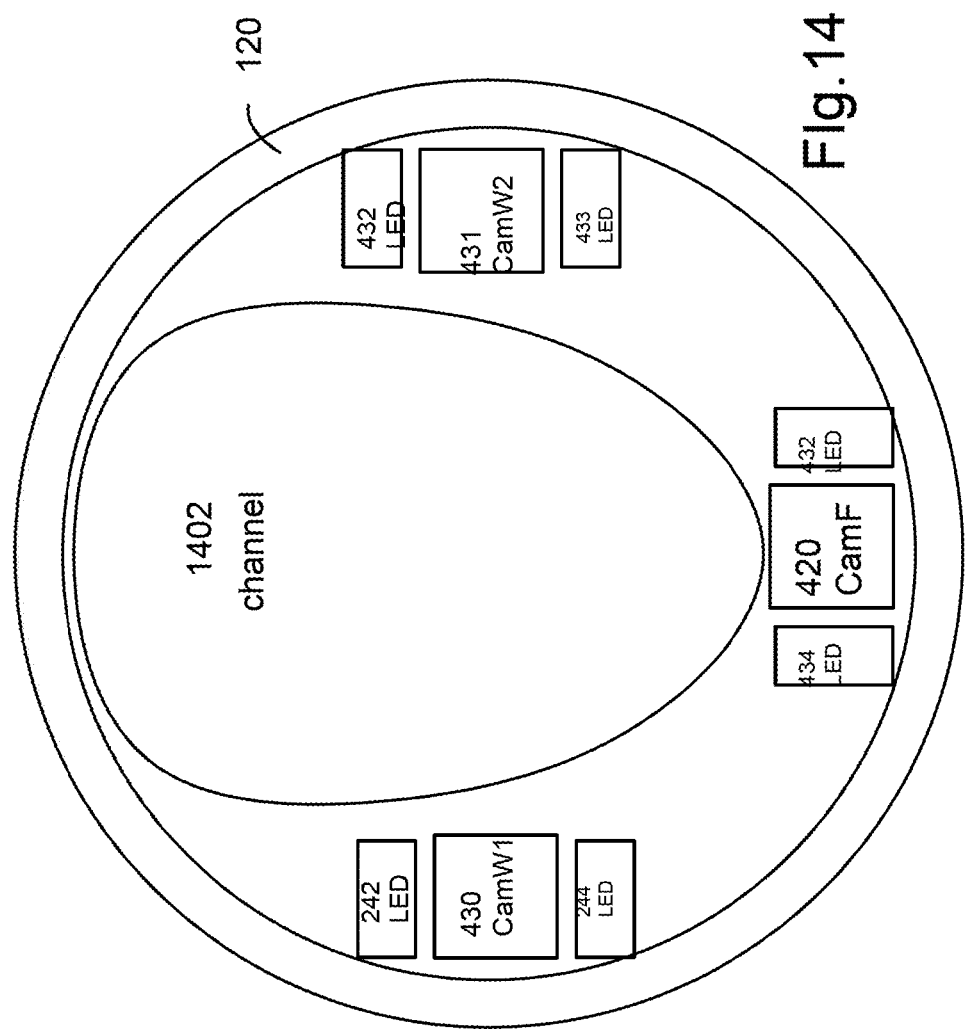
FIG. 14 is otherwise like FIG. 13 but shows a different arrangement of the cameras and light sources, and a single internal channel, according to some embodiments.

FIG. 14 is otherwise like FIG. 13 but illustrates a multi-camera, multispectral endoscope in which the three cameras and their light sources are arranged differently and cannula 120 has a single channel 1402

Figure 15:
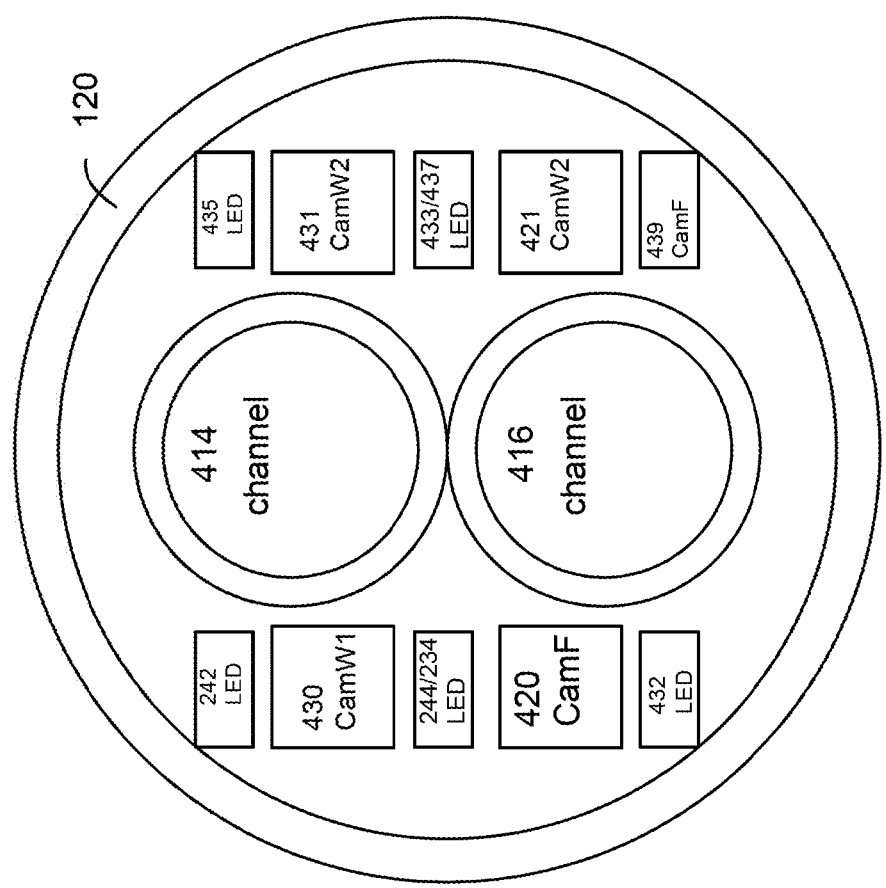
FIG. 15 is a plan view of a distal end of a cannula using a pair of white light camera and a pair of camera for a selected narrow wavelength band or fluorescence light, and light sources and internal channels in the cannula, according to some embodiments.

FIG. 15 is otherwise like FIG. 13 but illustrates a multi-camera, multispectral endoscope in which a second forward-looking camera system comprises CamF1 and CanF2, both imaging in the selected narrow wavelength band or fluorescence wavelength ranges such that the system can generate a stereo image both at white light and at the selected narrow wavelength band light or fluorescence light. In FIG. 14, a first forward-looking camera system at a distal portion of the cannula comprises a camera 430 (CamW1) and a camera 431 (CamW2) viewing a target from different angles as do the two cameras in FIG. 6. Cameras CamW1 and CamW2 are responsive to a CamW1 wavelength range and a CamW2 wavelength range respectively. A second forward-looking camera system also located at the distal portion of the cannula comprises a camera CamF1 and a camera CamF2 viewing said target from different angles and responsive to a CamF1 wavelength range and a CamF2 wavelength range respectively, which ranges can be the same or overlap and comprise a selected narrow wavelength band light or fluorescence light. The CamW1 and CamW2 wavelength ranges are white light ranges and can be the same or overlapping. The CamF1 and CamF2 wavelength ranges can be a selected narrow wavelength band light range or fluorescence light range and can be the same or overlapping. Processing system 143 receives image data from said first and second camera systems and processes the received image data into a white light stereo image of the target and a selected narrow wavelength band image or fluorescent light image of the target overlaid in a composite image, and a display 150 displays said composite image. Display 150 can display any one or more of the white stereo image, the selected narrow wavelength band or fluorescence image, and the composite image. The positions of the cameras can be interchanged so long as the two cameras of the first camera system view the target from different angles and the two cameras of the second camera system also view the target from different angles. FIG. 14 also illustrates two channels, 414 and 416 in cannula 120 although a different number of channels can be used. FIG. 14 also illustrates respective light sources 242, 244, 432, 434, 433, 435, 437, and 439, for the four cameras, although a different number or a different arrangement of light sources can be used.

Figure 16:
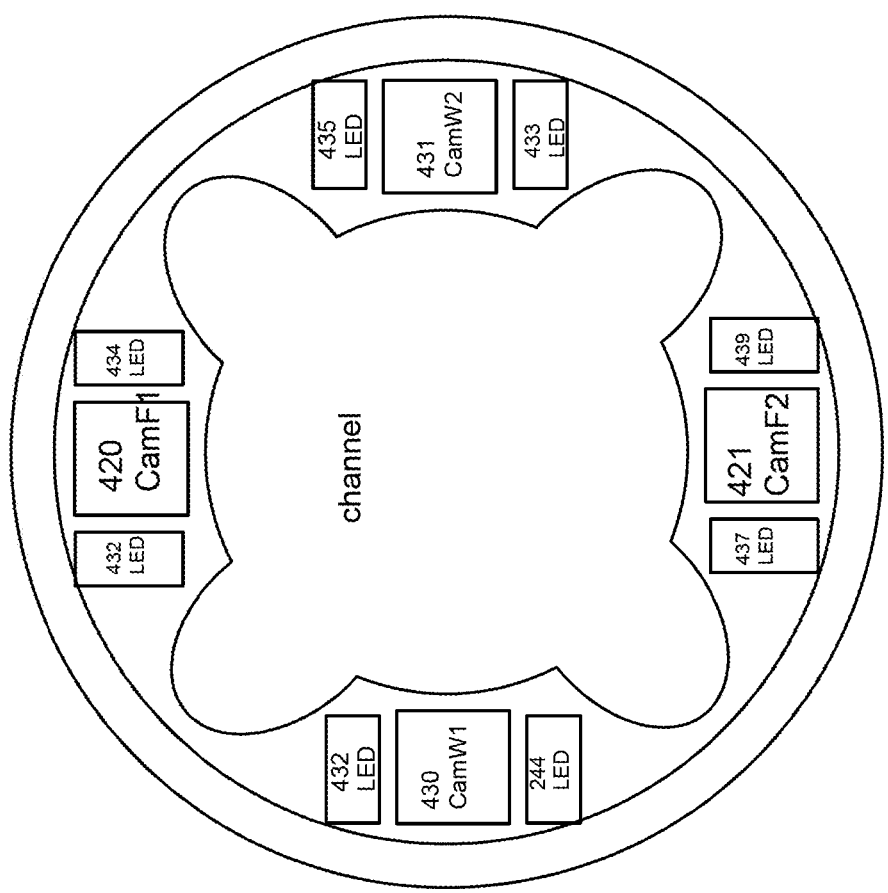
FIG. 16 is otherwise like FIG. 15 but shows a different arrangement of the cameras and light sources, and a single internal channel, according to some embodiments.

FIG. 16 is otherwise like FIG. 14 but illustrates a multi-camera, multispectral endoscope in which the four cameras and their light sources are arranged differently around a single channel 1502 in cannula 12.

Figure 17:
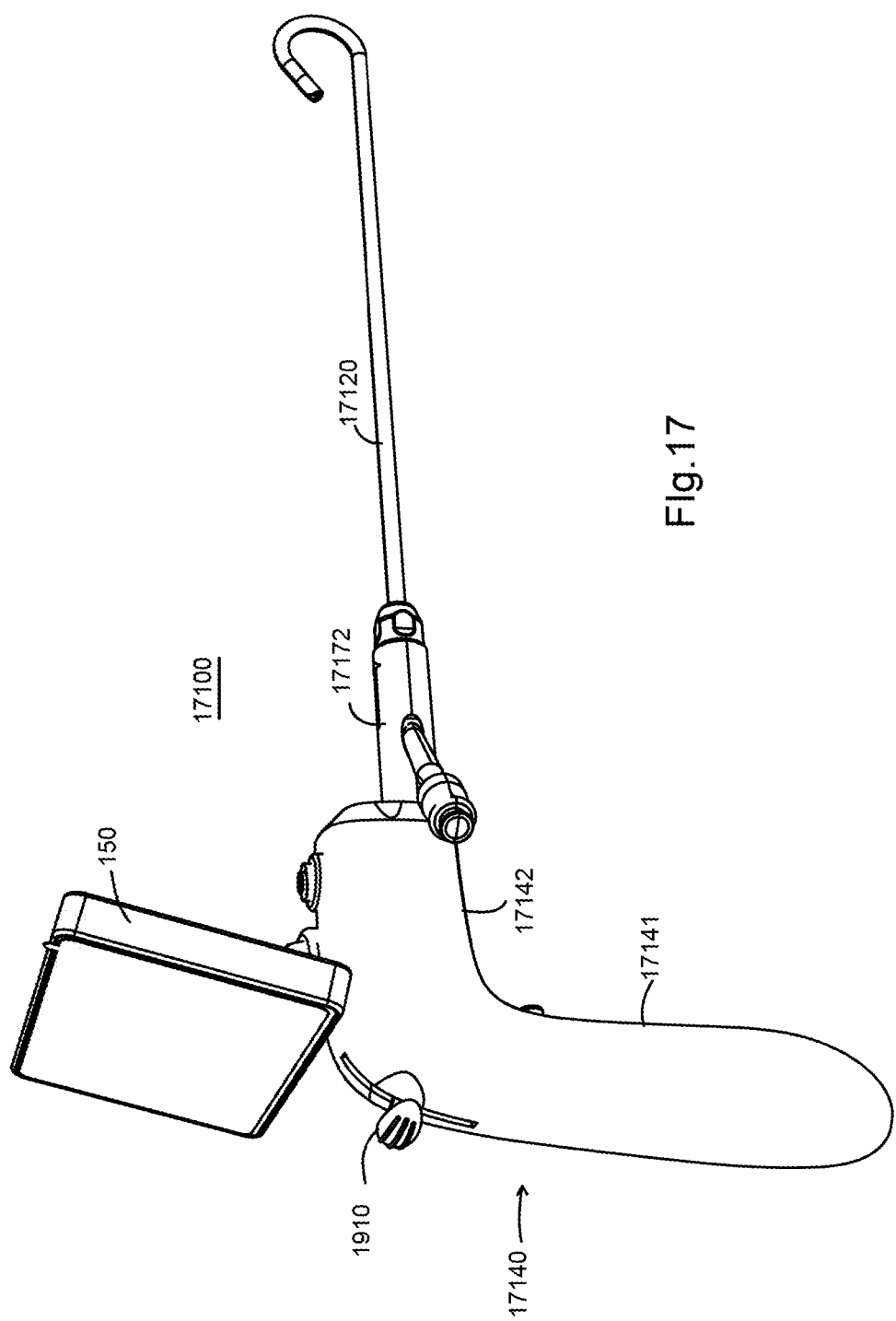
FIG. 17 is a perspective view of an endoscope, according to some embodiments.

FIGS. 17-22 illustrate an endoscope t according to some embodiments. FIG. 17 is a perspective view of an assemble endoscope 17100 and FIG. 18 illustrates as separate units a portion 17104 that can be reusable and a portion 17102 that can be single-use, before they are removably assembled by sliding portion 1702 proximally into portion 17104. Portion 17104 comprises display 150 and an L-shaped handle portion 17140 formed of a downwardly extending handle 17141 configured to be grasped by a user's hand and an axially extending housing 17142. Display 150 is mounted on portion 17104. Portion 17102 comprises a hub 17172 that can be removably secured to housing 17142 and a cannula 17120 extends distally from the hub. Housing 17142 has an axially extending, downward facing slot 1902 (FIGS. 18 and 19) and hub 17172 comprises an axially extending, upwardly facing rail 1802 that is configured to slide into slot 1902 in the proximal direction and thereby removably secure portions 17102 and 17104 to each other. Hub 17172 has a proximally facing electrical connector 1804 (FIG. 18) at its proximal end and housing 17142 has a matching, distally facing electrical connector 1904. The two electrical connectors mate and make electrical contact when portions 17102 and 17104 are secured to each other to form the assembled endoscope 17100 that FIG. 17 illustrates. The proximal end of handle portion 17140 has an oval opening 1906 through which the proximal end of thumb lever passes and protrudes proximally when the endoscope is assembled to the form seen in FIG. 17. Oval opening 1906 connects to a vertical opening 1908 that allows a stem of thumb lever 1910 to move up and down. Thumb lever is a part of a bending mechanism, described below, that bends the distal end of cannula to the bent position seen in FIG. 17 and to any intermediate positions. The bend can be up or down.

Figure 19:
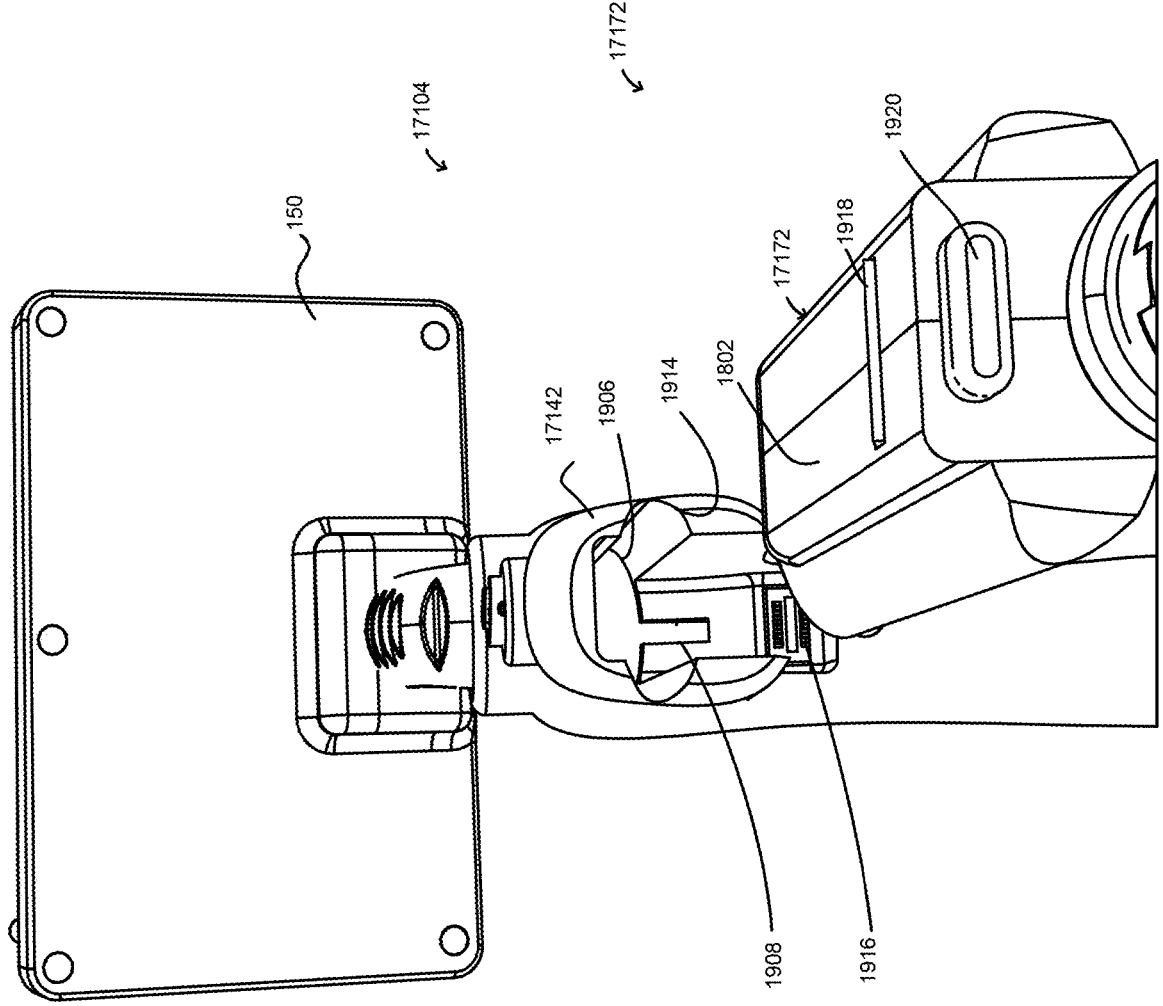
FIG. 19 is an exploded perspective view of portions of an endoscope, according to some embodiments.

FIG. 19 illustrates in perspective portions of units 17102 and 17104. As seen from the distal end, unit 17104 has an opening 1912 in which portion 17102 slides. Seen in this opening is an axial, downwardly facing, C-shaped slot 1914 and an electrical connector 1916. As seen in FIG. 18, hub 17172 has an upwardly facing, axially extending rail 1802 that is T-shaped and configured to slide into slot 1914 when the endoscope is assembled. Also seen in FIG. 18 is an electrical connector 1804 that configured to mate and make electrical contact with electrical connector 1916 seen in FIG. 19 when the endoscope is assembled. FIG. 19 also shows a lock pin 1918 and a lock release 1920 that serve to securely lock portions 17102 and 17104 when the endoscope is assembled and are described in more detail below in connection with FIG. 20. Cannula 17120 has at its distal end a camera and lights module that can be any of the modules discussed above regarding other embodiments of the endoscope and connects to display 150 through internal cables and electrical connectors (in this case 1916 and 1804) as discussed above for other embodiments. Portion 17104 can have buttons or other manually operated inputs as discussed above for other embodiments of the endoscope to control the camera functions and/or other functions. Handle portion 17140 can house electronics for processing image data as discussed above for other embodiments. In some embodiments of endoscope 17100, display 150 can be eliminated and image data can be displayed at an external monitor connected wirelessly or through a cable with the camera module at the distal end of cannula 17120.

Figure 20:
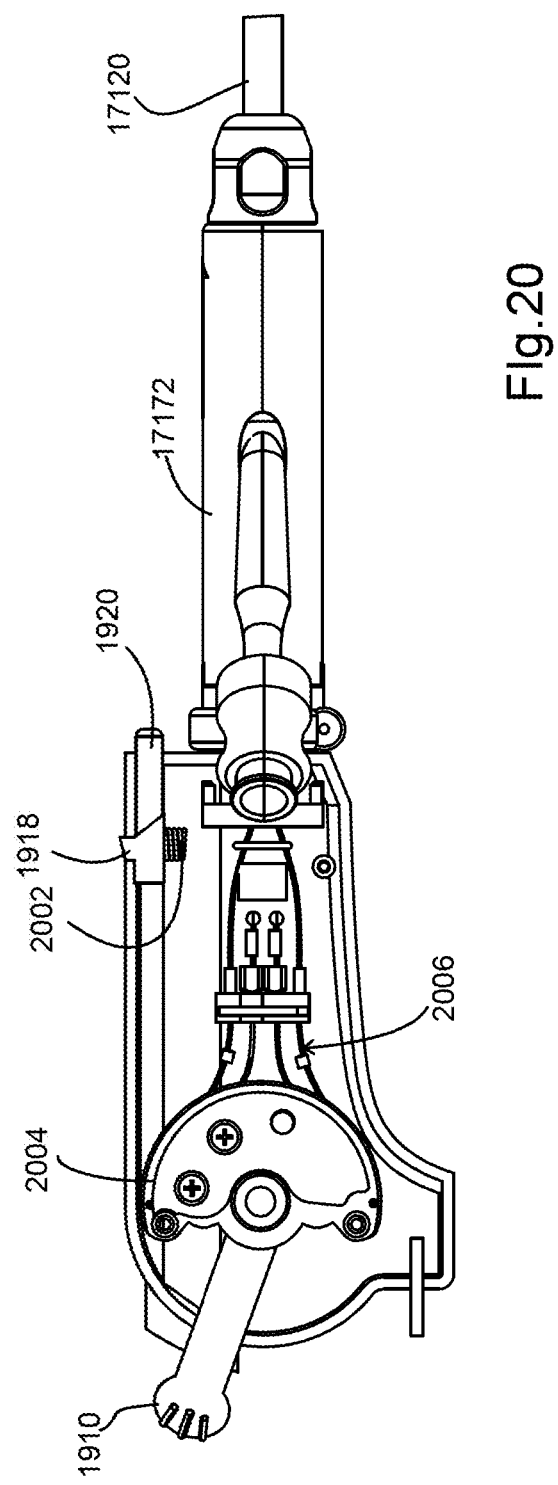
FIG. 20 is a sectional view of portions of an endoscope, according to some embodiments.

FIG. 20 is a sectional view of a portion of unit 17102 and shows lock pin 1918 that is urged up by a spring 2002 and a lock release 1920 that when pushed proximally pushes lock pin 1918 down and out of engagement with a catch 1922 (FIG. 18) that is a notch in the underside of opening 1914. When the endoscope is assembled, lock pin 1918 engages catch 1922 and holds units 17102 and 17104 together. After a medical procedure, the user pushes lock release 1920 to thereby release the engagement of pin 1918 and catch 1922 and pull unit 17102 distally out of unit 17104. FIG. 20 further illustrates a bending mechanism for bending the distal end of cannula 17120, which mechanism comprises a half-wheel 2004 mounted for rotation about its center and secured to thumb lever 1910 such that up-down motion of thumb lever 1910 translates to rotation of half-wheel 2004. Cables 2006 are secured to half-wheel 2006 and to the distal end of cannula 17120 such that rotation of half-wheel 2004 in one direction bends the distal end of the cannula in one direction and rotation of half-wheel 2004 in the opposite direction bends the distal end of the cannula in the opposite direction.

Figure 21:
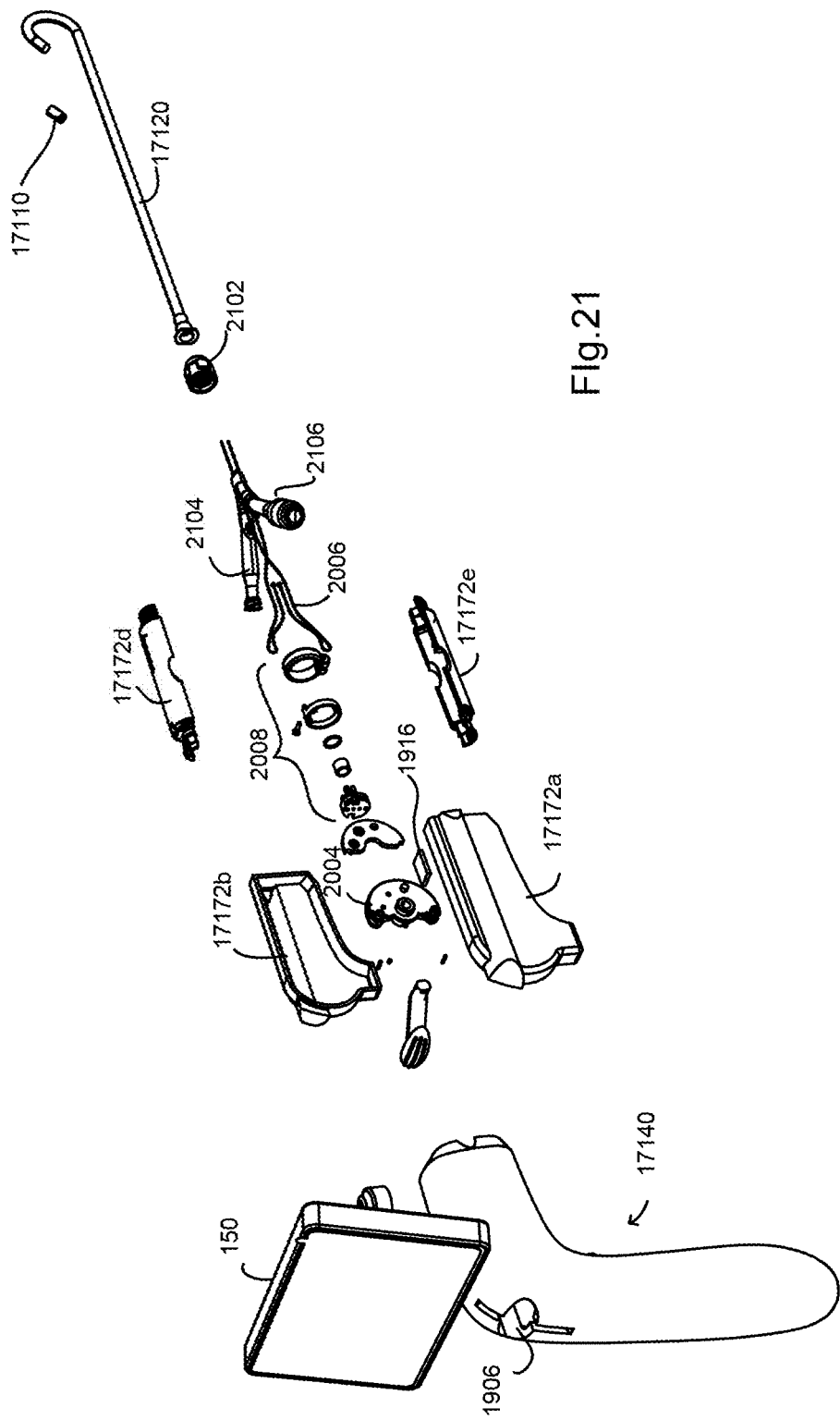
FIG. 21 is an exploded view of components of an endoscope, according to some embodiments.

FIG. 21 is an exploded perspective view illustrating handle portion 17140 and display 150 and components of portion 17102. Hub 17172 is formed of right and left covers 17172a and 127172b and right and left covers 17172c and 17172d that extend distally therefrom. A cap 2102 screws ono the distal end of hub 17172 to affix cannula 17120 to hub 17172. Fluid ports 2104 and 2106 merge into a Luer fork that goes into cannula 17120, as do cables 2006. Electrical connector 1916 (which can be a DP20 connector) also is a part of unit 17102. Mechanical connection pieces 2008 help in assembling portion 17102 of the endoscope.

Figure 22:
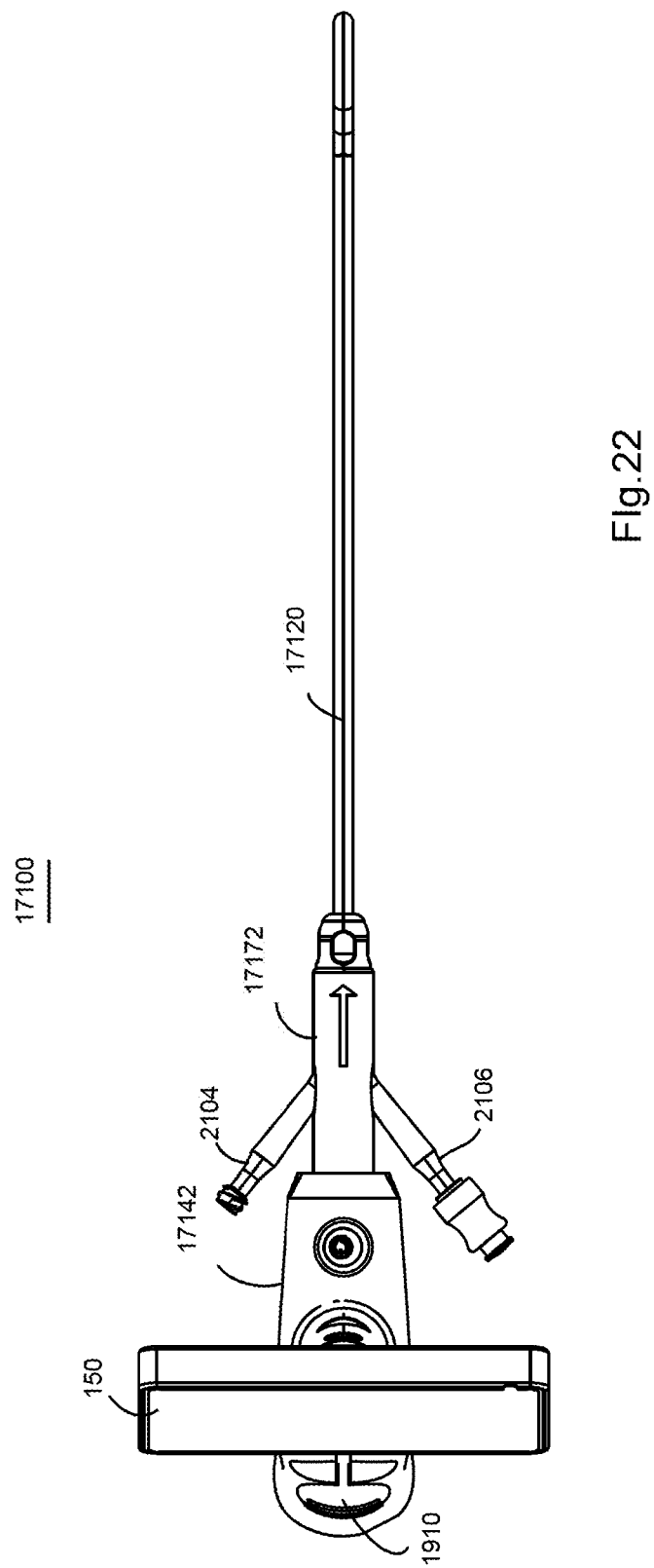
FIG. 22 is a top view of an endoscope, according to some embodiments.

FIG. 22 is a top view of the assembled endoscope 17100 and illustrates the relative positions of the components, including fluid ports 2104 and 2106.

As noted above, features and components described in connection with one of the embodiments can be used in another of the described embodiments. As non-limiting examples, the different configurations of imaging and lighting modules can be used in any of the described endoscopes, the cannula bending mechanism described in connection with FIG. 20 can be used in any of the described endoscopes, etc.

Endoscopy/Stereo Colposcopy and Other Examples

Figure 23:
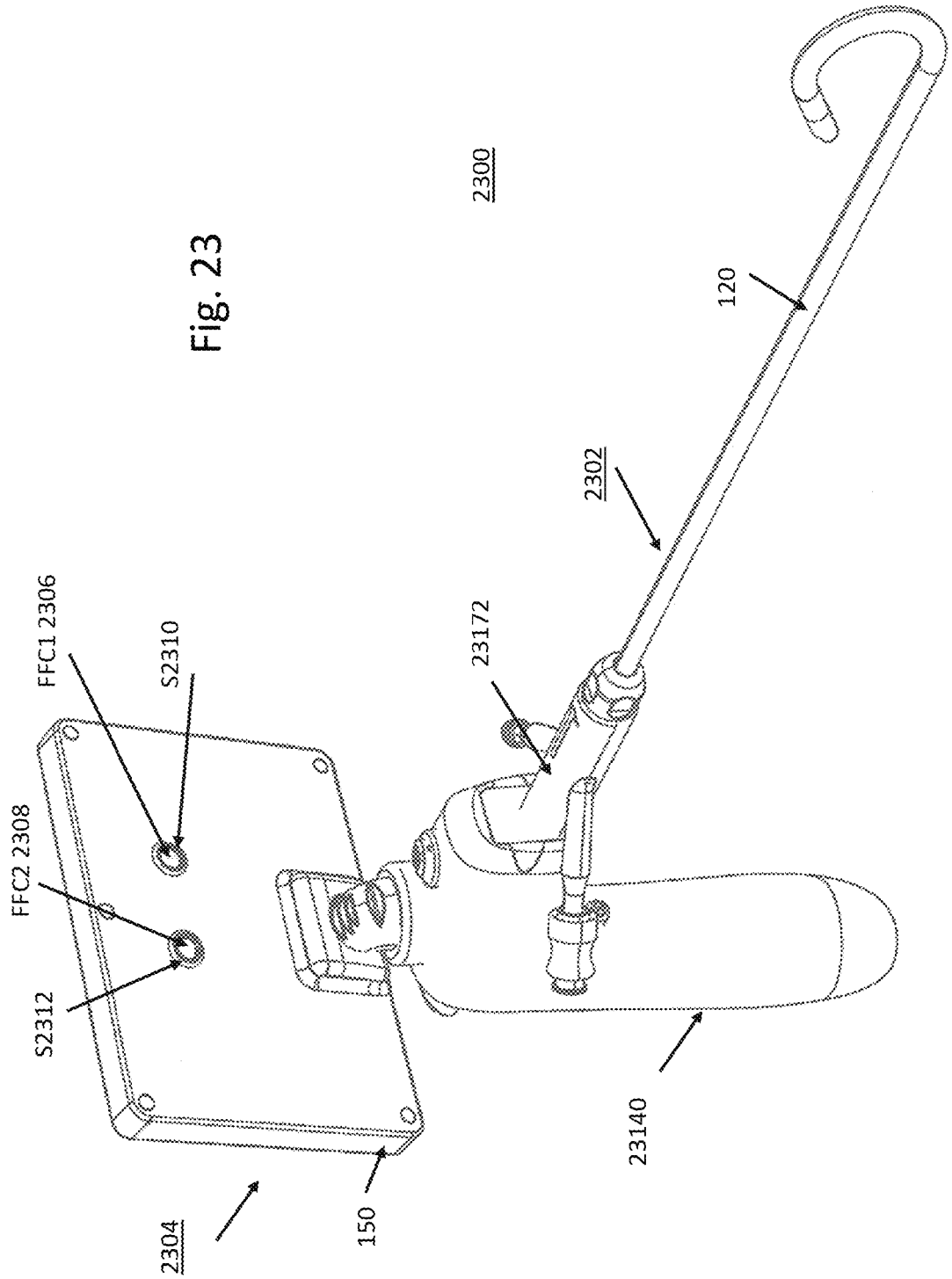
FIG. 23 is a perspective view of an endoscopy/stereo colposcopy instrument, according to some embodiments.

FIG. 23 illustrates in perspective an assembled endoscopy/stereo colposcopy instrument 2300, according to some embodiments. Instrument 2300 comprises a single-use portion 2302 that in all respects can be like portion 1702 seen in FIG. 18 and elsewhere and includes hub 23172 and cannula 120 that has an endoscopy camera and an endoscopy light source at the distal end. Instrument 2300 further comprises a reusable portion 2304 that is otherwise like portion 17104 seen in FIG. 18 and elsewhere but adds important functionalities not discussed for FIGS. 1A-22. These functionalities include an imaging and lighting system comprising forward-facing camera (FFC) 2306 and FFC 2308, surrounded by respective light sources S2310 and S2312 that can be arrays of LEDs selectively emitting white light or color light in selected wavelength ranges. At least one of the FFCs preferably has spatial resolution of at least 8 Mega Pixels and preferably higher spatial resolution, and the two FFCs can have the same or different spatial resolution and/or sensitivity. As illustrated, the FFCs are spaced from each other so they can provide a stereo view of a target and are angled to view the same target at a selected distance such as 25-30 cm (or another suitable distance) away or a different selected distance. The FFCs preferably are mounted at the forward-facing side of display 150 but can be mounted in another way to reusable portion 2304. Like reusable portion 17104, reusable portion 2304 includes a handle 23140 configured to be grasped by a user's hand and display 150 mounted to reusable portion 2304. In addition, reusable portion 2304 differs from reusable portion 1704 by adding electronics configured to process for display the image data from FFCs 2306 and 2308.

Figure 24:
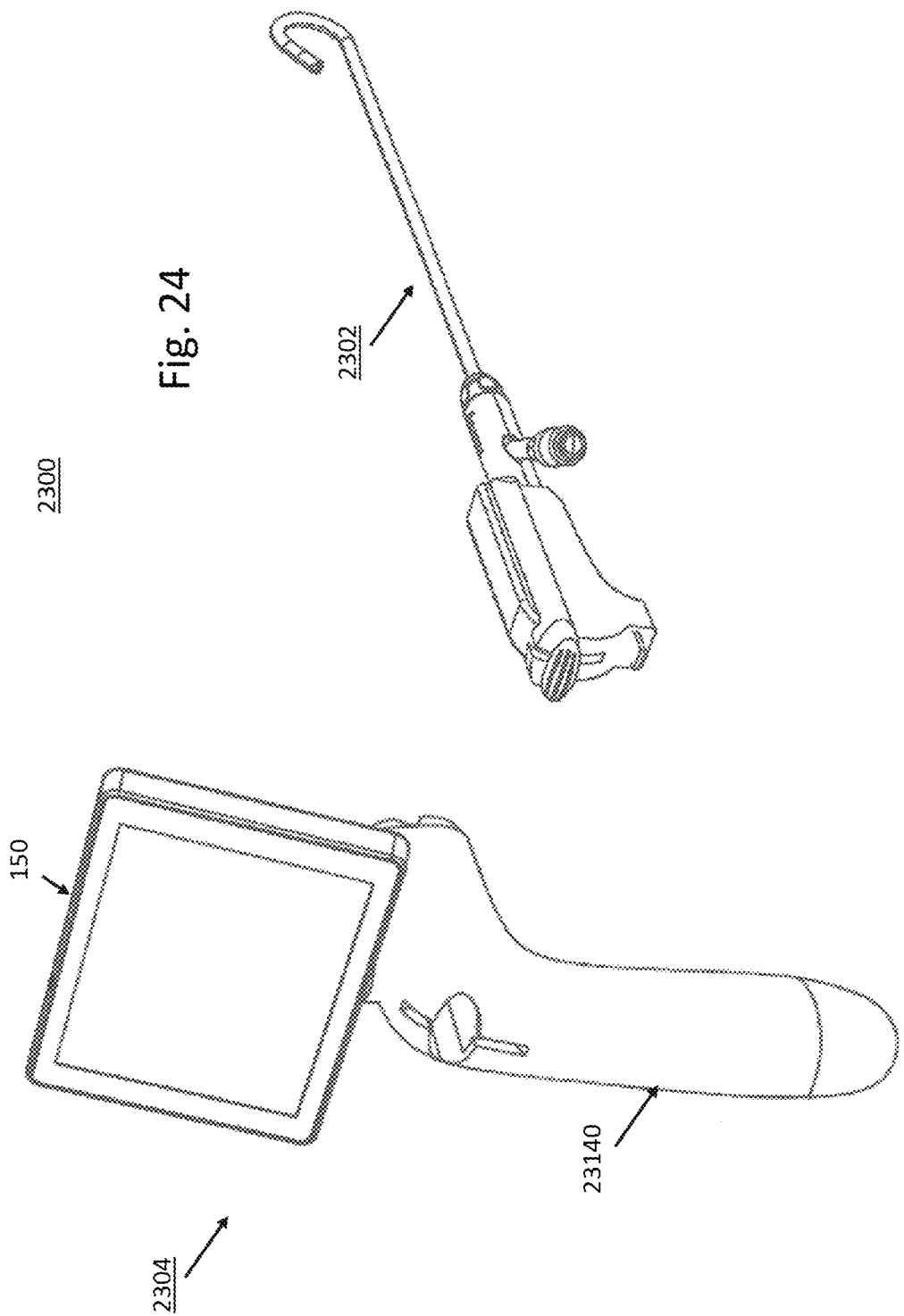
FIG. 24 is a perspective view of an endoscopy/stereo colposcopy instrument of FIG. 23 showing a reusable portion and a single-use portion that can be releasably attached to each other to form an assembled endoscope, according to some embodiments.

FIG. 24 illustrates in perspective endoscopy/stereo colposcopy instrument 2300 showing reusable portion 2304 and a single-use portion 2302 that can be releasably attached to each other to form an assembled endoscope, according to some embodiments. Portions 2302 and 2304 can be assembled to form an assembled endoscope as described above in connection with FIG. 18 and other figures. When so assembled, instrument 2300 can be used as an endoscope in the same manner as described above for the endoscope examples of FIGS. 1A-22.

FIG. 25 is a perspective view of instrument 2300 like that of FIG. 24, before single-use portions 2302 and 2304 are assembled, but from a different viewpoint, according to some embodiments.

Figure 26:
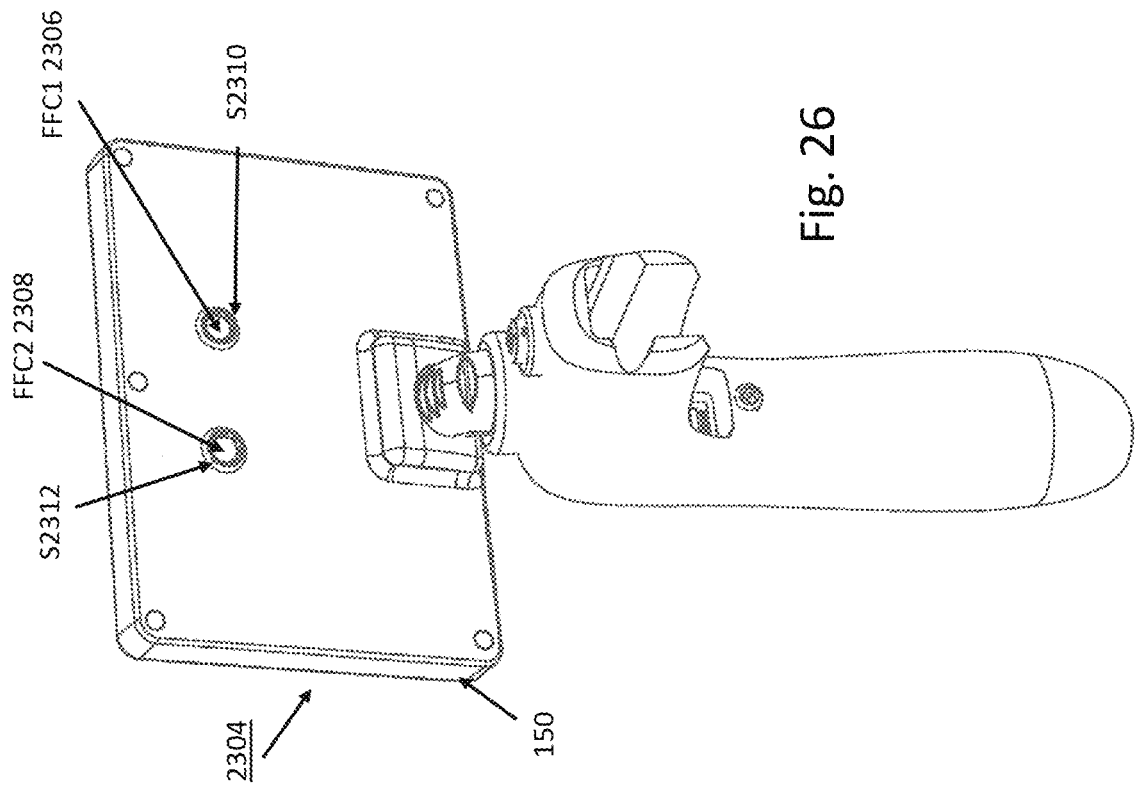
FIG. 26 is a perspective view of a reusable portion of the instrument when used for colposcopy using white light imaging or narrow band imaging with light in a selected color or color range, according to some embodiments.

FIG. 26 is a perspective view of reusable portion 2300 and illustrates a configuration for colposcopy using white light imaging or narrow band imaging with light in a selected color or color range, according to some embodiments. Reusable portion 2304 has several operational modes in which FFCs 2306 and 2308 and light sources S2310 and S2312 operate differently and display 150 displays different images.

In a white stereo mode, light sources S2310 and S2312 are configured to emit white light, such as from white LEDs, and cameras FFC1 and FFC2 acquire white light images simultaneously and provide image data that electronics in reusable portion 2304 process into a stereo image of a target such as a patient's cervix that display 150 shows at its proximal side. For white only, a single LED source can be used for both cameras. Display 150 can be touch-sensitive and configured to respond to commands to digitally zoom the displayed images. As noted, the spatial resolution of one or both FFCs preferably is HD or 8 Mega Pixels but can be and more preferably is higher, although in special cases one or both FFCs can use lower spatial resolution.

In a narrow band imaging mode, light sources S2310 and S2312 are configured to emit light in a narrow band such as green light from green LEDs included in the light sources in addition to white LEDs. FFCs 2306 and 2308 acquire green light images simultaneously that reusable portion 2304 processes into display images into stereo images of the target that show at the proximal face of display 150.

In another example of a narrow band imaging mode, light sources S2310 and S2312 are configured to emit light in a narrow band such as blue light from blue LEDs included in the light sources in addition to white and any green LEDs. FFCs 2306 and 2308 acquire blue light images simultaneously that reusable portion 2304 processes into display images into stereo images of the target that show at the proximal face of display 150.

If desired in special cases, only one of FFCs 2306 and 2308 can be used in any of the modes described above, in which case display 150 would show a two-dimensional (2D) image of the target rather than a stereo (3D) image. Both light sources S2310 and 2312 or only one of them can be used to illuminate the target in such special cases.

Figure 27:
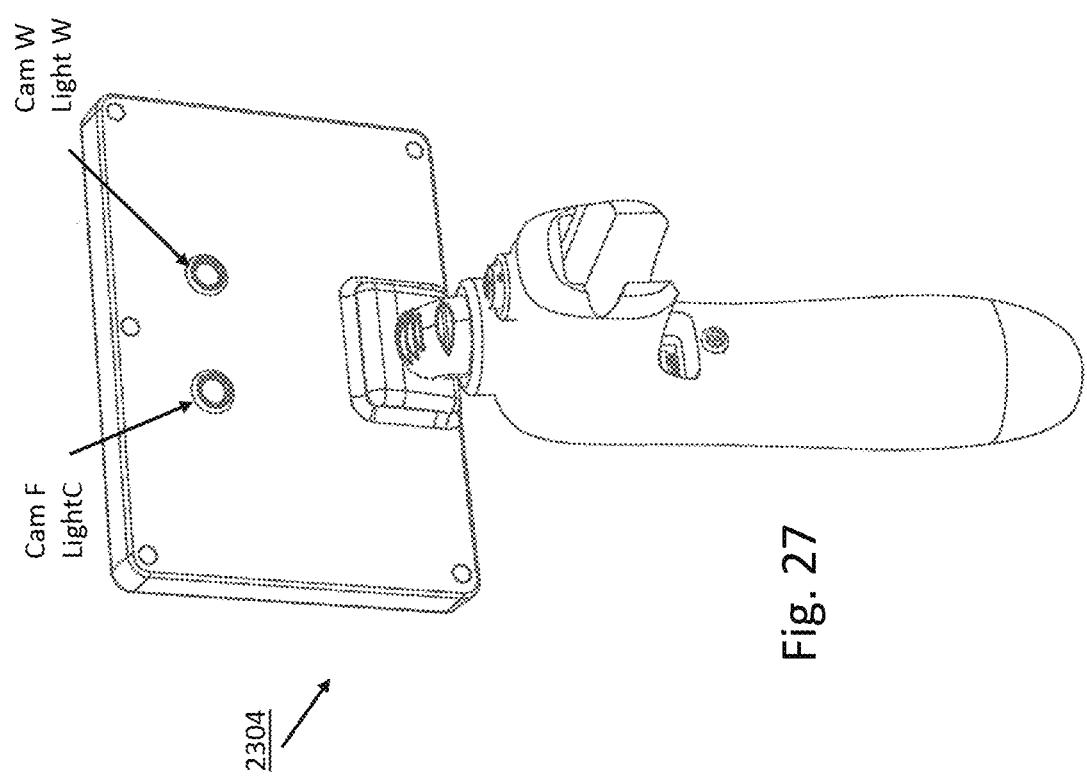
FIG. 27 is like FIG. 26 but illustrates use for fluorescence imaging, according to some embodiments.

FIG. 27 is like FIG. 26 but illustrates a fluorescence imaging mode of a target such as a patient's cervix, according to some embodiments. In this mode, the target is caused to fluoresce, for example by marking the target or a selected area of the target with a substance that emits fluorescent light or is activated with suitable light to fluoresce. In this mode, camera CamW has a light source LightW that illuminates the target (e.g., cervix) with white light and CamF has a light source LightC that illuminates the target with light causing fluorescence from target tissue. Camera CamF has a color filter that preferentially passes fluorescence light. Cameras CamF and CamW preferably acquire image data simultaneously. Reusable portion 2304 processes the image data into a white light image and a fluorescence image and preferably superimposes them in registration into a composite image for display. In special cases, each of the white and fluorescence images can be displayed separately.

In other examples, the forward-looking cameras FFC1 and FFC2 and cameras CamW and CamF can be replaced with a set of a greater number of cameras and light sources, as described for the cameras and light sources illustrated in FIGS. 12-16 for cameras at the distal end of cannula 120.

Figure 28:
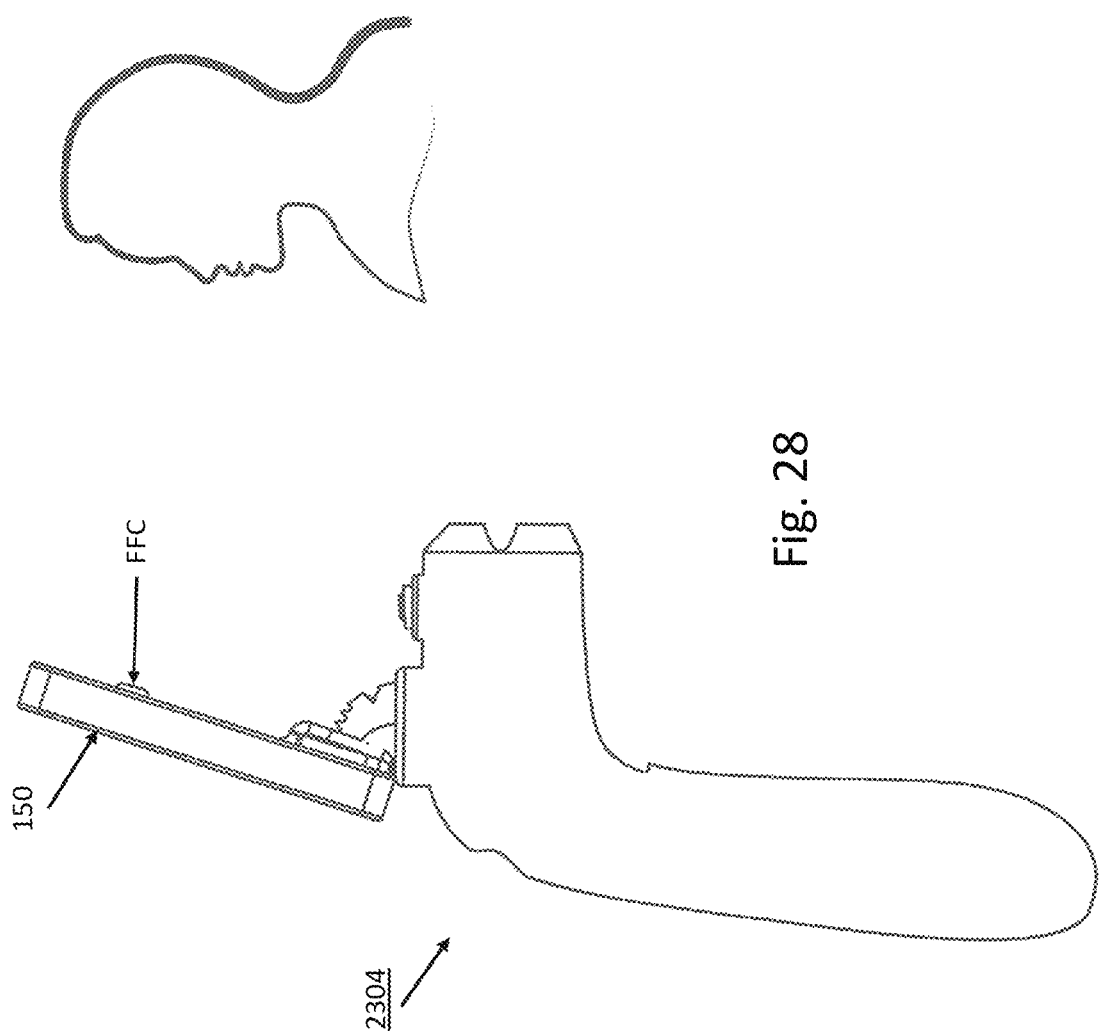
FIG. 28 is a side view illustrating use for face recognition, according to some embodiments.

FIG. 28 is a side view illustrating use for face recognition, according to some embodiments. In this example, one or both cameras FFC1 and FFC2 at reusable portion 2304 image a user and a face-recognition facility identifies the user and provides data used for example to automatically associate a user with the act of assembling reusable portion 2304 with a single-use portion 2302 or to associate a user with images acquired with instrument 2300.

Figure 29:
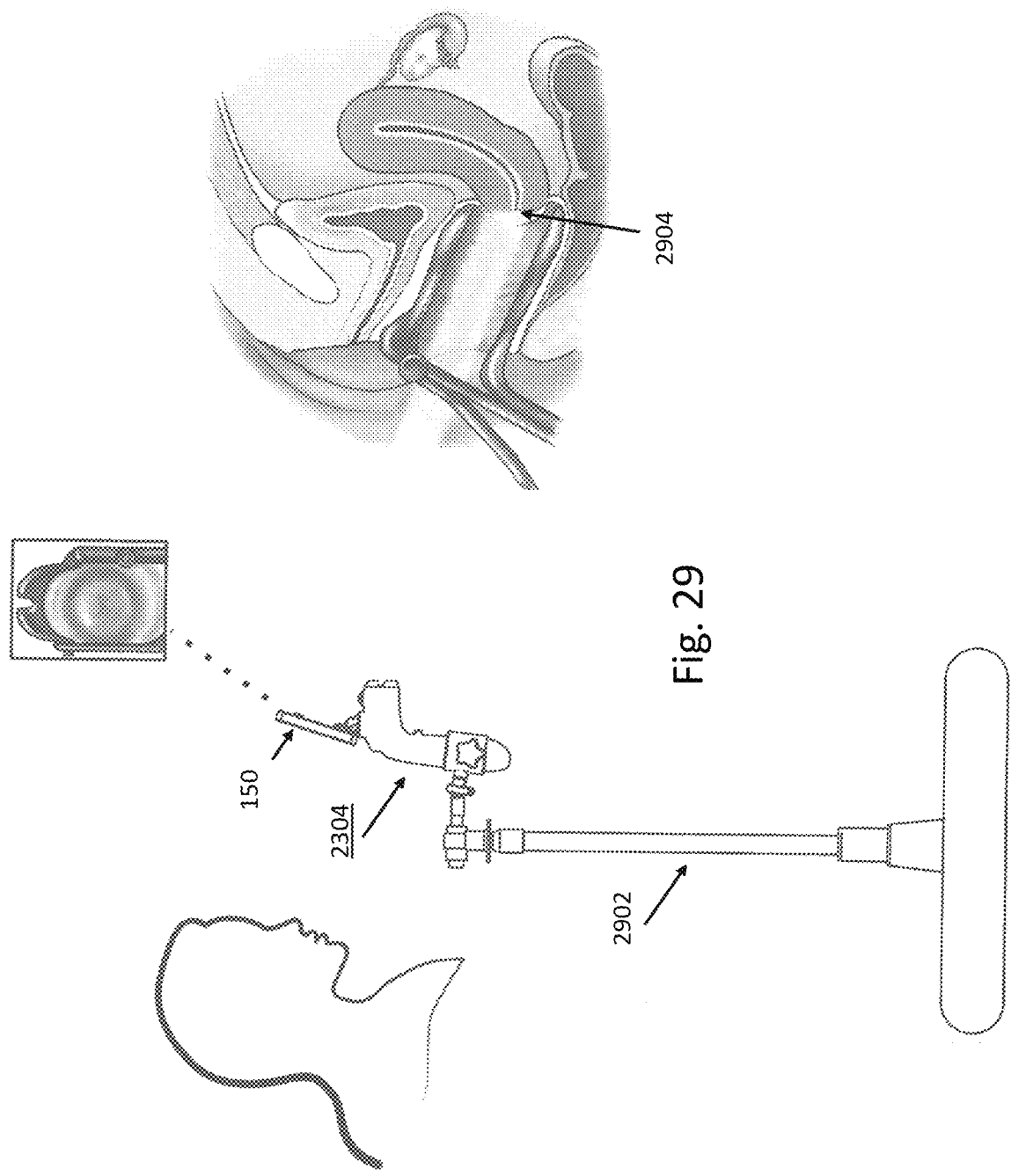
FIG. 29 illustrates use in a colposcopy procedure, according to some embodiments.

FIG. 29 illustrates reusable portion 2304 used in a colposcopy procedure, according to some embodiments. In this example, reusable portion is secured to a height-adjustable and angle-adjustable holder 2902. Holder 2902 is adjusted for the light of sight of a user and for distance from and angle relative to the target (cervix 2904). A speculum used in a conventional way provides a path for illumination and viewing the cervix. An inset illustrates a stereoscopic view of the cervix that is displayed at the proximal face of display 150.

Figure 30:
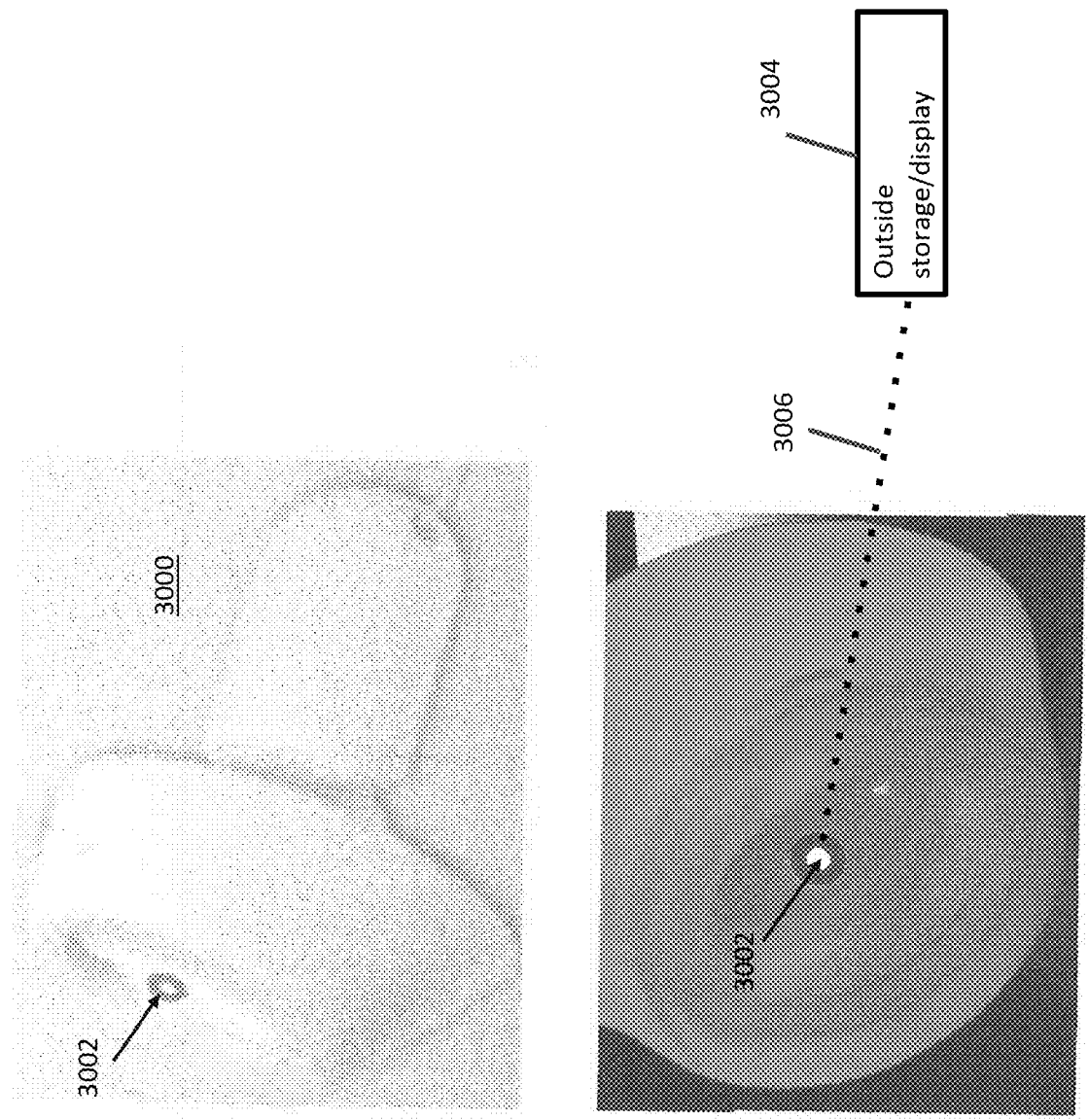
FIG. 30 is a perspective view illustrating a device for embedded fluorescent image of a cervix.

FIG. 30 is a perspective view illustrating a device for embedded fluorescent imaging of a cervix. A device for photodynamic therapy of a patient's cervix is discussed in U.S. Pat. Nos. 9,974,974 and 10,485,985 incorporated herein by reference, and a commercial product named Cevira is believed to be commercially available and in use for that purpose. The device is believed to include a battery-powered light source that illuminates and thus activates a substance adhered to the cervix for photodynamic therapy (PDT). According to some embodiments described in this patent specification, a camera 3002 is added to form an integrated device 3000. Camera 3002 is secured to the cup-shaped portion of device 3000, facing the cervix area being treated when device 3000 is secured in place over a patient's cervix. Camera 3002 can be tuned with a suitable color filter to image fluorescence from cervix, like camera CamF described above, or to image another wavelength band, or to image white light, and can be powered by the batter that powers the light source in device 3000 or by another battery. Camera 3002 provides image data that can be stored in a memory secured to device 3000 or can be delivered to an outside device 3004 by wire or wirelessly. In the case of using a wire connection. In the case of wire connection, thin cables 3006 can connect device 3000 to outside device 3004 that can be worn by the patient to store image data and/or display image data from camera 3002. In that case, outside device 3004 can be battery powered and provide power to camera 3002. In the case of a wireless connection, a WiFi or other transmitter can be included in device 3000 to transmit image data wirelessly to outside device 3004 for storage and/or display. Camera 3002 can rely on the light used for photodynamic therapy to induce fluorescence or on inherent fluorescence from a substance provided at the cervix. Alternatively, camera 3002 cane include a light source that induces fluorescence.

Camera 3002 need not be powered continuously. Preferably, camera 3002 is configured to take one or more images at selected times only, for example when device 3000 is inserted and positioned in the patient, to confirm proper placement and that the desired target is being illuminated, and at time intervals over the course photodynamic therapy while device 3000 remains in the patient to thereby monitor the therapy.

A single FFC camera 3002 can be sufficient for colposcopy. Thus, in a single FFC camera mode, only one FCC camera can be mounted to the reusable portion 17140, with its light source S1. In that case, the single FCC camera can provide a two-dimensional view of the cervix rather than a stereo (3D) view. Alternatively, only one of the two FFC cameras 3002 and 3004 can be energized to carry out a single-FFC mode. However, a second like camera can be provided and energized in device 3000, with the two cameras FFC spaced apart to provide image date for a stereo view.

In yet another mode, cameras FFC1 and FFC2 and their light sources S1 and S2, are configured to operate in time-alternating mode in which they alternate between acquiring images for different wavelength bands. For example, images are acquired in repeating sets of sequences of green light images, blue light images, and white images. If the sequencing is sufficiently rapid, the system this acquires essentially simultaneously all three types of images or any two of them and can display them individually or in selected spatially registered superpositions of images, for example a superposition of only two of the different color images or of all three. The switching of light sources and cameras can be as described above for the multi-spectral mode using two or more cameras an respective light sources in an imaging module at the tip of cannula 120.

Figure 31:
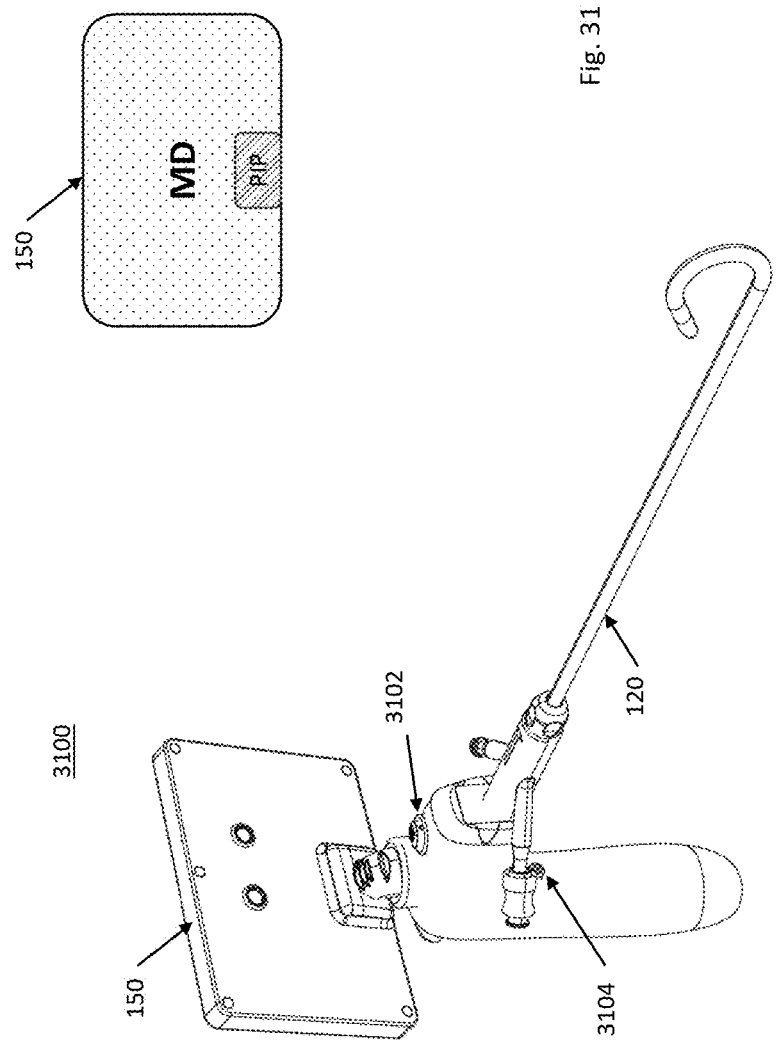
FIG. 31 illustrates an instrument with both endoscopy and colposcopy functionalities and an example of arranging images on a display, according to some embodiments.

FIG. 31 illustrates an instrument 3100 with both endoscopy and colposcopy functionalities that is like those discussed above, and an example of arranging images on a display, according to some embodiments. Instrument 3100 has a power key 3102 to turn the instrument ON and OFF, and a snap key 3104 to initiate image acquisition. The colposcopy cameras are designated FFC and the imaging module at the tip of cannula 120 is designate Hysteroscopy Camera or EDC (although the instrument can be used for medical procedures other than hysteroscopy as well). As illustrated, the display face of display 150 can be divided into two areas, and Main Display Window MD that can display images from EDC (e.g., hysteroscopy Images) or Colposcopy Images (FFC) and a Picture in Picture Window PIP that also can display images from EDC (e.g., hysteroscopy images) or Colposcopy images (FFC). Other examples of arranging images on display 150 also are possible.

FIG. 32 is a flow chart illustrating an example of sequences of steps in using an instrument with both endoscopy and colposcopy functionalities, according to some embodiments. At step 3202, instrument 3100 is powered with power key 3102, and at step 3204 the screen of display 150 shows, for example, a logo such as HysteroVue and/or some other information to show the user that the instrument is powered and ready for use. At step 3206, cameras FFC1 and FFC2 are enabled to acquire images by light sources S1 and S2 preferably are OFF. At step 3208, the instrument checks if single-use portion 17102 is connected to reusable portion 17104. If the answer is NO, at step 3209 the screen of display 150 shows a colposcopy menu in screen portion MD that includes, for example, a facility for entering patient ID and/or other information about the patient and medical procedure, and at step 3211 light sources S2310 and S2312 are turned ON and the instrument enters the colposcopy mode described above (or used face recognition). If the answer at step 3208 is YES, the instrument prepares to enter hysteroscopy mode (or another mode in which the imaging module EDC at the tip of cannula 120 will acquire images). At step 3210, which is an initial step related to insertion of cannula 120 into a patient, the main display MD shows live videos from the FFC cameras and the PIP area shows live videos from the EDC camera (but the light source at the tip of cannula 120 preferably is OFF at this time). At step 3212, the screen of display 150 displays a main menu for endoscopy such as allowing touch screen entry of patient identification and/or other information at the MD portion. At step 3214, instrument 3100 fully enters its endoscopy mode and the light source(s) of the imaging module at the tip of cannula 120 are turned ON. After inserting cannula 120 in the patient, the user can touch the EDC window on the screen of display 150 to make the FFC window disappear and can proceed with an endoscopy examination to acquire images in the desired color range(s).

Although the foregoing has been described in some detail for purposes of clarity, it will be apparent that certain changes and modifications may be made without departing from the principles thereof. It should be noted that there are many alternative ways of implementing both the processes and apparatuses described herein. Accordingly, the present embodiments are to be considered as illustrative and not restrictive, and the body of work described herein is not to be limited to the details given herein, which may be modified within the scope and equivalents of the appended claims.

What it claimed is:

1. A medical endoscopy/stereo colposcopy instrument comprising:
   a reusable portion that includes a handle configured to be grasped by a user's hand and a display mounted to the reusable portion;
   a forward-facing colposcopy imaging and lighting system mounted to said reusable portion and comprising a first colposcopy camera FFC1 and first light source S1 and a second colposcopy camera FFC2 and second light source S2, configured to take stereo colposcopy images of a patient's cervix for display at said display;
   a single-use portion comprising a cannula configured for insertion in the patient and having an endoscopy imaging and lighting system comprising an endoscopy camera and endoscopy light source at a distal end of the cannula;
   interlocking mounts at a proximal end of the single-use portion and at the reusable portion, configured to releasably couple the reusable and single-use portions to each other to thereby form an assembled endoscope configured to take endoscopy images with said endoscopic imaging and lighting system for display at said display; and
   a processor configured to process image data from said colposcopy imaging and lighting system and said endoscopy imaging and lighting system into colposcopy images and endoscopy images and to cause said display to show one or both the colposcopy and endoscopy images.

2. The medical endoscopy/stereo colposcopy instrument of claim 1, in which the cameras FFC1 and FFC2 and the light sources S1 and S2 are mounted at a distal-facing side of the display.

3. The medical endoscopy/stereo colposcopy instrument of claim 1, in which said light source S1 is configured to selectively emit light in a first selected narrow wavelength band narrower that white light.

4. The medical endoscopy/stereo colposcopy instrument of claim 3, in which said narrow wavelength band is configured to cause emission of fluorescent light from a location in the patient.

5. The medical endoscopy/stereo colposcopy instrument of claim 3, in which said camera FFC1 is configured to image light associated with said narrow wavelength band.

6. The medical endoscopy/stereo colposcopy instrument of claim 5, in which said camera FFC1 is configured to image fluorescence.

7. The medical endoscopy/stereo colposcopy instrument of claim 5, in which said camera FFC2 is configured to image white light.

8. The medical endoscopy/stereo colposcopy instrument of claim 3, in which said camera FFC1 is configured to image light associated with said narrow wavelength band and has lower spatial resolution but higher sensitivity than said camera FFC2.

9. The medical endoscopy/stereo colposcopy instrument of claim 1, in which said camera FFC1 includes a first electrically controlled color filter configured to selectively switch between light in a selected color and white light.

10. The medical endoscopy/stereo colposcopy instrument of claim 1, in which said camera FFC1 is configured to image light associated with said narrow wavelength band, said camera FFC2 is configured to image white light, and said display is configured to superimpose spatially registered images taken with the cameras FFC1 and FFC2.

11. The medical endoscopy/stereo colposcopy instrument of claim 1, in which both cameras FFC1 and FFC2 image white light and are spaced from each other for a stereo view of the patient's cervix.

12. The medical endoscopy/stereo colposcopy instrument of claim 1, in which both cameras FFC1 and FFC2 are configured to image light in a selected narrow wavelength band that is narrower than white light and are spaced from each other for a stereo view.

13. The medical endoscopy/stereo colposcopy instrument of claim 1, in which both cameras FFC1 and FFC2 are configured to image fluorescence and are spaced from each other for a stereo view.

14. The medical endoscopy/stereo colposcopy instrument of claim 1, in which:
the endoscopy camera at the distal end of the said single-use portion comprises:
a camera CamW that is configured to view a target in the patient and is responsive primarily to a wavelength range of white light;
a second electrically controlled color filter configured to selectively operate in a mode A to pass light primarily in a wavelength range of white light or in a mode B to light primarily in (i) a second selected narrow wavelength band that is narrower than white light or (ii) fluorescence light;
a forward-looking camera CamFA/B configured to view said target from a different angle and through said second color electrically controlled color filter; and
wherein said processor is operatively coupled with said display and configured to:
selectively switch said second color filter between mode A and mode B, and
receive image data from said cameras CamW and CamFA/B and:
form a white light stereo image of the target when said filter is operating in mode A;
form a selected narrow wavelength band image or a fluorescence light image from camera CamFA/B when said filter is operating in mode B; and
form and display at said display a composite image as an overlay of the white light stereo image and the selected narrow wavelength band image or fluorescent light image from said cameras CamW and CamFA/B.

15. The medical endoscopy/stereo colposcopy instrument of claim 14, in which the single-use portion extends along a longitudinal axis, the handle extends along a handle axis transverse to the longitudinal axis, the interlocking mount of the reusable portion has an upper portion that has an elongated, open slot extending along said longitudinal axis and the interlocking mount of the single use portion comprises an elongated hub extending along the longitudinal axis and configured slide into and snap-lock to said slot to thereby form the assembled endoscope.

16. The medical endoscopy/stereo colposcopy instrument of claim 14, wherein the reusable portion includes a manual bend controller mounted at a proximal end thereof and said single-use portion includes a bending mechanism that automatically engages said manual bend controller when the single-use portion is snapped into said slot and responds to manual operation of the bend controller to selectively bend the distal portion of the cannula.

17. The medical endoscopy/stereo colposcopy instrument of claim 14, in which said cannula is configured to rotate relative to the reusable portion.

18. The medical endoscopy/stereo colposcopy instrument of claim 14, in which said camera CamFA/B has a lower spatial resolution than said camera CamW at least when said second color filter is operating in said mode B.

19. A medical endoscopy/stereo colposcopy instrument comprising:
an L-shaped reusable portion comprising a downwardly extending handle and an axially extending housing;
a single-use portion comprising a hub removably secured to a proximal end of the housing and a cannula extending distally from the hub;
wherein:
one of said housing and hub comprises a mounting formed as an axially extending slot and the other comprises a mounting in the form of an axially extending rail configured to slide into the slot in the proximal direction and thereby removably secure the hub and cannula to the handle portion;
said proximal portion of the handle portion comprises an opening and said hub and cannula comprise a bending mechanism that is configured to bend a distal portion of the cannula and includes a proximally extending thumb lever that passes through said opening and protrudes proximally from the handle portion when the hub and handle portion are secured to each other and manual action on said thumb lever controls bending of said distal portion of the cannula;
an endoscopy camera module at the distal portion of the cannula;
a colposcopy camera module mounted to the housing and comprising colposcopy cameras FFC1 and FFC2 configured to view a target from different viewpoints; and
a display operatively coupled with the endoscopy camera module and to the colposcopy camera module to receive image data therefrom and display images based on the received image data.

20. A method of imaging a patient comprising:
taking stereo colposcopy images of a patient's cervix with cameras FFC1 and FFC2 mounted to a reusable portion to which a display is mounted;
taking endoscopy images of the patient's bladder or uterus with a single use portion that is removably coupled with the reusable portion to form an assembled endoscope and has at a distal end a camera CamW taking white light images and/or CamF taking images in a narrower wavelength band or fluorescence images; and displaying said colposcopy images and said endoscopy images at said display.

21. The method of claim 20, in which the taking of endoscopy images comprises taking images with both cameras CamW and CamF and the displaying comprises displaying a spatially registered superposition of the images from cameras CamW and CamF.

22. A medical endoscopy/colposcopy instrument comprising:

- a reusable portion that includes a handle configured to be grasped by a user's hand and a display mounted to the reusable portion;
- a forward-facing colposcopy imaging and lighting system mounted to said reusable portion;
- a single-use portion comprising a cannula configured for insertion in the patient and having an endoscopy imaging and lighting system at a distal end of the cannula;
- interlocking mounts at a proximal end of the single-use portion and at the reusable portion, configured to releasably couple the reusable and single-use portions to each other to thereby form an assembled endoscope configured to take endoscopy images with said endoscopic imaging and lighting system; and
- a processor configured to process the image data from the colposcopy and/or endoscopy imaging and lighting system into display images and to cause said display to show said display images.

23. The medical endoscopy/colposcopy instrument of claim 22, in which the colposcopy imaging and lighting system comprises a single colposcopy camera FFC1 and a colposcopy source S1 to provide a two-dimensional view.

24. The medical endoscopy/colposcopy instrument of claim 23, in which the colposcopy imaging and lighting system further comprises a second colposcopy camera FFC2 spaced from said camera FFC1 for a stereo view and a second colposcopy source S2.

* * * * *